US009493765B2

United States Patent
Krishnaswamy et al.

(10) Patent No.: US 9,493,765 B2
(45) Date of Patent: Nov. 15, 2016

(54) COMPACT SUBNANOSECOND HIGH VOLTAGE PULSE GENERATION SYSTEM FOR CELL ELECTRO-MANIPULATION

(75) Inventors: Pavitra Krishnaswamy, Cambridge, MA (US); Andras Kuthi, Thousand Oaks, CA (US)

(73) Assignee: UNIVERSITY OF SOUTHERN CALIFORNIA, Los Angeles, CA (US)

( * ) Notice: Subject to any disclaimer, the term of this patent is extended or adjusted under 35 U.S.C. 154(b) by 1422 days.

(21) Appl. No.: 12/079,017

(22) Filed: Mar. 24, 2008

(65) Prior Publication Data

US 2008/0231337 A1 Sep. 25, 2008

Related U.S. Application Data

(60) Provisional application No. 60/896,781, filed on Mar. 23, 2007.

(51) Int. Cl.
*C12M 1/42* (2006.01)
*C12N 13/00* (2006.01)
(Continued)

(52) U.S. Cl.
CPC ............. *C12N 13/00* (2013.01); *A61N 1/0412* (2013.01); *C12M 35/02* (2013.01); *H03K 3/537* (2013.01); *H03K 3/57* (2013.01); *H03K 5/159* (2013.01); *A61N 1/0408* (2013.01); *A61N 1/0452* (2013.01); *A61N 1/0456* (2013.01); *A61N 1/327* (2013.01)

(58) Field of Classification Search
CPC ....... C12M 35/02; H03K 3/537; H03K 3/57; H03K 5/159; C12N 13/00
USPC ...................................... 327/131; 435/285.2
See application file for complete search history.

(56) References Cited

U.S. PATENT DOCUMENTS 6,198,269 B1 * 3/2001 Beeley ........................ 323/361
6,809,563 B2 * 10/2004 Schaal ........................ 327/131
(Continued)

FOREIGN PATENT DOCUMENTS

JP 02304991 A * 12/1990

OTHER PUBLICATIONS

Molina et al. Sub-nanosecond avalanche transistor drivers for low impedance pulsed power applications. IEEE 2002, p. 178-181; p. 179, col. 1 to col. 2; p. 180, col. 1; p. 181.
(Continued)

*Primary Examiner* — William H Beisner
(74) *Attorney, Agent, or Firm* — Kilpatrick Townsend & Stockton LLP

(57) ABSTRACT

Disclosed are methods and systems for subnanosecond rise time high voltage (HV) electric pulse delivery to biological loads. The system includes an imaging device and monitoring apparatus used for bio-photonic studies of pulse induced intracellular effects. The system further features a custom fabricated microscope slide having micro-machined electrodes. A printed circuit board to interface the pulse generator to the micro-machined glass slide having the cell solution is disclosed. An low-parasitic electronic setup to interface with avalanche transistor-switched pulse generation system is also disclosed. The pc-board and the slide are configured to match the output impedance of the pulse generator which minimizes reflection back into the pulse generator, and minimizes distortion of the pulse shape and pulse parameters. The pc-board further includes a high bandwidth voltage divider for real-time monitoring of pulses delivered to the cell solutions.

12 Claims, 61 Drawing Sheets

(51) Int. Cl.
H03K 3/537 (2006.01)
H03K 3/57 (2006.01)
H03K 5/159 (2006.01)
A61N 1/04 (2006.01)
A61N 1/32 (2006.01)

(56) References Cited

U.S. PATENT DOCUMENTS

| | | | |
|---|---|---|---|
| 6,831,377 | B2 | 12/2004 | Yampolsky et al. |
| 2005/0118705 | A1 | 6/2005 | Rabbitt et al. |
| 2005/0264274 | A1* | 12/2005 | Dunning .................. 324/66 |
| 2006/0062074 | A1 | 3/2006 | Gundersen et al. |

OTHER PUBLICATIONS

Schoenbach et al. Intracellular Effect of Ultrashort Electrical Pulses Bioelectromagnetics 2001, 22:440-448.
Vyuga. Subnanosecond Pulsed-DC ultra-high gradient photogun for bright relativistic electron bunches. Ph.D. Thesis Aug. 31, 2006. [Retrieved from the Internet Jul. 26, 2008]: < http://alexandria.tue.nl/extra2/200611403.pdf>; chapter 3, p. 26-31, esp. p. 26, Section 3.1, first para; Section 3.3, p. 28, first para; Section 3.4, p. 30, first para.
Wijetunga et al. Electrical Modeling of Pulsed Power Systems for Biomedical Applications. Pulsed Power Conference 2003. Digest of Technical Papers. PPC-2003. 14th IEEE International vol. 1, Issue of Jun. 15-18, 2003 pp. 423-428 vol. 1: p. 1, 6.
International Search Report for PCT Application No. PCT/US08/03812, mailed on Aug. 4, 2008.
Barth. 1998. Rat brain tumor models in experimental neuro-oncology: the 9L, C6, T9, F98, RG2 (D47), RT-2 and CNS-1 gliomas. J Neurooncol. 36(1): pp. 91-102.
Behrend et al. 2003. Pulse Generators for pulsed electric field exposure of biological cells and tissues, IEEE Trans. Dielectr. Electr. Insul., vol. 10, pp. 820-825.
Behrend et al. 2004. DC to 1 Gigahertz multikilovolt voltage probe, 26th Intern. Power Modulator Symposium and High Voltage Workshop, pp. 341-343.
Bier et al. 1999. Kinetics of Sealing for Transient Electropores in Isolated Mammalian Skeletal Muscle Cells, Bioelectromagnetics, v20, pp. 194-201.
Borner et al. 1994. FEBS Lett. 353:pp. 129-132.
Cole et al. 2001. Time-domain whole-field fluorescence lifetime imaging with optical sectioning; Journal of Microscopy, vol. 203, Pt. 3, Sep. 2001, pp. 246-257.
Cossarizza et al. 2001. Chapter 21 Analysis of Mitochondria during Cell Death. Methods Cell Biology, vol. 63, pp. 467-486.
Craft et al. 1998. PhLPs and PhLOPs in the phosducin family of G beta gamma binding proteins. American Chemical Society, Biochemistry 37: pp. 15758-15772.
Cubeddu et al. 2002. Time-resolved fluorescence imaging in biology and medicine; Topical Review; Institute of Physics Publishing, J. Phys.D; Appl.Phys, 35: pp. R61-R76.
DeAngelis. 2001. Brain Tumors New England Journal of Medicine 344:pp. 114-123.
DeBruin et al. 1999. Modeling electroporation in a single cell. I. Effects of field strength and rest potential. Biophysical Journal 77:pp. 1213-1224.
Frank et al. 1998. High power pseudospark and BLT switches. IEEE Trans. Plasma Science 16 (2), pp. 317-323.
Freeman et al. 1994. Theory of electroporation of planar bilayer membranes: predictions of the aqueous area, change in capacitance, and pore-pore separation. Biophysical Journal 67: pp. 42-56.
Fulkerson et al. 1994. Design of Reliable High Voltage Avalanche Transistor Pulsers. IEEE 21st Intern. Power Modulator Symposium, pp. 101-103.
Gilbert et al. 1997. Novel electrode designs for electrochemotherapy. Biochimica et Biophys. Acta 1334, pp. 9-14.

Gotoh et al. 2002. Nitric Oxide-induced Apoptosis in RAW 264.7 Macrophages I s Mediated by Endoplasmic Reticulum Stress Pathway Involving ATF6 and CHOP. J. Biol. Chem. 277: pp. 12343-12350.
Hemker et al. 1999. Development of a parallel code for modeling plasma based accelerators. IEEE Particle Accelerator Conference 5, pp. 3672-3674.
Joshi et al. 2000. Electroporation dynamics in biological cells subjected to ultrafast electrical pulses: a numerical simulation study, Physical Review E 62: pp. 1025-1033.
Kirkman et al. 1986. Low pressure, light initiated, glow discharge switch for high power applications. Appl. Phys. Lett. 49, p. 494-495.
Kotnik et al. 2000. Theoretical evaluation of the distributed power dissipation in biological cells exposed to electric fields, Bioelectromagnetics 21: pp. 385-394.
Kuthi et al. 2005. Nanosecond Pulse Generator Using Fast Recovery Diodes for Cell Electromanipulation. IEEE Trans. Plasma Sci., vol. 33, pp. 1192-1197.
Lakowicz. 1985. Principles of Fluorescence Spectroscopy, Second Edition, Plenum Press, New York.
Li et al. 2002. Retinoic acid upregulates cone arrestin expression in retinoblastoma cells through a Cis element in the distal promoter region. Invest Ophthalmol Vis Sci 43: pp. 1375-1383.
Li et al. 2003. Gene expression networks underlying retinoic acid-induced differentiation of human retinoblastoma Cells Invest Ophthalmology & Vision Science, Mar. 2003, vol. 44, No. 3, pp. 996-1007.
Marcu et al. 1999. Photobleaching of arterial fluorescent compounds: characterization of elastin, collagen, and cholesterol time-resolved spectra during prolonged ultraviolet irradiation, Photochem. Photobiol. 69: pp. 713-721.
Marszalek et al. 1990. Schwan equation and transmembrane potential induced by alternating electric field, Biophysical Journal 58: pp. 1053-1058.
Mason. Ed. 1999. Fluorescence and luminescent probes for biological activity. A practical guide to technology for quantitative real-time analysis. Biological techniques series, Academic Press. Second Edition.
Maytin et al. 2001. Stress-Inducible Transcription Factor CHOP/gadd153 Induces Apoptosis in Mammalian Cells via p38 Kinase-Dependent and -Independent Mechanisms. Exp. Cell Res. 267: pp. 193-204.
Pogue et al. 2001. In vivo NADH Fluorescence Monitoring as an Assay for Cellular Damage in Photodynamic Therapy; Photochemistry and Photobiology, 74(6); pp. 817-824.
Polevaya et al. 1999. Time domain dielectric spectroscopy study of human cells. II. Normal and malignant white blood cells. Biochim. Biophys. Acta. 1419:pp. 257-271.
Schoenbach et al. 1997. The Effect of Pulsed Electric Fields on Biological Cells: Experiments and Applications, IEEE Transactions on Plasma Science, v25, pp. 284-292.
Schoenbach et al. 2001. Intracellular Effect of Ultrashort Electrical Pulses, Bioelectromagnetics, vol. 22, pp. 440-448.
Sun et al. 2005. Electrode microchamber for noninvasive perturbation of mammalian cells with nanosecond pulsed electric fields. IEEE Trans. Nanobiosci., vol. 4, pp. 277-283.
Vainshtein et al. 1997. A novel compact 35 A/150 ps current pulse generator for a new generation of the laser radars. 40th Midwest Symposium on Circuits and Systems, vol. 1, No. 3-6, pp. 148-151.
Vernier et al. 2003. Calcium bursts induced by nanosecond electric pulses. Biochemical and Biophyiscal Research Communications, vol. 310, pp. 286-295.
Vernier et al. 2005. Nanoelectropulseintracellular perturbation andelectropermeabilization technology: phospholipid translocation, calcium bursts, chromatin rearrangement, cardiomyocyte activation, and tumor cell sensitivity. 27th Annual Intern. Conf. IEEE Engineering in Medicine and Biology Society, Shanghai, pp. 5850-5853.
Wakita et al. 1995. Some Characteristics of the Fluorescence Lifetime of Reduced Pyridine Nucleotides in Isolated Mitochondria, Isolated Hepatocytes, and Perfused Rat Liver In Situ. J.Biochem. 118, pp. 1151-1160.

(56) References Cited

OTHER PUBLICATIONS

Watanabe et al. 2002. Feasibility and limitations of the rat glioma model by C6 gliomas implanted —at the subcutaneous region. Neurol. Res. 24(5): pp. 485-490.

Weaver et al. 1996. Theory of Electroporation: A Review. Bioelectrochemistry and Bioenergetics, v41, pp. 135-160.

Webb et al. 2002. A wide-field time-domain fluorescence lifetime imaging microscope with optical sectioning. Review of Scientific Instruments; vol. 73, No. 4 (Apr. 2002), pp. 1898-1907.

Weiss et al. 1984. The Role of T3 surface molecules in the activation of human t cells: a two-stimulus requirement for IL 2 production reflects events occurring at a pre-translational level. The Journal Immunology, vol. 133: pp. 123-128.

Zhu et al. 2000. The carboxyl terminal domain of phosducin finctions as a transcriptional activator. Biochemical and Biophysical Res. Comm. 270: pp. 504-509.

Zhu et al. 2002. Mouse cone arrestin gene characterization: promoter targets expression to cone photoreceptors. FEBS Letts 524 (1-3): pp. 116-122.

Zimmerman. 1996. Electromanipulation of Cells, CRC Press, Boca Raton Fla. Library of Congress Cataloging-in-Publication Data and Contents.

* cited by examiner

TABLE 1    50 vs 0    shocks increased genes after 6 hours

| Fold Increase | GenBank # ID | Gene | Function |
|---|---|---|---|
| 6.8 | X15376 | GABA-A receptor gamma 2 subunit | Inhibit synaptic transmission |
| 6.7 | A1535946 | EST | Unknown |
| 6.6 | X92720 | Mitochondrial phosphoenolpyruvate carboxykinase | Essential for gluconeogenesis and for growth |
| 5.4 | A1095013 | EST | Unknown |
| 4.9 | U26648 | Syntaxin 5 (transmembrane protien) | Regulating transport vesicle docking |
| 4 | U33635 | Human colon carcinoma kinase-4(CCK4) | Receptor tyrosine kinase (RTK transmembrane glycoprotein) |
| 3.7 | D16532 | Very low density lipoprotein receptor | Delivery of VLDL-derived fatty acids into adipose tissue |
| 3.6 | X68487 | A2b adenosine receptor | Anti-inflammation |
| 3.5 | J04027 | Plasma membrane Ca2+ pumping ATPase | Ca+Mg2+-ATPase expels Ca2+ from cells |
| 3.4 | U83981 | Apoptosis associated protein (GADD34) | DNA damage and growth arrest-inducible gene |
| 3.3 | AA126515 | EST | Unknown |
| 3.2 | M80899 | Novel protein AHNAK | Activates Phospholipase C-gamma1 |
| 3.1 | M25756 | Secretogranin II gene | Neuropeptide secreted by the ciliary epithelial cells |
| 3 | A1806222 | EST | Unknown |
| 3 | X95632 | Arg protien tyrosine kinase-binding protien P55pik (regulatory subunit for phosphatidylinositol 3-kinase) | Regulator and/or effector of Arg function |
| 2.8 | D88532 | Phosphatidylinositol 3-kinase catalytic subunit | Regulate insulin-like growth factor-1 receptor signaling |
| 2.8 | S81752 | KIAA0188 | Candidate tumor suppressor gene |
| 2.6 | D31797 | Diphthamide biosynthesis protein 2-like (DP112L) | Stimulates B cell proliferation and IgE secretion |
| 2.6 | L27476 | CD40 ligand gene | Unknown |
| 2.6 | M37815 | Human tight junction protien ZO-2 gene (X104) | Modulate T cell activation |
| 2.5 | U16307 | T cell membrane glycoprotein CD28 | highly expressed in the brain tumor glioblastoma multiforme |
| 2.5 | D87077 | Glioma pathogenesis-related protein (GIIPR) | Unknown |
| 2.4 | A1961743 | KIAA0240 | Unknown |
| 2.3 | Z29090 | EST | Regulate tyrosine kinase receptor signaling anti-apoptosis |
| 2.2 | D80010 | Phosphatidylinositol 3-kinase catalytic subunit | Potential serine protease |
| 2.2 | U83115 | KIAA0188 | Putative supressor of malignant melanoma |
| 2.1 | U26424 | Non-lens beta gamma-cristallin like protein (AIM1) | Induce apoptosis |
| 2.1 | Y10183 | Sle20-like kinase (MST2) | Cell adhesion molecule |
| 2.1 | I194BB1 | MEMD protein | Probable tumor suppressor |
| 2.1 | D28364 | S1 | Calcium-regulated exocytosis (absent in prostrate cancer) |
| 2.1 | U87947 | Annexin II | Possible role during active myelination |
| 2 | AL080061 | Hematopoietic neural membrane protein (HNMP-1) | Unknown |
| 2 | X66435 | cDNA DKFZp564H182 | Rate-limiting enzyme in the cholesterol synthetic pathway |
|  |  | HMG-COA-Synthase |  |

FIG. 4A

TABLE 1   50 vs 0   shocks increased genes after 1 hour

| Fold Increase | GenBank # ID | Gene | Function |
|---|---|---|---|
| 27.2 | S62138 | TLS-CHOP (FUS) or GADD153, CHOP (DDIT3) | Tumor-associated fusion gene |
| 25.0 | V01512 | Proto-oncogene c-fos (FOS) | Stress response gene |
| 21.3 | L49169 | GoS3 (FOSB) | Stress response gene |
| 15.9 | X68277 | CL 100 (DUSP1) | Tumor suppresor |
| 9.8 | J04111 | C-jun proto oncogene (JUN) | Stress response gene |
| 6.9 | D64109 | Tob family (TOB2) | Anti-proliferative protein |
| 4.0 | S62138 | TLS-CHOP (FUS) or GADD153, CHOP (DDIT3) | Tumor-associated fusion gene |
| 3.1 | U83981 | GADD34 (PP1R15A) | Stress response and growth arrest gene |
| 2.7 | M59287 | CDC-like kinase (CLK1) | Phosphorylation |
| 2.7 | M59830 | MHC class III HSP70-2 gene (HSPA1B) | Heat shock protein |
| 2.7 | X63575 | Plasma membrane calcium ATPase (ATP2B2) | Enzyme |
| 2.6 | AJ005694 | Short form of beta II spectrin (SPTBN1) | Membrane binding |
| 2.4 | X56681 | JunD (JUND) | Transcription factor |
| 2.2 | X52541 | Early growth response protein 1 (RGR1) | Transcriptional regulator |
| 2.2 | U66589 | Ribosomal protein L5 (RPL5) | 5S RNA binding protein |
| 2.1 | L27745 | Voltage-operated calcium channel, alpha-1 (CACNA1E) | Modulation of calcium |
| 2.1 | Z22576 | CD69 | Signal transmitting receptor |
| 2.1 | M62831 | ETR101 | Transcription factor |

FIG. 4B

TABLE 2   50 vs 0   shocks decreased genes after 6 hours

| Fold increase | GenBank # ID | Gene | Function |
|---|---|---|---|
| 2.4 | D85730 | Heat shock protein 70 testis variant | Anti-stress, anti-apoptosis |
| 2.3 | L26318 | JNK1 | Induce apoptosis |
| 2.2 | Y18264 | SAIL1 gene | Zine Encrypt transaction factor |
| 2.1 | M14758 | Multidrug resistance (MDR1) gene | Multidrug-resistance |

FIG. 5

TABLE 3  8 vs 0  shocks increased genes after 6 hours

| Fold increase | GenBank # ID | Gene | Function |
|---|---|---|---|
| 18.3 | X97198 | Receptor protein tyrosine phosphate (PCP-2) | Cell-cell recognition and adhesion |
| 15.6 | u49260 | Mevalonate pyrophosphate dacarboxylase | Enzyme in the cholestrol synthetic pathway |
| 11.7 | AD001530 | XAP-5 | Unknown |
| 4.6 | A1362017 | EST | Unknown |
| 3.4 | U40992 | Heat shock protein 40 (hsp40) | Anti-stress, anti-apoptosis |
| 2.9 | S81752 | Diphthamide biosynthesis protein 2-like (DPH2L) | Candidate tumor suppressor gene |
| 2.6 | Z22534 | Activin receptor-like kinase (ALK)-2 | Putative transmembrane protein serine/threonoine kinase |
| 2.3 | AF014837 | m6 A methyltransferase (MT-A70) | Posttranscriptional mRNA modification |
| 2.2 | AC006276 | Unknown | Unknown |
| 2.1 | W28235 | Human retina cDNA randomly primed sublibrary | Unknown |
| 2.1 | X77196 | Lysosome-associated membrane protein-2 | critical for autophagy |

FIG. 6

TABLE 4    8 vs 0 shocks decreased genes after 6 hours

| Fold increase | GenBank # ID | Gene | Function |
|---|---|---|---|
| 4.4 | L16895 | Lysyl-oxidase (LOX) gene | Extracellular matrix biosynthesis |
| 3.5 | AL050043 | Clone DKFZp566M0524 | Unknown |
| 3.4 | U91963 | Tolloid-like protein | Extracellular matrix biosynthesis |
| 3.1 | AA903299 | EST | Unknown |
| 3.1 | M29540 | Carcinoembryonic antigen (CEA) | |
| 2.8 | AI097085 | EST | Unknown |
| 2.6 | U32439 | Regulator of G protein signaling similarity (RGS7) | Regulate G protein signaling |
| 2.5 | U79298 | Clone 23803 | Unknown |
| 2.4 | AB018326 | KIAA0783 | Unknown |
| 2.1 | AB002438 | mRNA for chromosome 5q21-22 | Unknown |
| 2.1 | W28256 | Human retina cDNA randomly primed sublibrary | Unknown |
| 2 | AI375033 | EST | Unknown |
| 2 | M63108 | Luteinizing hormone-choriogonadotropin receptor | |
| 2 | Y18264 | SALL1 gene | Zinc finger transcription factor |

FIG. 7

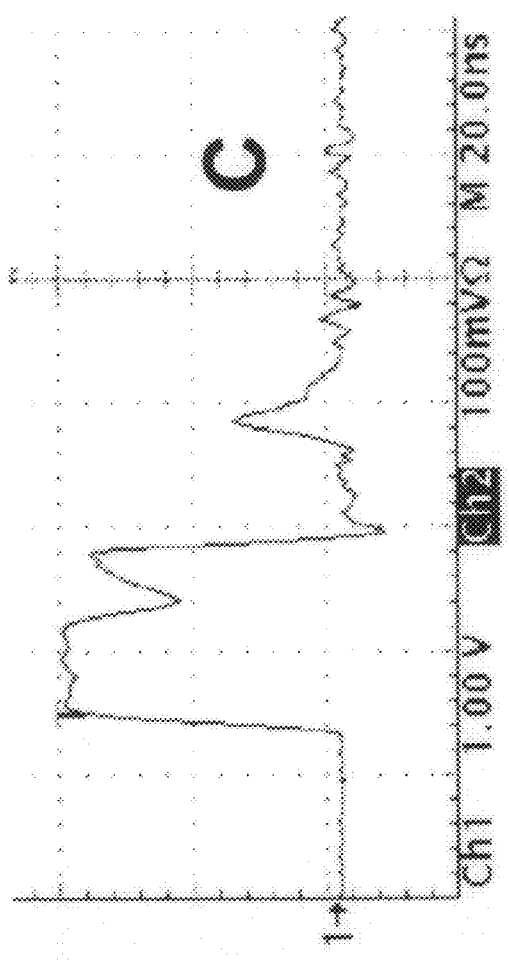

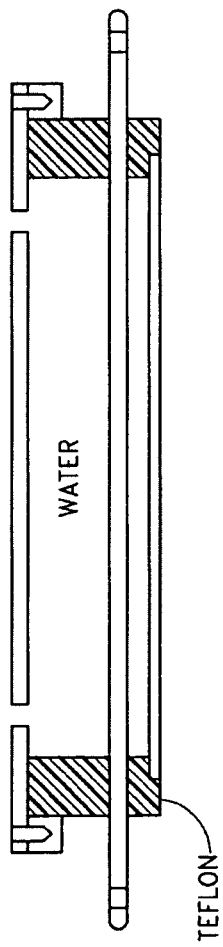
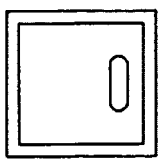
FIG. 22

FIG. 27A
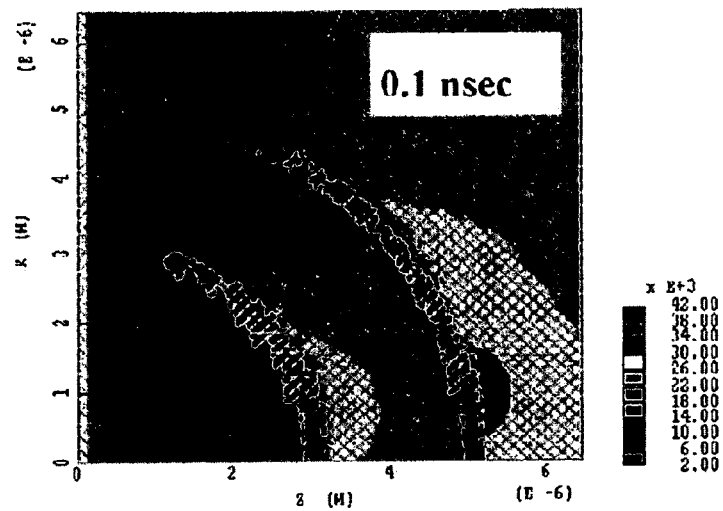
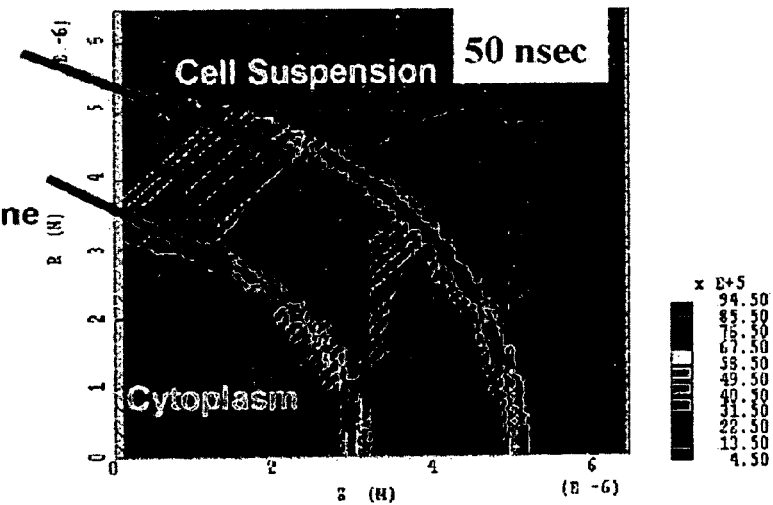
FIG. 27B

| Stage Number | Impedance ($\Omega$) | Capacitance (pF) |
|---|---|---|
| 2 | 10.5 | 1.8 |
| 3 | 17.1 | 6.8 |
| 4 | 24.6 | 3.3 |
| 5 | 30.1 | 2.2 |
| 6 | 36.5 | 1.5 |
| 7 | 44.7 | 1.0 |
| 8 | 50 | 0.8 |

FIG. 49

COMPACT SUBNANOSECOND HIGH VOLTAGE PULSE GENERATION SYSTEM FOR CELL ELECTRO-MANIPULATION

CROSS-REFERENCE TO RELATED APPLICATIONS

This application claims the benefit of and priority to under 35 U.S.C §119(e) of U.S. Provisional Application Ser. No. 60/896,781, filed on Mar. 23, 2007, entitled "Subnanosecond Pulse Generator for Cell-Electro-Manipulation," the entire content of which is incorporated herein by reference.

STATEMENT REGARDING FEDERALLY SPONSORED RESEARCH

The present invention was made with government support under the U.S. Air Force Office of Scientific Research Grant Nos. F29620-01-1-0387 and F49620-01-1-0495 and U.S. Army Research Office Grant No. DAAD 19-01-1-0698. The government may have certain rights in the invention.

FIELD OF THE INVENTION

The present invention is related generally to pulse generators for application of electric field pulses to cells to regulate the physiology and biophysical properties of various cell types, including terminally differentiated and rapidly dividing cells, and tissues. The application further discusses pulse generation, pulse delivery systems, radiofrequency voltage dividers, avalanche breakdown, microscope biomems experimental setups, ultrashort pulse delivery systems, bioelectric phenomena, electroperturbation and biomembranes.

BACKGROUND OF THE INVENTION

Electroporation refers to the phenomena of rearranging the structure of the membrane or membranes of cells to introduce or modify porosity across the membrane film, thereby creating a mechanism for transport between the extra-cellular and intracellular fluids, caused by application of an electric field. (Zimmerman U, Electromanipulation of Cells, CRC Press, Boca Raton Fla., 1996, herein incorporated by reference).

Pulsed electric fields have long been under investigation for causing many different biological effects. Yet, in spite of decades of research, there is an incomplete understanding of the interaction of electromagnetic fields within biological cells and tissues. Investigations of pulsed electric fields and microwave radiation aimed at achieving cell effects such as electroporation have historically utilized relatively long pulse lengths, such as pulses greater than 1μsecond, and microwave radiation approaching the thermal-heating regime. Studies of the interactions of RF and microwave electromagnetic fields on biological systems have been limited by the use of these long pulse lengths, or continuous wave radiation, which reduces the coupling of high electric fields into the interior of the cell.

Aqueous pores, typically about 1 nm in diameter, have creation rates typically on the order of microseconds, and possibly shorter with rapidly pulsed fields. Depending on the process for pore formation, resealing of a pore may take much longer (Weaver J C, Chizmadzhev Y A, Theory of Electroporation: A Review, Bioelectrochemistry and Bioenergetics, v 41, 1996, pp. 135-160; Bier M, Hammer S M, Canaday D J, Lee R C, Kinetics of Sealing for Transient Electropores in Isolated Mammalian Skeletal Muscle Cells, Bioelectromagnetics, v20, 1999, pp. 194-201, herein incorporated by reference). Typical field strengths required for electroporation vary between hundreds of volts/cm to kilovolts/cm, depending on the duration of the field. The external field increases the transmembrane potential from about 80 mV to a much larger value, facilitating porosity. It has been consistently shown that once the transmembrane potential reaches or exceeds about the one volt threshold, pores form, resulting in membrane permeabilization, molecular uptake, or lysis from osmosis. There is limited understanding of the membrane dynamics during pore formation. Although modeling captures some linear and even nonlinear aspects of electroporation, the model itself must use variables empirically derived from gathered data, and are qualitative, because of the present limited understanding of membrane physics (Schoenbach K H, Perterkin F E, Alden R W, Beebe S J, The Effect of Pulsed Electric Fields on Biological Cells: Experiments and Applications, IEEE Transactions on Plasma Science, v25, 1997, pp. 284-292, herein incorporated by reference).

SUMMARY OF THE INVENTION

It is one object of the current invention to provide a method in which one or more electric field pulses are applied to a cell to regulate cellular physiology and biophysical properties. In one embodiment, gene transcription is regulated. In another embodiment, an electric field pulse is applied to a eukaryotic cell at a voltage and duration sufficient to cause electroperturbation. In one embodiment the electric pulse has duration of less than about 100 nanoseconds. In one embodiment, the electric field is greater than 10 KV/cm. In one embodiment, at least one electric field pulse has pulse duration of less than about 10 nanoseconds. In another embodiment, the pulse duration is less than about 1 nanosecond. In a further embodiment, one or more genes are selected for transcription. These selected genes include genes that show transcriptional changes after about one hour post electroperturbation. These "one hour" genes include, but are not limited to, ASNS, CHOP (GADD153), CLIC4, CD45, CD53, p36, CD58, AICL FOS, FOSB, DUSP1, JUN, TOB2, GADD34, CLK1, HSPA1B, JUND, EGR1, CACNA1E, CD69 and ETR01. In another embodiment, these selected genes include genes that show transcriptional changes after about six hours post electroperturbation. These "six hour" genes include, but are not limited to, ITPKA, AHNAK, EMP3, ADORA2B, POU2AF1, AIM1, ATP1G1, ASNS, ETS2, CD45, VIM, TGIF, LAT, CLIC4, SLC7A5, ZFP36L2, RUNX1, SLC3A2, IFRD1, and PrP.

It is another object of several embodiments of the present invention to provide a method to determine the induction of cellular gene transcription in response to electropertubation. In one embodiment, at least one electric field pulse is applied to one or more cells. In one embodiment, each electric field pulse has duration of less than about 100 nanoseconds. In another embodiment at least one electric field pulse has a duration less than about 10 nanoseconds. In yet another embodiment, the pulse duration is less than about 1 nanosecond. After the electric field pulse is applied, at least one cell that is electroperturbed is identified and isolated. Cellular gene transcription in the electroperturbed cell is then determined. In a preferred embodiment, the electroperturbed cell is identified based upon cellular morphology or cellular biochemistry. In one embodiment, fluorescent staining is used as a tool to identify changes in cellular morphology or cellular biochemistry.

It is another object of several embodiments of the current invention to provide a method of sensitizing a eukaryotic cell to a therapeutic agent. In one embodiment, at least one electric field pulse is applied to a cell to produce a sensitized cell. Each electric field pulse has duration of less than about 100 nanoseconds. In one embodiment, at least one electric field pulse has pulse duration of less than about 10 nanoseconds. In another embodiment, the pulse duration is less than about 1 nanosecond. One or more therapeutic agents are applied to the sensitized cell and the effect of the therapeutic agent is enhanced in the sensitized cells. Therapeutic agents include, but are not limited to, nucleic acids, polypeptides, viruses, enzymes, vitamins, minerals, antibodies, vaccines and pharmaceutical agents. In one embodiment, the pharmaceutical agent is a chemotherapeutic compound. One skilled in the art will understand that one or more therapeutic agents can be applied to the cell and that these agents can be applied before, after or during sensitization of the cell. In one embodiment, the pulse duration is less than about 1 nanosecond and the electric field is greater than about 10 kV/cm.

It is another object of the present invention to provide a method of sensitizing a eukaryotic cell to a therapeutic method. In one embodiment, at least one electric field pulse to a cell, wherein each electric field pulse has a pulse duration of less than about 100 nanoseconds, to produce a sensitized cell. In one embodiment, at least one electric field pulse has a pulse duration of less than about 10 nanoseconds. In another embodiment, the pulse duration is less than about 1 nanosecond. One or more therapeutic methods are then applied to the cell. The effect of the therapeutic method is enhanced in the sensitized cells. Therapeutic methods include, but are not limited to, photodynamic therapy, radiation therapy and vaccine therapy. One skilled in the art will understand that one or more therapeutic methods can be applied to the cell and that these methods can be applied before, after or during sensitization of the cell. In one embodiment, the pulse duration is less than about 1 nanosecond and the electric field is greater than about 10 kV/cm.

It is another object of several embodiments of the current invention to provide a method in which one or more electric field pulses are applied to a cell to mark or target the cell for diagnostic or therapeutic procedures. In one embodiment, at least one electric field pulse is applied to one or more cells. At least one electric field pulse has a pulse sufficient to induce a cellular response in said cell, wherein the cellular response marks the cell for diagnostic or therapeutic procedures. In one embodiment, the duration of each pulse is less than about 100 nanoseconds. In a further embodiment, at least one electric field pulse has a pulse duration of less than about 10 nanoseconds. In another embodiment, the pulse duration is less than about 1 nanosecond. In one embodiment, the cell is "marked" by affecting one or more characteristics of the cell, including but not limited to, gene transcription, gene translation, protein synthesis, post-translational modifications, protein processing, cellular biosynthesis, degradative metabolism, cellular physiology, cellular biophysical properties, cellular biochemistry and cellular morphology. In one embodiment, the cellular response induced by the electric field pulse includes the translocation of cellular membrane components, including proteins and phospholipids. In one embodiment, the phosphatidylserine component of the cytoplasmic membrane of the cell is inverted. In one embodiment, the diagnostic or therapeutic procedure includes lysing the cell.

In another embodiment of the present invention, a method of disrupting an intracellular membrane of a eukaryotic cell is provided, including, but not limited to, the cytoplasmic membrane, nuclear membrane, mitochondrial membrane and segments of the endoplasmic reticulum. In one embodiment, at least one electric field pulse is applied to a cell at a voltage and duration sufficient to induce disruption of the membrane. In one embodiment, each electric field pulse has a pulse duration of less than about 100 nanoseconds. In one embodiment, at least one electric field pulse has a pulse duration of less than about 10 nanoseconds. In another embodiment, the pulse duration is less than about 1 nanosecond. In another embodiment, the electric field is greater than about 10 kV/cm. Disruption of the intracellular membrane includes, but is not limited to, translocating membrane components. These components include, but are not limited to, phospholipids, including phosphatidylserine, proteins or other components.

In yet another embodiment of the present invention, a method of marking a eukaryotic cell for phagocytosis is provided. In a further embodiment, at least one electric field pulse to the cell is applied to a cell at a voltage and duration sufficient to induce a cellular response in the cell, wherein the cellular response marks the cell for phagocytosis. The cellular response includes, but is not limited to, translocating membrane components. These components include, but are not limited to, phospholipids, including phosphatidylserine, proteins or other components. In a further embodiment, each electric field pulse has a pulse duration of less than about 100 nanoseconds. In one embodiment, at least one electric field pulse has a pulse duration of less than about 10 nanoseconds. In another embodiment, the pulse duration is less than about 1 nanosecond. In one embodiment, the electric field is greater than about 10 kV/cm.

It is yet another object to provide a method in which one or more electric pulses are applied to a cell to determine cellular tolerance to electric pulses. In one embodiment, a first electric field pulse is applied to one or more cells, and electroperturbed cell are identified, isolated and assayed for one or more indicators of cellular response. Then, a second electric field pulse is applied to the cells. In one embodiment, the second electric field is not equal to the first electric field. After this second treatment, the electroperturbed cell are again identified, isolated and assayed for one or more indicators of cellular response. The indicators of cellular response after application of the first electric field are compared with the indicators of cellular response after application of the second electric field. The indicators of cellular response include, but are not limited to, changes in gene transcription, gene translation, protein synthesis, post-translational modifications, protein processing, cellular biosynthesis, degradative metabolism, cellular physiology, cellular biophysical properties, cellular biochemistry and cellular morphology.

It is another object of several embodiments to selectively electroperturb a population of cells based upon the cell's dielectric properties. In one embodiment, the dielectric properties are exploited to selectively reduce proliferation of rapidly dividing cells in a patient. In one embodiment, dielectric properties of one or more cells in two populations of cells are determined. An electric field pulse based on these dielectric properties is then determined, wherein the electric field pulse selectively electroperturbs the first sub-population of cells without substantially affecting the second population of cells. This electric field pulse is then applied to the cells. The first sub-population of cells includes, but is not limited to, abnormal or unhealthy cells, such as rapidly dividing cells. The second population of cells includes cells that are to remain substantially unaffected by the electric pulse, such as terminally differentiated cells. In another embodiment the first sub-population of cells includes one type of rapidly dividing cell and the second population of cells includes a second type of rapidly dividing cell. In a further embodiment, the electroperturbation induces changes in a cellular response, including, but not limited to, changes in gene transcription, gene translation, protein synthesis, post-translational modifications, protein processing, cellular biosynthesis, degradative metabolism, cellular physiology, cellular biophysical properties, cellular biochemistry and cellular morphology. Rapidly dividing cells, as used herein, shall be given its ordinary meaning and shall also mean cells that are metabolically active and that can divide through mitosis and duplicate themselves. Rapidly dividing cells include, but are not limited to tumorigenic cells and cancerous cells. Terminally differentiated cells, as used herein, shall be given its ordinary meaning and shall mean cells that are metabolically active, but cannot divide to create daughter cells. Terminally differentiated cells include, but are not limited to non-tumorigenic cells and healthy cells.

In another embodiment, a method of selectively regulating gene transcription in rapidly dividing cells is provided. In this embodiment, a cell suspension containing rapidly dividing cells and terminally differentiated cells is obtained and at least one electric field pulse is applied to the suspension. Each electric field pulse has a pulse duration and intensity sufficient to induce gene transcription primarily only in the rapidly dividing cells.

It is yet another object to provide a therapeutic method in which a patient's tissue is removed and subsequently treated with one or more electric field pulses. In one embodiment, a method of reducing proliferation of rapidly dividing cells in a patient is provided. In this embodiment, a portion of a patient's tissue that contains rapidly dividing cells and terminally differentiated cells is removed. At least one electric field pulse is applied to one or more cells in the tissue, wherein each electric field pulse has a pulse duration of less than about 100 nanoseconds. In one embodiment, at least one electric field pulse has a pulse duration of less than about 10 nanoseconds. In another embodiment, the pulse duration is less than about 1 nanosecond. The tissue is then reintroduced to the patient. In another embodiment, one or more electric field pulses having a duration of greater than about 100 nanoseconds is used in combination with an electric field pulse having a duration of less than about 100 nanoseconds. Tissue, as defined herein, shall be given its ordinary meaning and shall also mean a collection of similar cells and the intercellular substances surrounding them. Tissue, as used herein, shall include: (1) epithelium; (2) the connective tissues, including blood, bone, and cartilage; (3) muscle tissue; and (4) nerve tissue. (Stedman's Medical Dictionary Illustrated, Twenty-Third Edition, The Williams & Wilkins Company, Baltimore.) Tissue, as used herein, shall also include, cerebrospinal fluid, lymphatic fluid and bone marrow.

It is another object of several embodiments of the current invention to provide a method in which at least two electric field pulses are applied to a cell to facilitate entry of a diagnostic or therapeutic agent into a cell's intracellular structures. In one embodiment, a relatively "long" electric field pulse is applied to cell followed by a relatively "short" electric field pulse. In one embodiment, the method includes applying at least one first electric field pulse to the cell sufficient to cause electroporation, incubating the cell with the therapeutic agent, and applying one or more second electric field pulses to one or more cells in the tissue, wherein each second electric field pulse has a pulse duration of less than about 100 nanoseconds. The therapeutic agent includes, but is not limited to, nucleic acids, polypeptides, viruses, enzymes, vitamins, minerals, antibodies, vaccines and pharmaceutical agents. In one embodiment, the pulse duration of the relatively "short" pulse is from about 1 nanosecond to about 10 nanoseconds. In another embodiment, the pulse duration of the relatively "short" pulse is less than about 1 nanosecond and the electric field is greater than about 10 kV/cm. In a further embodiment, the pulse duration of the relatively "long" pulse is greater than about 100 nanoseconds. In another embodiment, the pulse duration of the relatively "long" pulse is greater than about 1 millisecond.

It is a further object of the present invention to provide a method for identifying effective therapeutic agents. Such an agent can be effective in reducing cell proliferation. Agents that induce apoptosis can also be identified in accordance with several embodiments of the current invention. In one embodiment, at least one putative therapeutic agent is applied to a cell. The regulation of at least one cell-cycle control gene, stress-response gene or immune response gene is then determined. If at least one of these genes is up-regulated, the putative therapeutic agent is identified as an effective therapeutic agent. In one embodiment, the cell-cycle control genes, stress-response genes or immune response genes include, but are not limited to, ASNS, CHOP (GADD153), CLIC4, CD45, CD53, p36, CD58, AICL FOS, FOSB, DUSP1, JUN, TOB2, GADD34, CLK1, HSPA1B, JUND, EGR1, CACNA1E, CD69, ETR01, ITPKA, AHNAK, EMP3, ADORA2B, POU2AF1, AIM1, ATP1G1, ASNS, ETS2, CD45, VIM, TGIF, LAT, CLIC4, SLC7A5, ZFP36L2, RUNX1, SLC3A2, IFRD1 and PrP. In one embodiment, the putative therapeutic agent includes, but is not limited to, nucleic acids, polypeptides, viruses, enzymes, vitamins, minerals, antibodies, vaccines and pharmaceutical agents.

It is another object of several embodiments of the current invention to provide a pulse generator circuit that may include a diode configured to operate as an opening switch, a tank circuit in series with the diode having an admittance that is switchable from a first value to a second value that is different from the first value, and a switching system configured to cause the tank circuit to switch between the first value and the second value.

It is another object of several embodiments of the current invention to provide a switching system that may include a first and a second electronic switch. The first switch may be configured to cause the diode to be forward biased upon closure. The second switch may be configured to cause the diode to be reversed biased upon closure.

It is another object of several embodiments of the current invention to provide a diode that may be configured to be forward biased and reverse biased at different times. The switching system may be configured to cause the admittance of the tank circuit to be at the first value while the diode is forward biased and to be at the second value while the diode is reverse biased.

It is another object of several embodiments of the current invention to provide a tank circuit that may include a first and a second capacitance and a first and a second inductance. The product of the first capacitance and the first inductance may be approximately the same as the product of the second capacitance and the second inductance.

It is another object of several embodiments of the current invention to provide a switching system that may be configured to include the first and the second capacitance and the first and the second inductance in the tank circuit while the diode is forward biased. The switching system may be configured to include the second capacitance and the second inductance in the tank circuit, but not the first capacitance and the first inductance, while the diode is reverse biased.

It is another object of several embodiments of the current invention to provide a switching system that may be configured to transfer charge from the first capacitance to the second capacitance. The switching system may be configured to transfer charge only while the diode is forward biased.

It is another object of several embodiments of the current invention to provide a pulse generator circuit that may include a diode that that is configured to operate as an opening switch and that saturates in less than 100 nanoseconds, and a saturable core transformer configured to operate as a switch that controls the opening of the diode.

It is another object of several embodiments of the current invention to provide a pulse generator that may include a tank circuit that includes the saturable core transformer and that is in series with the diode It is another object of several embodiments of the current invention to provide a tank circuit that may have an admittance that is switchable from a first value to a second value that is different from the first value.

It is another object of several embodiments of the current invention to provide a saturable core transformer that may be configured to cause the admittance to switch from the first value to the second value. The first value of the admittance may be approximately half of the second value.

It is another object of several embodiments of the current invention to provide a tank circuit that may include a first and a second capacitance.

It is another object of several embodiments of the current invention to provide a pulse generator may include a MOSFET configured to cause the first and the second capacitance to be part of the tank circuit while the diode is forward biased and to cause the second capacitance to be part of the tank circuit, but not the first capacitance, while the diode is reversed biased.

It is another object of several embodiments of the current invention to provide an apparatus for electropertubation of biological cells that may include a pulse generator configured to generate a plurality of pulses, each having a length of no more than 3 nanoseconds and an amplitude of at least 1 kilovolt, and electrodes connected to the pulse generator configured to deliver the plurality of pulses to biological cells.

It is another object of several embodiments of the current invention to provide a pulse generator that may be configured to deliver the plurality of pulses at a frequency of at least 100 kHz.

It is another object of several embodiments of the current invention to provide a pulse generator that may include a diode that is configured to operate as an opening switch and that saturates in less than 100 nanoseconds.

It is another object of several embodiments of the current invention to provide a pulse generator to drive low impedance biological cell loads at high repetition rates for intracellular electromanipulation studies. The system constitutes a subnanosecond pulse generator, a high bandwidth voltage monitor and a delivery system that interfaces the subnanosecond pulse generator and the voltage monitor with the biological cell load under study and the microscope imaging system that is used to conduct biophotonic studies of intracellular effects induced by subnanosecond high voltage pulses.

It is another object of several embodiments of the current invention to provide a pulse generator as part of a system above to generate subnanosecond rise time with high voltage pulse. Our circuit adapts a generation architecture used to drive a high impedance capacitive Pockel's cell load to one that can deliver low energy pulsed fields to a low impedance biological loads at high repetition rates.

It is another object of several embodiments of the current invention to provide a voltage divider for real time direct measurement of subnanosecond rise time high voltage pulses.

It is another object of several embodiments of the current invention to provide a biophotonic setup to ensure a good match between the subnanosecond pulse generator and the low impedance biological load under study.

It is another object of several embodiments of the current invention to provide a biophotonic setup that enables the delivery of an undistorted subnanosecond rise-time high voltage pulse at high repetition rates to the load.

It is another object of several embodiments of the current invention to provide a setup to facilitate microscopic observation of cellular responses to the pulses, as and when they are delivered.

BRIEF DESCRIPTION OF THE DRAWINGS

FIGS. 4A-B list up-regulated genes. FIG. 4A is a table listing genes with increased transcription following 50 electric field pulses after 6 hours. FIG. 4B is a table listing genes with increased transcription following electric field pulses after 1 hour.

FIG. 5 is a table listing genes with decreased transcription following 50 electric field pulses after 6 hours.

FIG. 6 is a table listing genes with increased transcription following 8 electric field pulses after 6 hours.

FIG. 7 is a table listing genes with decreased transcription following 8 electric field pulses after 6 hours.

FIG. 14C shows a typical 20 nanosecond pulse producing a field of 20 kV/cm.

FIG. 22 illustrates an asymmetric water stripline.

FIGS. 27A and 27B show a 2-D spherical electromagnetic model for a cell demonstrating the effect of the short pulse on the interior membrane, where contour plots of the electric field are shown at 0.1 nanosecond (27A) and 50 nanoseconds (27B).

FIG. 49 depicts a table of capacitances in the tapered transmission line embodiment.

DETAILED DESCRIPTION

Recent research has demonstrated that very short, high-field, electric pulses, generated by advanced pulsed power technology, can reach the interior of biological cells without damaging the external membrane. By taking advantage of the dielectric properties of the cell and its subcellular components, nanosecond, megavolt-per-meter electric field pulses (Ultrashort Pulse Systems Electroperturbation Technology or "UPSET") can polarize internal cellular structures without developing critical voltages across the cytoplasmic membrane. These relatively intense, relatively ultrashort (relatively high power but relatively low total energy) pulses provide a mechanism for delivering variable, but precisely controllable intracellular electrical and mechanical perturbations to a variety of biological systems (single cells, cell suspensions, tissues, organs).

The term electroperturbation is used to characterize the perturbative effects of ultrashort electric pulses on internal organelles and cell membranes, and at proteomic and genomic levels. The present UPSET technology offers the possibility of applying relatively high fields that do not permanently injure the cell, but which do affect field-sensitive and stress-sensitive intracellular elements, such as nuclear and mitochondrial membranes, biochemical equilibria dependent on molecular dipoles, and stretch-sensitive components of the cytoskeleton and endoplasmic reticulum (ER).

Regulation of Gene Transcription

A. UPSET Technology

Figure 9:
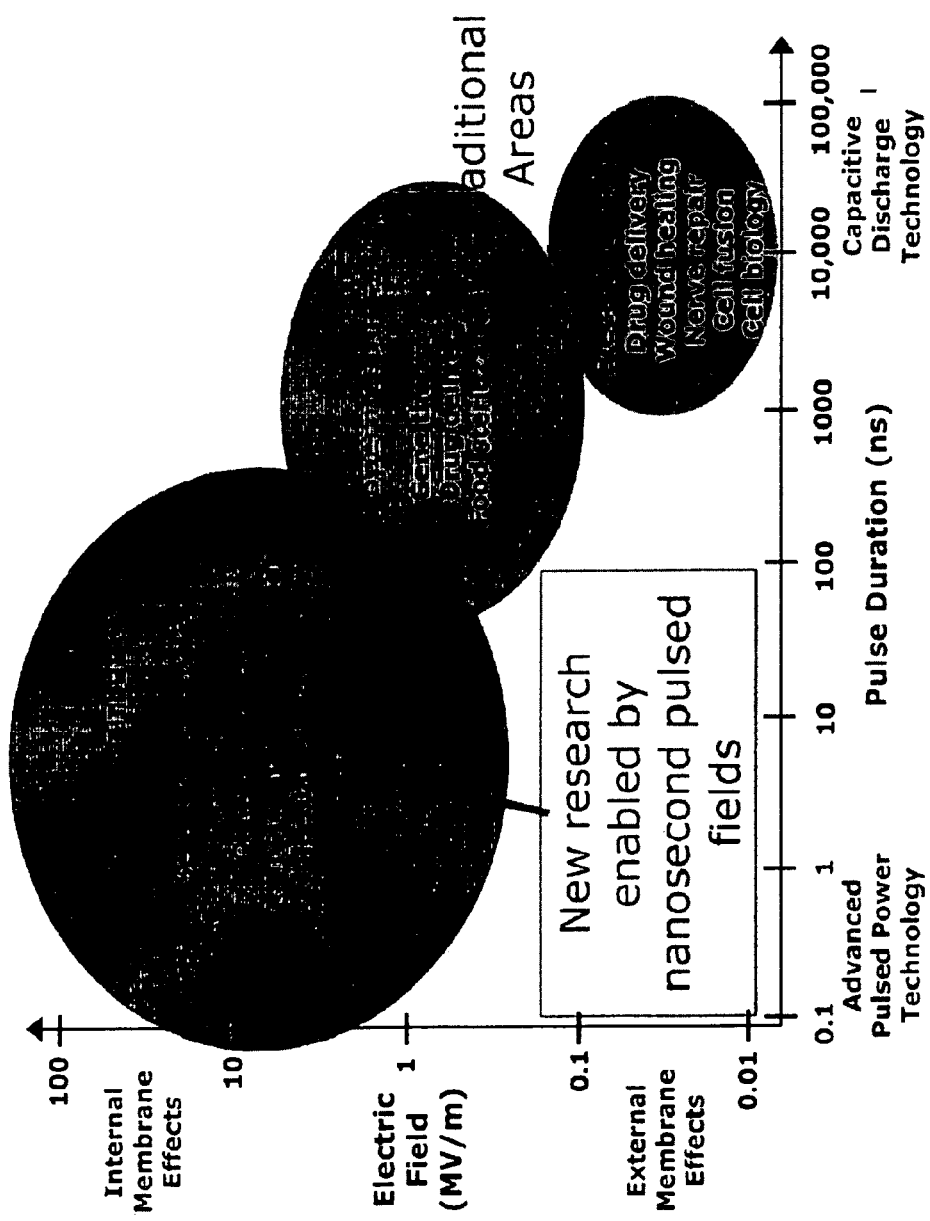
FIG. 9 shows the onset of intracellular effects and penetration into the cell (upper left) as a function of pulse length and electric field.

As discussed above, in several embodiments of the current invention, the novel UPSET technology provides a system for applying relatively high electric fields to cells that affect internal membrane and cytoskeletal biophysics and biochemistry, without permanently injuring the cell. UPSET technology also selectively stimulates specific populations of cells in physiologically significant ways. Some potential areas in which UPSET technology can be used are indicated in FIG. 9, discussed below, which shows the range of effects as a function of electric field intensity and pulse duration. Malignant cells, for example, can be more sensitive than normal cells to a sequence of ultrashort, high-field pulses, and such a differential sensitivity has important therapeutic implications.

Pulsed electric fields have been investigated for a variety of biological effects and as a tool for understanding the biophysics of cell membranes and cellular responses to fields across the frequency spectrum. Microsecond, kV/m, pulsed electric fields produce non-lethal conductive pores in the cytoplasmic membrane. This cell permeabilization technology, called electroporation, is widely used for introducing normally excluded substances into cells, including pharmaceutical compounds and nucleic acids. For example, electroporation facilitates cellular uptake and integration of genetic material and is included in protocols for genomic research, genetic engineering and gene therapy. Electroporation pulses range from a few to hundreds of kilovolts per meter in amplitude and from microseconds to milliseconds in duration. Extending the pulse period or increasing the amplitude or delivering a greater number of pulses results in a greater number of larger pores, but with the accompanying penalty of increased lethality to the cell.

As distinct from electroporative pulses, much shorter (electroperturbative) pulses with a duration less than the charging time constant of the plasma membrane (typically less than about 100 nanoseconds) produce voltages within the cell and across the intracellular membranes (dielectric shells) of the nucleus, mitochondria, and other organelles. Very short pulses, and the edges of pulses with very fast rise or fall times, "pass through" the cytoplasmic membrane and, for pulsed field magnitudes greater than about 1 megavolt per meter, produce potentials across intracellular structures large enough to cause depolarization or pore formation in the internal membranes. Electroperturbation pulses extend the electrical regime of electroporation to high electric field amplitude and very short pulse duration.

To describe the electrical engineering aspects of electroperturbation, the biological cell may be considered to be comprised of a conductive medium surrounded by a dielectric shell, which is immersed in another conductive medium. From this starting point, Maxwell's equations and basic circuit theory lead to models of arbitrary complexity, in the simplest of which cells are represented as lumped circuit elements. These models predict that cells respond to very short pulsed fields (tens of nanoseconds or less) in such a way that instead of appearing across the external membrane "capacitor", the applied field is expressed across intracellular structures and membranes, i.e., the externally applied field is capacitively coupled into the cell.

The Analytical Platform: Experimental and Computational Systems

Experimental and computational systems, described below, are used in conjunction with several embodiments of the current invention, to provide a novel real-time and analytical platform for investigations into the effects of electric field pulses at the sub-cellular level.

Optical imaging investigations have demonstrated potential for 1) acquiring information at molecular, sub-cellular, and cellular levels, and 2) delineating and recognizing diagnostic signatures in situ, noninvasive or minimally invasive, and in near- or real-time. Therefore, development and application of non-invasive imaging and monitoring systems with high optical sensitivity and resolution enables in situ investigations of biological systems subject to external electromagnetic (including fast electric pulses), chemical, magnetic, thermal and/or mechanical stimuli. (Marcu L, Grundfest W. S., Maarek J. M, "Photobleaching of arterial fluorescent compounds: characterization of elastin, collagen, and cholesterol time-resolved spectra during prolonged ultraviolet irradiation", Photochem. Photobiol. 69:713-721, 1999; J. R. Lakowicz, "Principles of Fluorescence Spectroscopy", Plenum Press, New York (1985), all herein incorporated by reference).

Moreover, fluorescence spectroscopy/imaging provides specific signatures with respect to biochemical composition of biological systems. Time-resolved spectroscopy/imaging methods improve the specificity of fluorescence measurements and the use of time-resolved fluorescence approaches for biological systems characterization offers several distinct advantages including: 1) sensitivity to various parameters of biological systems microenvironment (including pH, ion concentration and binding, enzymatic activity, temperature) thus allowing these variables to be analyzed; 2) discrimination between biomolecules with overlapping fluorescence emission spectra but with different fluorescence decays, thus preferable for multi-labeling experiments; and 3) its ability to be contrasted against an autofluorescence background arising from the same detected microscopic volume element.

Computational science is used to develop realistic electrical models of the cell and its surroundings as the cell responds to the fields. This is used in guiding the design of pulsed field experiments and interpreting the results. This allows the experimental investigation of electro-manipulation and diagnosis of cells with a computational modeling program that applies state-of-the-art tools in electromagnetic simulation from the electrical engineering community to the study of the electrical response of living cells to tailored electrical pulses. This may allow for a predictive modeling of the detailed three-dimensional electric field structure induced in the cell as a function of realistic applied voltage characteristics and cell characteristics, and allow rapid testing and exploration of new regimes (e.g., shorter pulses) that may be too expensive or time-consuming to explore experimentally. These experimental and computational systems provide a unique real-time and analytical platform for investigations at the sub-cellular level.

The use of equivalent circuits to solve partial differential equations was demonstrated in the era of analog computers, but new methods of modeling biological cells are described herein. In one embodiment, circuit simulation software was used. A well-known circuit simulation program, SPICE, was used in accordance with several embodiments of the present invention. However, one skilled in the art will understand that other circuit simulation software can also be used. The use of equivalent circuits allows both linear and nonlinear models to be used simultaneously for cell membrane interactions. For example, simple models for the fixed portion of the cell membrane resistance and capacitance, and more complex models to represent a population of ion channels and to represent electroporation (nonlinear transmembrane voltage dependence) are used. This approach also includes representation of both the conduction and dielectric properties of intra- and extra-cellular electrolytes. Once an electrical model has been created from an experimental image, the circuit corresponding to the network is solved by SPICE in the frequency or time domain. Equipotentials, transmembrane voltages, current densities and related distributions are then constructed from the simulation results. In the case of subcellular or cellular electroporation a nonlinear, hysteretic membrane model was used to represent poration of small membrane regions that exceed a threshold transmembrane voltage. The result was then used as a distributed input to a thermal network, and the transient or steady state temperature rise was computed. This provided a basis for asserting that temperature rise distribution for "non-thermal" exposures were relatively small throughout the system. Finally, diffusion and electrophoretic molecular transport can be predicted for the same model. For ultrashort pulses that electroporate nuclear or mitochondrial membranes, models for hindered transport through pores and within the cytoplasm or internal subcellular structure are used to predict movement of small and large molecules within the cell.

Intracellular Effects

Figure 8A:
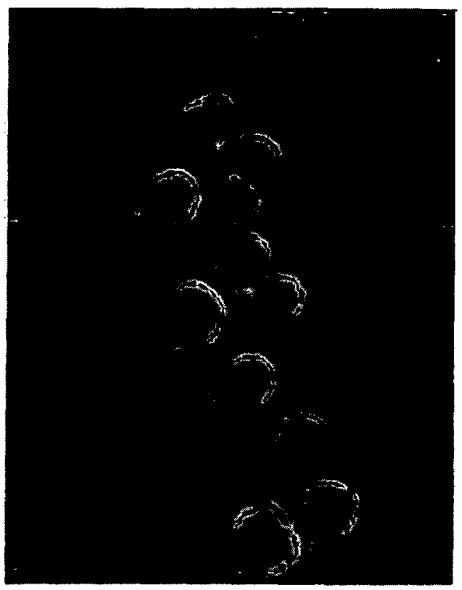
FIGS. 8A and 8B are micrographs of Jurkat T cells (A) and unshocked control cells (B) exposed to pulsed electric fields (20 nanoseconds, 20 kV/cm) showing intracellular effects of fields.
Figure 8B:
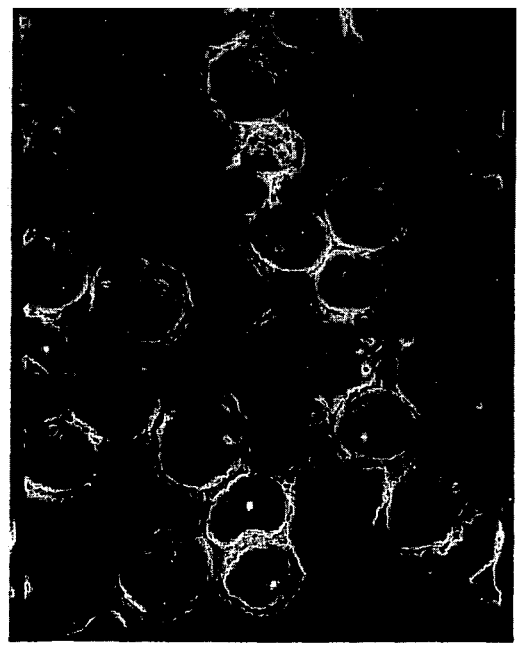

Intracellular effects are caused by the application of relatively short, relatively intense electrical pulses (on the order of about 10 kV/cm or more, measured macroscopically across cuvette electrodes, for times on the order of about 20 nanoseconds or less). A photograph of one study is shown in FIG. 8. Genomic, proteomic and subcellular biochemical studies show, from biophotonic studies and global DNA microarray analysis, that the fields thus applied either activate or inactivate specific genetic pathways located in the intracellular compartments.

Specific intracellular effects, including, but not limited to apoptosis, are also caused by the application of relatively short, relatively intense electrical pulses (typically about 20 nanoseconds or less). Biological experiments on human cells showed that these applied fields (1) led to and altered the subcellular and metabolic biochemical pathways; (2) either activated or inactivated a subset of genes, and (3) could be investigated using biophotonic studies for imaging of morphological and functional changes at subcellular levels. Specific intracellular effects of non-ionizing sources, ranging from transcription of targeted genes to the translation of gene products and protein modifications, also occurred.

The ultrashort pulse exposures described herein were performed in physiological media, permitting direct observation of the effects of electric pulse perturbations in normal, respiring, viable cultured cells. The approach described herein provides a platform for investigations at sub-cellular levels. The results provide an improved understanding of physiological responses of cells, tissues, and organs. Also, this approach facilitates fundamental investigations of internal membrane and cytoskeletal biophysics and biochemistry and allows selective stimulation of subsets of cell populations in physiologically significant ways.

In accordance with several embodiments of the current invention, UPSET is used as a tool for triggering apoptosis and provides a method of selectively disabling tumor or other undesirable cells. Many biochemical and genetic inducers, inhibitors, and modulators of apoptosis are known, and embodiments of the present invention provide a non-contact, non-invasive switch for directing rapidly dividing cells towards programmed cell death or altered gene expression without the intervention of pharmacological or genetic agents.

Clinical Applications

The effects of UPSET technology affects and its selectivity for certain tumors, such as glioma brain tumors, have significant clinical applications. Current treatment strategies for patients with brain cancer are ineffective. In 1999, malignant glioma, the most common primary cancer of the central nervous system (CNS), was the cause of death in approximately 13,100 people (DeAngelis, M. 2001. Brain Tumors New England Journal of Medicine 344:114-123). Despite aggressive therapy, including surgical resection, irradiation and chemotherapy, a diagnosis of a malignant glioma is uniformly fatal with survival typically measured in months. The therapeutic efficacy of stereotactic radiosurgery for treatment of patients with both primary and metastatic brain cancer is currently the focus of intense clinical investigation. In developing alternative therapies for brain cancer, several important principles apply. New therapeutic approaches should be targeted directly to the tumor to minimize local toxicity. Drug delivery or gene transfer into the CNS should take into account the blood brain barrier or bypass it.

The field of clinical neurosurgery is rapidly evolving. One of the most promising advances is in the field of "functional neurosurgery." For instance, the therapeutic application of deep brain stimulation for the treatment of Parkinson's Disease is an important example of how stimulating microelectrodes are stereotactically placed within critical structures deep within the brain such as the basal ganglia and thalamus to interrupt motor circuit pathways to influence tremor and rigidity seen in this disorder. In accordance with several embodiments of the current invention, UPSET-based microelectrodes can be stereotactically placed into regions of the brain to provide a minimally invasive, targeted strategy. In this manner, a wide range of CNS disorders may be diagnosed and/or treated.

Identification of hallmarks of apoptosis, or programmed cell death, and a rapid induction of a subset of critical transcriptional immediate early regulatory genes, by the application of intense pulsed electric fields of very short duration (e.g., on the order of about tens of nanoseconds or less) are provided in several embodiments of the present invention. These fields perturbed mitochondrial membranes and the compartmentalized intracellular environment of Jurkat T lymphocytes. Phosphatidylserine translocated to the external face of the lipid bilayer within minutes after exposure, followed by caspase activation and the appearance of poly (ADP-ribose) polymerase fragmentation. Pulsed fields of high instantaneous power, but low total energy, penetrated the cell, invoked mechanisms associated with apoptosis, and offered a pathway for activating organelles and targeting specific genes associated with malignant cells.

The up-regulation of a small group of genes in Jurkat T cells by relatively intense electric fields applied for relatively short times is provided herein. Additional intracellular effects, including, but not limited to, electric field-induced apoptosis, or programmed cell death, are also provided. The fields were tailored to match dielectric properties of the cells in such a way that they caused fields to appear and produce effects inside of the cells. The diagnostics included testing for Annexin V binding, caspase activation, mitochondria membrane permeation and a global DNA microarray analysis of gene regulation. The pulses were typically of relatively short duration, e.g. on the order of about tens of nanoseconds or less. The electric fields perturbed intracellular elements, such as the mitochondria. Further perturbative effects influenced processes at sites within cells, i.e., those involving distinct transcription of RNA transition proteins. Such electroperturbative effects offer a pathway for fundamental investigations of internal cell biophysics and have applications in malignant cells therapy.

To calculate the electrical response of a cell to a fast-rising, or short electrical pulse, phenomenological data for cell dielectric properties were incorporated as parameters into a lumped electrical circuit model for a cell. FIG. 1 shows that high frequency, or more precisely, fast-rising pulsed electrical fields introduced electric fields into the intracellular media of mammalian cells.

Figure 1A:
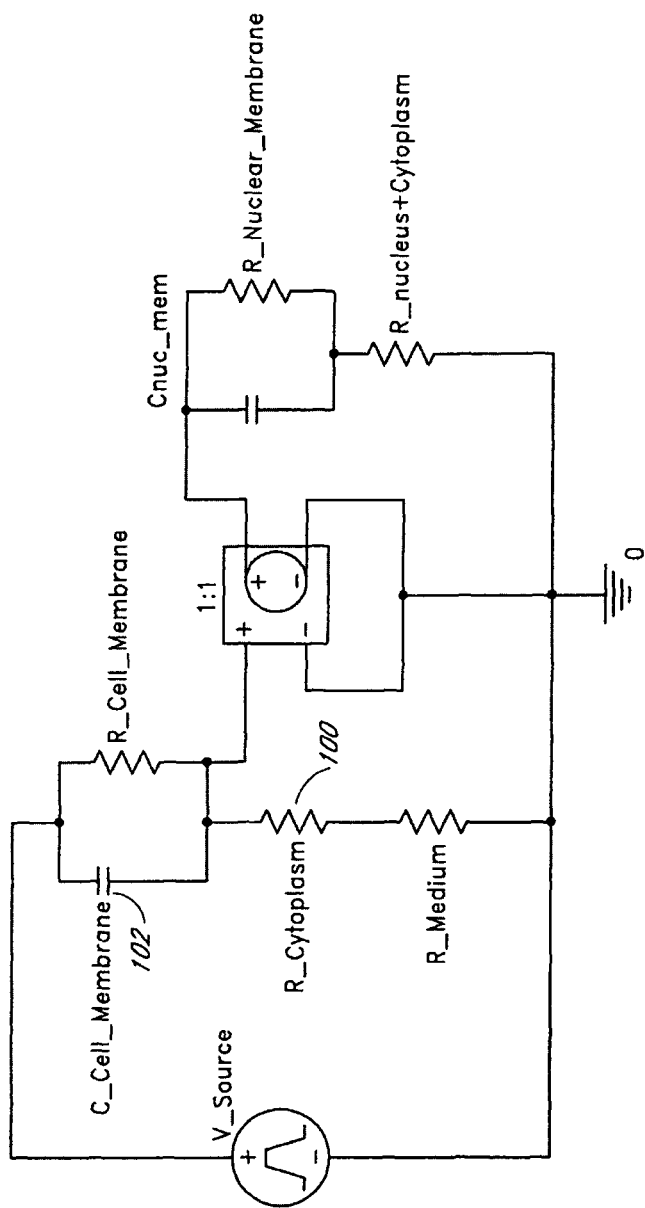
FIG. 1A shows a phenomenological lumped element circuit model of a biological cell containing a single organelle, representing the membrane of the organelle and the cytoplasmic membrane as separate capacitors, facilitating fast-rising pulses to conduct through the smaller capacitance of the nucleus (or other organelle or structure).

FIG. 1A shows a lumped circuit model of the cell. Circuit parameters for the distribution of current flow for cell membranes are estimated using values from the literature (See, for example Kotnik, T., and D. Miklavcic, Bioelectromagnetics 21:385-394 (2000), herein incorporated by reference). For these studies, an intracellular organelle was modeled as a small sphere (compared to cell radius) surrounded by a dielectric membrane, typically relative dielectric constant of 4 and a thickness of 5 nm. Other processes, such as thermal effects on induction of apoptosis, can modify the cellular physiology, or can become a dominant factor in determining the consequences of electric fields on cell behavior. However, the lumped model circuit provided a clear indication of conditions (pulse width, amplitude) under which field will perturb organelles within the cell.

Electromagnetic Calculations: MAGIC Software

In several embodiments of the current invention, MAGIC software for electromagnetic calculations in the presence of conductive media (available from Mission Research Corp.) was used to develop an electromagnetic model with more detail than a lumped circuit element model. MAGIC software is particularly advantageous because it uses a finite difference time domain method, has the advantage of flexibility and a well-documented code, and is suitable for defining the material properties. However, one skilled in the art will understand that other types of electromagnetic calculation software can also be used in accordance with several methods of the current invention. The effects of the larger intracellular structures on the field distribution were modeled using simulations with different sizes of mitochondrion membrane to compare differences between the more sophisticated simulation and the circuit model.

Figure 1B:
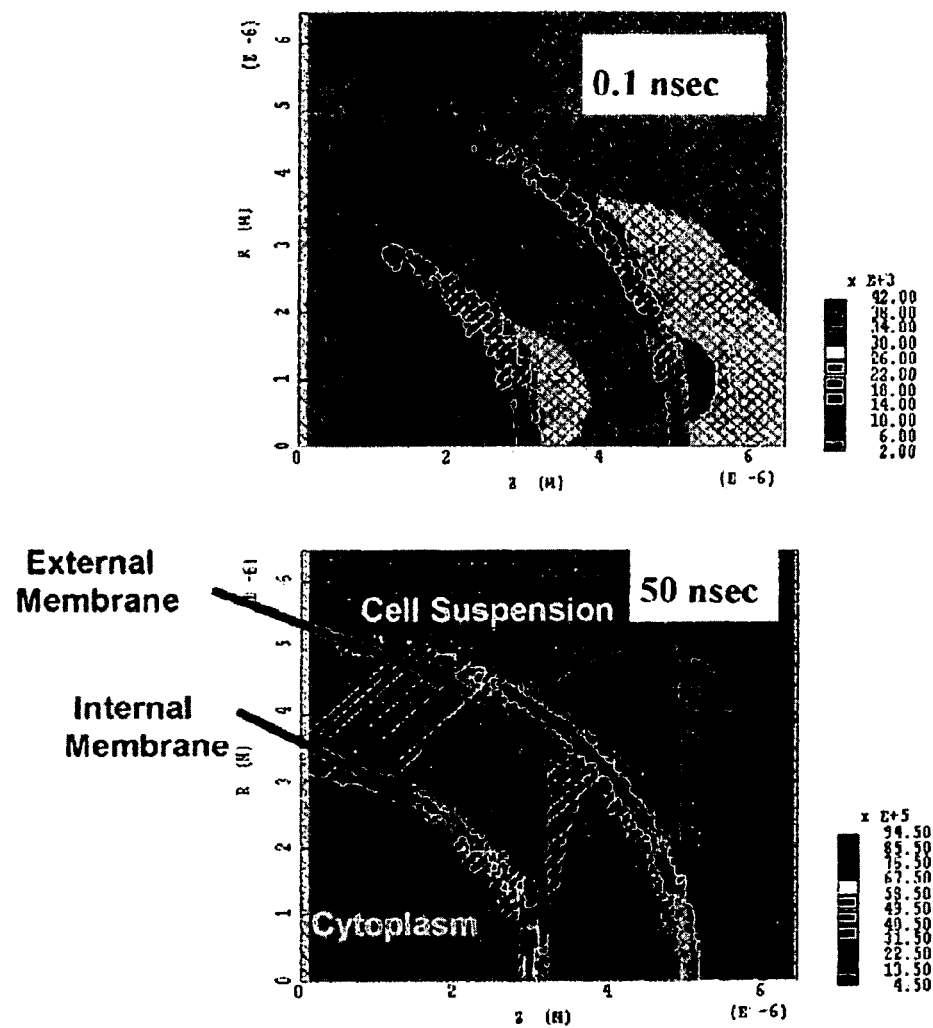
FIG. 1B shows a 2-Dimensional electromagnetic model for cell membranes demonstrating the effect of the short pulse on interior membrane. At the early stages of a voltage pulse, the voltage (Electric field) is dropped across a resistor 100 (Cytoplasm), and at steady state condition the voltage (Electric field) is dropped across a 102 capacitor (Membrane).

FIG. 1B shows a MAGIC 2-Dimensional electromagnetic model for cell membranes demonstrating the effect of the short pulse on the interior membrane. A spherical cell is modeled in cylindrical coordinates with axial symmetry. Electric field line distribution around and through the cell at 10 nanoseconds after applying a 20 Kv/cm electric pulse to the cell is also shown in FIG. 1B. The Upper Plot shows contour plots of electric field 1 nanosecond after applying the electric pulse for the dotted area in the left of the FIG. Each shaded area in the FIG. shows locations where the electric field has the same magnitude. The nonuniformity of electric field inside the cell due to the relatively large nuclear area, and the relatively smaller electric field magnitude across the membranes at the early stages of applying the pulse, which shows that the capacitive membranes are not initially charged and almost no electric field is across these membranes. The lower plot shows an electric field 50 nanoseconds after applying the pulse. A large electric field exists across these internal membranes, much smaller electric field within the cytoplasm of the cell. This is similar to the behavior of an RC circuit. At the early stages of a voltage pulse, the voltage (Electric field) is dropped across the resistor (Cytoplasm), and at steady state condition the voltage (Electric field) is dropped across the capacitor (membrane).

FIG. 1B shows the results and a comparison of the voltage across the nucleus membrane from the two approaches for a step pulse with 1 picosecond rise time and 160 V peak voltage applied to the cell. These results show that including the geometric effects not present in the circuit model increases the electric field predictions in the interior membrane by approximately a factor of two. Both approaches support the conclusion that significant electric fields appear across intracellular membranes for pulses that are sufficiently short (on the order of about 20 nanoseconds or less).

Pulse generator characteristics were taken into account, as the pulse duration and amplitude are in ranges that typically require specialized pulse generation equipment. This is because the pulse characteristics require that the design of the pulse generator, matching of transmission line, and matching to the load (typically a cuvette with conductive solution containing cells with dielectric properties), must be engineered to match with these pulse shapes and pulse characteristics. A MOSFET-switched, inductive-adding pulse generator, using a balanced, coaxial-cable pulse-forming network and spark-gap switch for pulse shortening, was used. The pulse generators delivered electrical pulses to biological material in a variety of exposure modes, including, but not limited to, single-cell, detached-cell suspensions, and layers of cells in culture. The inductive adding pulse generator allowed application of the short pulses (typically about 5-10 kV and about 20 nanoseconds), thereby providing large amplitude electric fields at the electrical load (e.g., within the cuvette).

Experimental Conditions with Jurkat Human T-Lymphoblasts and Gene Transcription

Jurkat human T-lymphoblasts were used in accordance with several embodiments of the current invention. However, one skilled in the art will understand that other cell types can also be used, including but not limited to NIH 3T3, Y79 or Weri-RB1 retinoblastoma, gliomas, COS7, hepatocytes, etc. Human cells are used in accordance with several embodiments of the current invention. However, one skilled in the art will understand that any cell type can be used, including non-human cell types. In one embodiment, UPSET is used to treat bacteria and toxins. In another embodiment, pulsed electric fields are applied to pathogens in food. In a further embodiment, UPSET is used in veterinary applications. In yet another embodiment, UPSET is used to treat spores, including, but not limited to, Anthrax.

Jurkat human T-lymphoblasts were maintained in suspension culture for these studies (Weiss A, Wiskocil, R L, Stobo J D. J. Immunol. 133:123-128 (1984)) herein incorporated by reference). The Jurkat cells were obtained from American Type Tissue Culture, Rockville, Md. The Jurkat human T-lymphoblast cells were maintained in suspension culture in RPMI 1640 medium, supplemented with 10% fetal bovine serum (FBS), 2 mM L-glutamine, 100 U/ml penicillin and 100 µg/ml streptomycin (growth medium) at 37° C. in an atmosphere containing 5% CO2. Cells were seeded at $5 \times 10^5$ cells/ml in fresh medium the day before the experiment. Cells were harvested by centrifuging at 1,000 rpm for 3 min and resuspended in growth medium to a final concentration of $2 \times 10^7$ cells/ml. Aliquots of 100 µl of cell suspensions were transferred into standard 1-mm gap electroporation cuvettes. After shocking, the cells were transferred into 6-well tissue culture plates, diluted with RPMI medium to a final concentration of $1 \times 10^6$ cells/ml and incubated at 37° C. Aliquots of cell suspensions were taken at 0, 1, 2, 5, 8 and 24 hrs after shock for Trypan Blue exclusion/cell counting, Annexin V binding-Propidium iodide (PI) penetration assay, JC-1 staining and PARP cleavage assays. As a positive control for induction of apoptosis, apoptotic cells were treated with 0.0075% Triton X-100, which has been shown to induce apoptosis in a variety of cell lines (Borner M W, Schneider E, Pirnia F, Sartor O, Trepel J P, Myers C E, FEBS Lett. 353:129-132 (1994), herein incorporated by reference). Rectangular electroporation cuvettes with 1 millimeter and 4 millimeter electrode separations were used to shock dispersed cells in a defined culture media. The cuvette volumes were 75 to several hundred microliters, cell suspension, with cell concentrations up to $2 \times 10^7$ cells per milliliter.

Figure 2A:
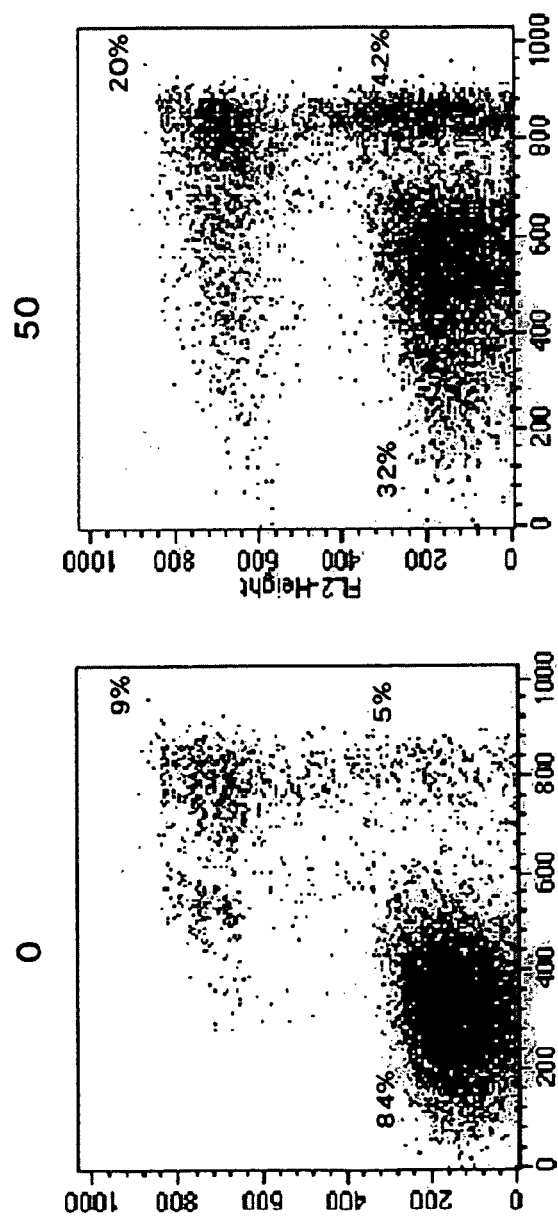
FIG. 2A shows Annexin V-FITC and PI flow cytometry data showing induction of apoptosis by 50 repetitive 20 nanoseconds, 40 kV/cm pulsed electrical shock as measured by Annexin V-FITC and PI staining of the shocked (50 pulses) and unshocked (0 pulse) cells at 8 hrs after the shock treatment, where the percentage of cells in the nonapoptotic (lower left), early apoptotic (lower right), and late apoptotic (upper right) quadrants is indicated.

FIG. 2A shows Annexin V-FITC and PI flow cytometry data showing induction of apoptosis by 50 repetitive 20 nanoseconds, 40 kV/cm pulsed electrical shock as measured by Annexin V-FITC and PI staining of the shocked (50 pulses) and unshocked (0 pulse) cells at 8 hrs after the shock treatment, where the percentage of cells in the nonapoptotic (lower left), early apoptotic (lower right), and late apoptotic (upper right) quadrants is indicated. The Annexin V-FITC apoptosis detection kit I (BD PharMingen) was used to identify apoptotic cells. For each assay$\approx 4 \times 10^5$ cells (400 µl of cell suspension) were transferred from 6-well plates containing the treated cells into microcentrifuge tubes, washed once with cold PBS (200 g, 3 min) and resuspended in 300 µl of binding buffer. One hundred microliters of resuspended cells was transferred into a culture tube and 10 µl combined Annexin-V-PI solution was added. Samples were incubated in the dark for 15 min at room temperature, and 400 µl of binding buffer was added to each tube. Samples were then analyzed by flow cytometry within 1 hr.

Figure 28:
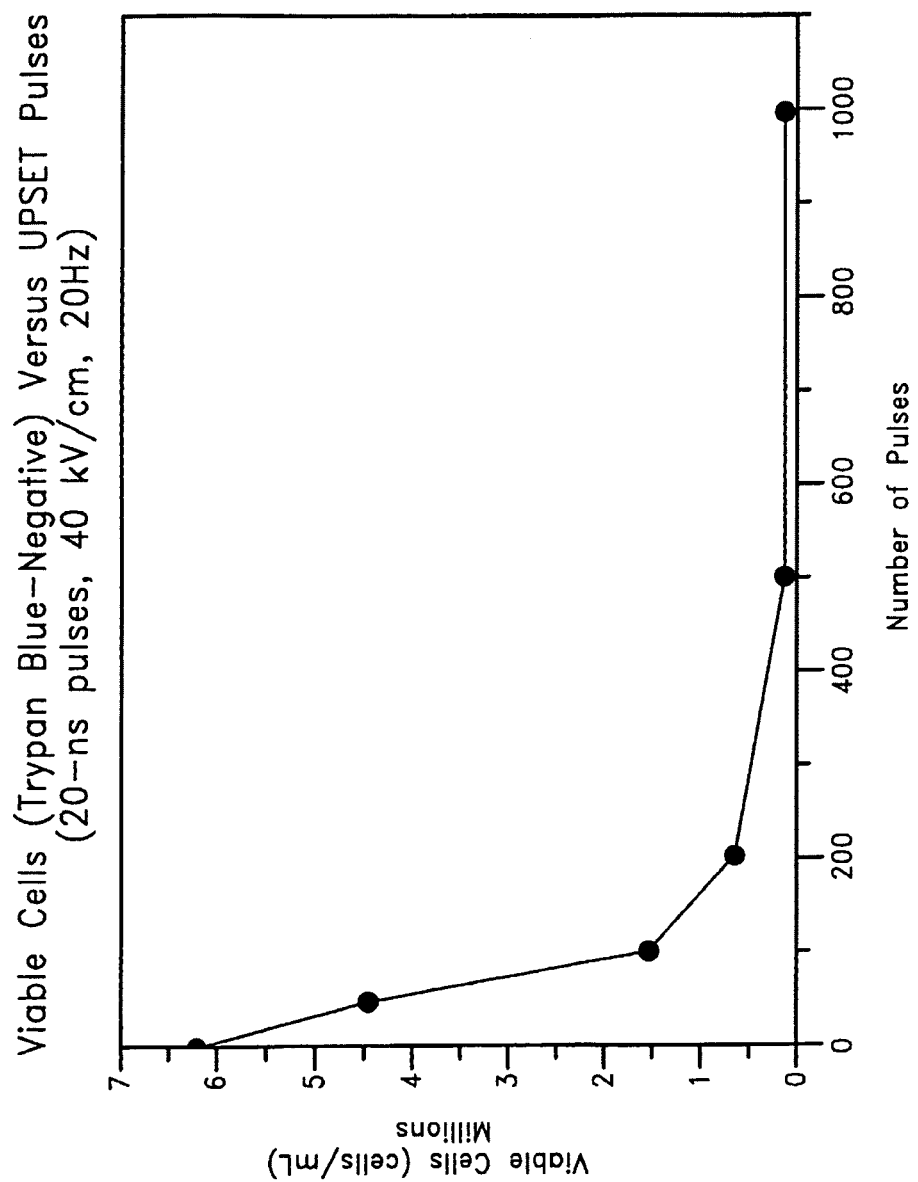
FIG. 28 is a graphical representation of Jurkat T cell viability after hundreds of UPSET pulses.
Figure 29:
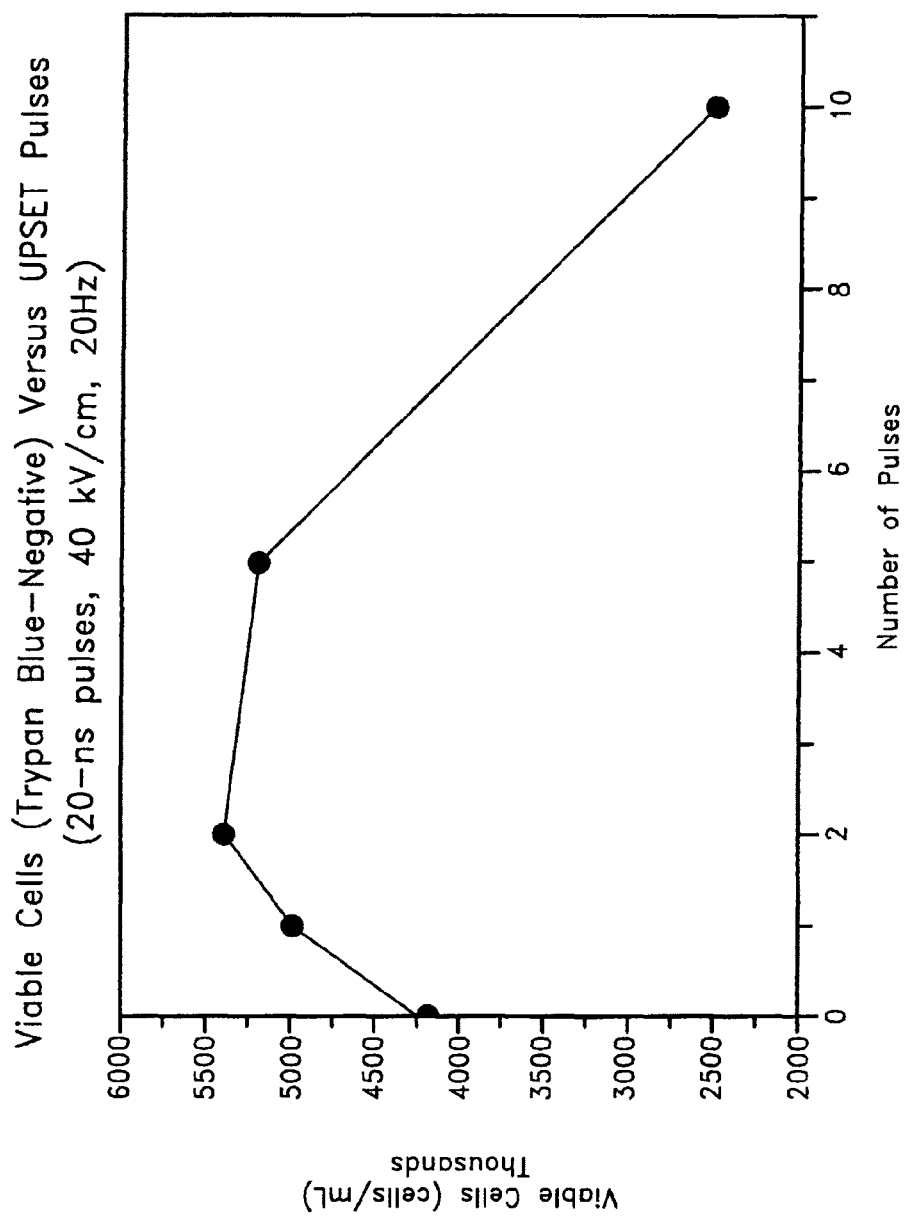
FIG. 29 is a graphical representation of Jurkat T cell viability after only a relatively small number of UPSET pulses.

Apoptosis induction was confirmed by immunoblot analysis of Poly-ADP-ribose-polymerase (PARP) cleavage in a series of 8-, 20- and 50-shock samples at 5 and 24 hrs after shock (FIG. 2). Trypan blue exclusion experiments verified that the plasma membranes of the cells were lightly permeabilized by 20- and 50-shock treatments, with the 50-shock treatment having a relatively stronger effect. The data from these tests are summarized in FIG. 2 (A-E). The cells were stained and inspected using an inverted microscope and Trypan blue. For comparison, normal cells were not stained. The stained cells reflect the uptake of dye due to a permeable outer membrane while normal live cells appear highly illuminated with clearly defined edges. Most of the cells in the 50-shock samples were enlarged and lightly stained with Trypan blue at 0 hr after shock, but this morphological change and the permeabilization to Trypan blue were reversible and totally recovered at about 2 hrs after shock. FIG. 28 shows Jurkat T cell viability after hundreds of UPSET pulses. FIG. 29 is a graphical representation of Jurkat T cell viability after only a relatively small number of UPSET pulses.

Figure 3:
FIG. 3 is an immunoblot PVDF membrane analysis of proteins resolved on SDS-polyacrylamide electrophoresis (SDS-PAGE) that identifies the immunoreactive Poly-ADP-ribose-polymerase (PARP) cleavage in response to electric shock and triton X-100 (TX) treatments.

FIG. 3 shows an immunoblot analysis of immunoreactive Poly-ADP-ribose-polymerase (PARP) cleavage in response to electric shock and Triton X-100 (TX) treatments. The decrease in the quantity of native form of PARP (113 kDa)

and the increase in its proteolytic cleavage products (89 kDa) are characteristic of apoptosis. Poly-ADP-ribose-polymerase (PARP), a 113-kDa DNA binding protein, is cleaved into 89- and 24-kDa fragments during apoptosis, which serves as an early specific marker of apoptosis. An anti-PARP polyclonal antibody (Roche Molecular Pharmaceuticals) was used to detect the cleavage of the 113-kDa PARP immunoreactive protein. Cells (5×105) were collected from the 6-well plates, 5 and 24 hrs after the shock treatments, washed with PBS, and sonicated 1 second×10 on ice in 100 μl of PBS. Equal amounts (50 μg) of proteins from whole cell homogenates were electrophoresed on 11.5% sodium dodecal sulfate-polyacrylamide gel electrophoresis (SDS-PAGE) and were electrophoretically transferred to Immobilon-P membranes (Millipore, Bedford, Mass.) (Craft C M, Xu J, Slepak V Z, Zhan-Poe X, Zhu X, Brown B, and Lolley R N, Biochemistry 37:15758-15772, (1998), herein incorporated by reference). The immobilized proteins were detected with anti-PARP (1:1,000) followed with anti-rabbit secondary antibody, using an Enhanced Chemiluminescence Kit (Amersham).

Figure 30:
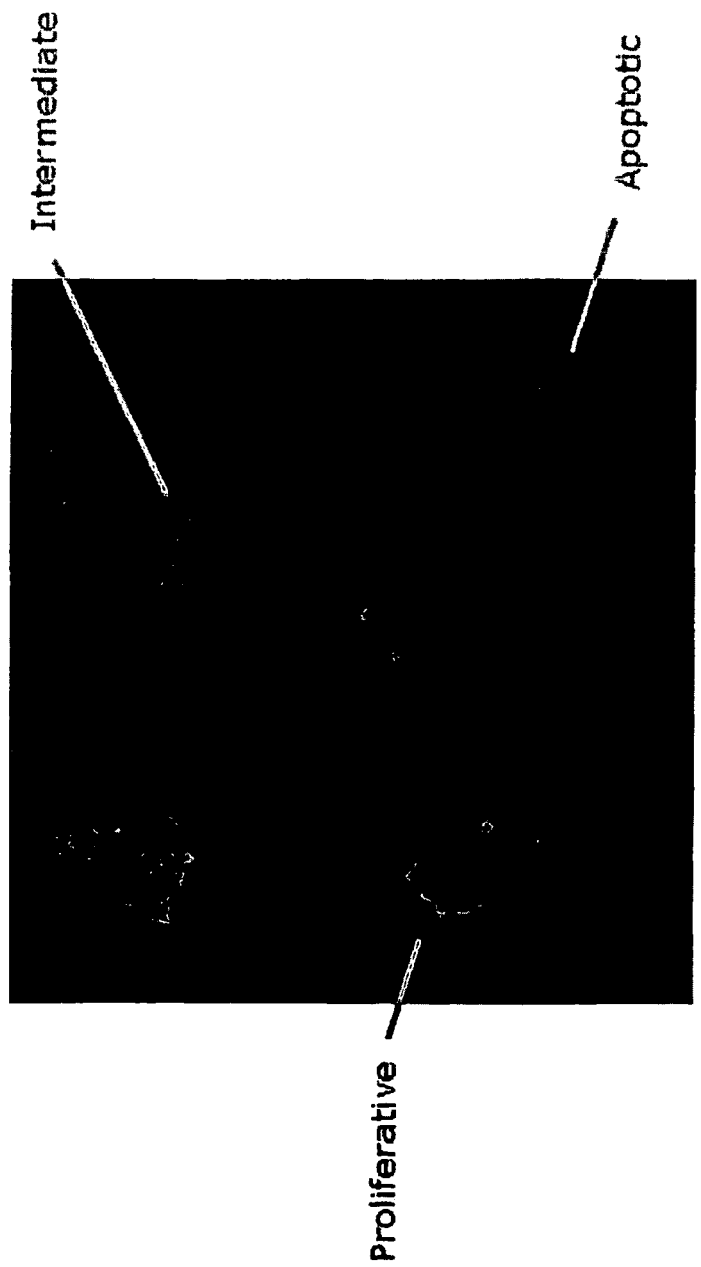
FIG. 30 shows the results of monitoring membrane potential of Jurkat T cells with JC-1.

Mitochondrial membrane potential was determined by JC-1 staining and flow cytometry analysis of the shocked and unshocked cells at 1 hr after shock (Cossarizza A, Salvioli S. Methods Cell Biol. 63:467-486, (2001), herein incorporated by reference). The 50-shock treatment caused mitochondrial membrane depolarization at 1 hr after shock. FIG. 30 shows the results of monitoring membrane potential of Jurkat T cells with JC-1.

Translocation of the membrane phospholipid phosphatidylserine (PS) and the associated degree of membrane permeabilization were measured by flow cytometric analysis of Annexin V-FITC binding and propidium iodide (PI) uptake using commercial reagents (FIG. 2).

Figure 2B:
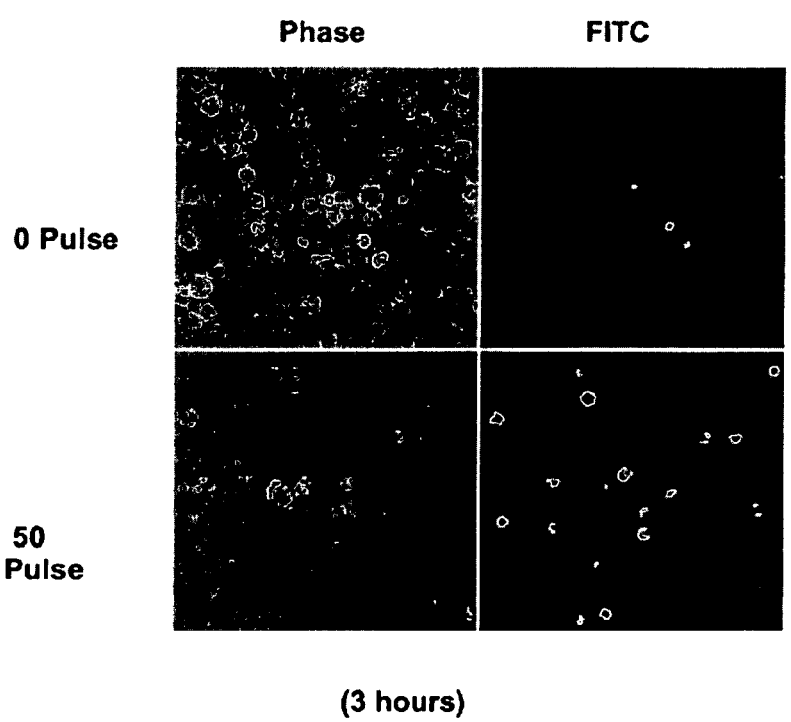
FIG. 2B shows fluorescent-tagged caspase substrate analog evidence 3 hours following pulse exposure for caspase activation after ultrashort pulsed electric field exposure.
Figure 31:
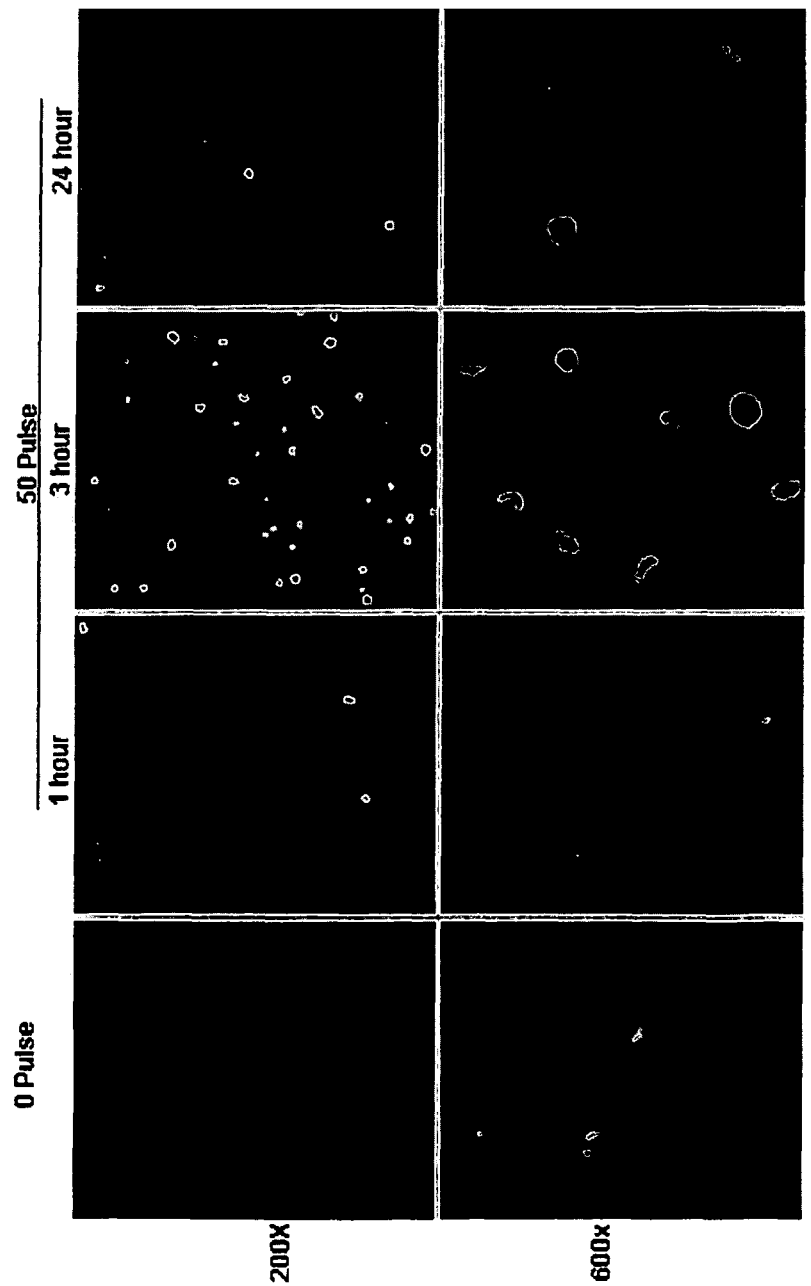
FIG. 31 shows the results of caspase activation in 50-pulse cells following FITC VAD-fmk binding, where the Jurkat T cells were electroperturbed with 20 nanosecond pulses at 20 kV/cm.

FIG. 2B shows fluorescent-tagged caspase substrate analog evidence 3 hours following pulse exposure for caspase activation after ultrashort pulsed electric field exposure. Caspase activation, a third apoptotic indicator, was demonstrated with specific binding of the fluorescent-tagged caspase inhibitor z-VAD-fmk. Morphological changes in the exposed cells, and their ability to exclude the dye Trypan Blue, were monitored with phase microscopy. The fluorescent-tagged caspase substrate analog, FITC-VAD-FMK, marks cells in which caspases, the effector enzymes of apoptosis, have been activated. Jurkat T cells were exposed in growth medium to 50 pulses (3-nanosecond rise time, 20-nanosecond width, 2-megavolt/meter amplitude, 20-hertz repetition rate) and incubated at 37° C. Fluorescence micrographs recorded one and five hours after exposure also showed the appearance of increasing numbers of caspase-positive cells in the shocked population with time. FIG. 31 shows the results of caspase activation in 50-pulse cells following FITC VAD-fmk binding, where the Jurkat T cells were electroperturbed with 20 nanosecond pulses at 20 kV/cm.

Figure 2C:
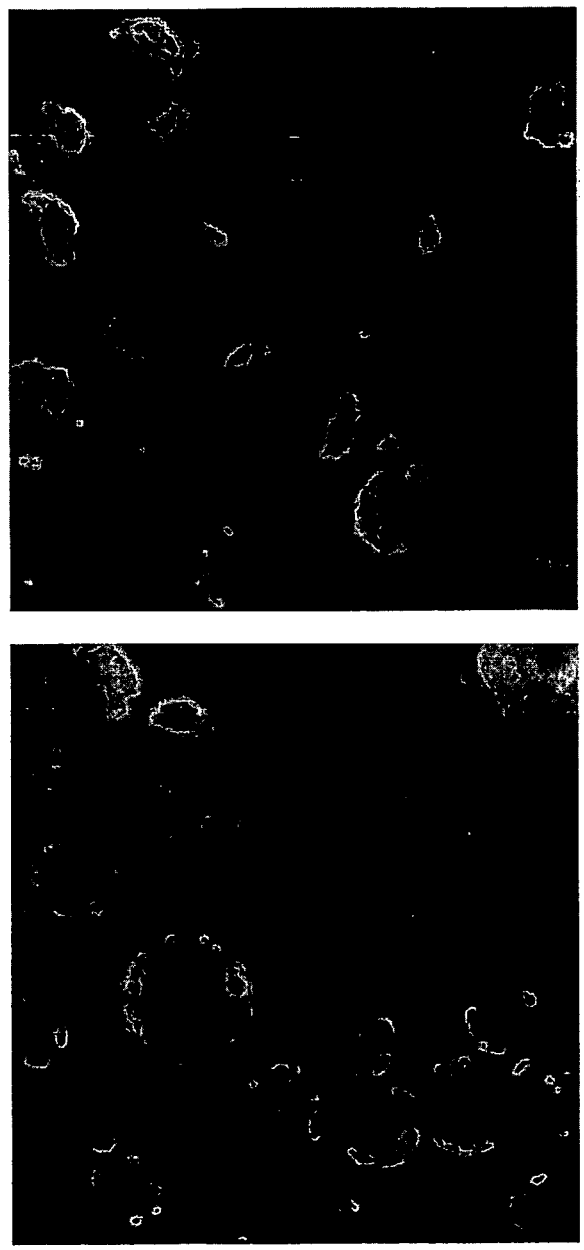
FIG. 2C shows evidence of loss of mitochondrial membrane potential, 3 hours after ultrashort pulsed electric field exposure.
Figure 2D:
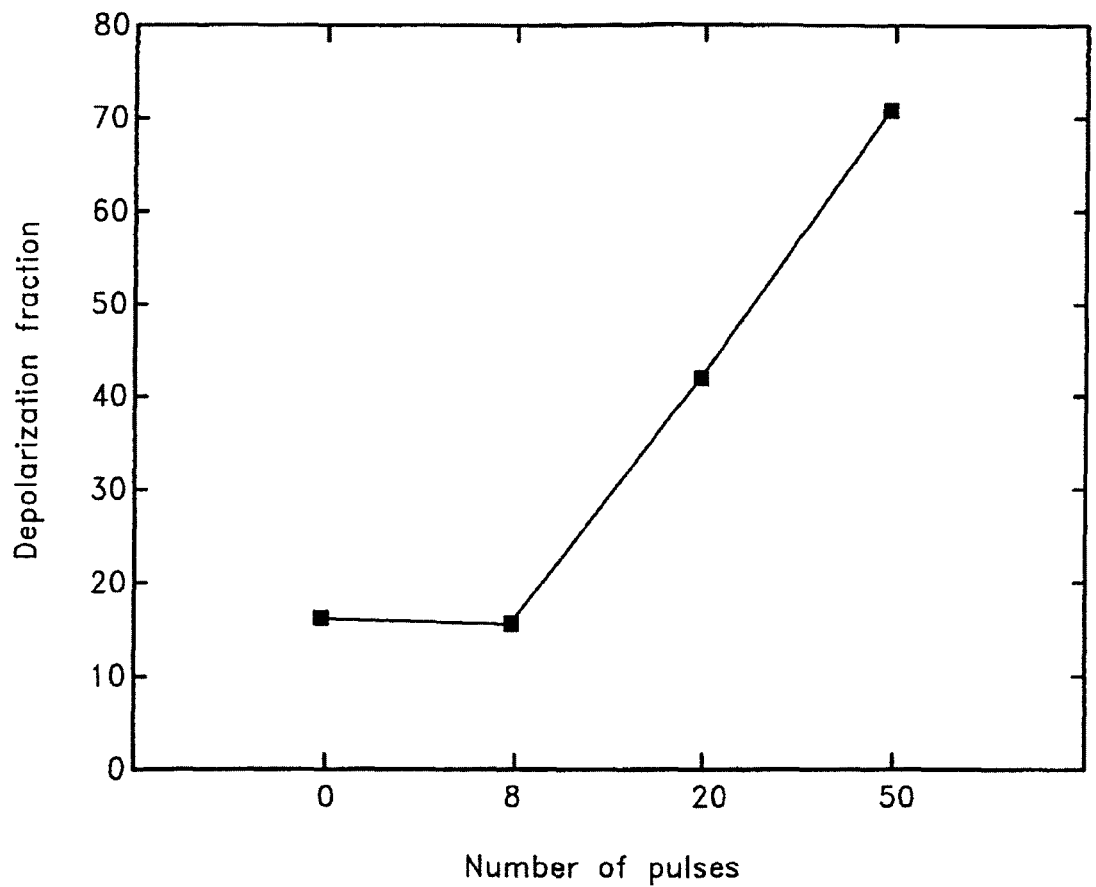
FIG. 2D shows flow cytometry analysis (JC-1 staining) showing increased mitochondrial membrane depolarization fraction as function of pulses with number of pulses (0, 8, 20 and 50 pulses) at 20 nanoseconds, 2 MV/m, 20 Hz.
Figure 2E:
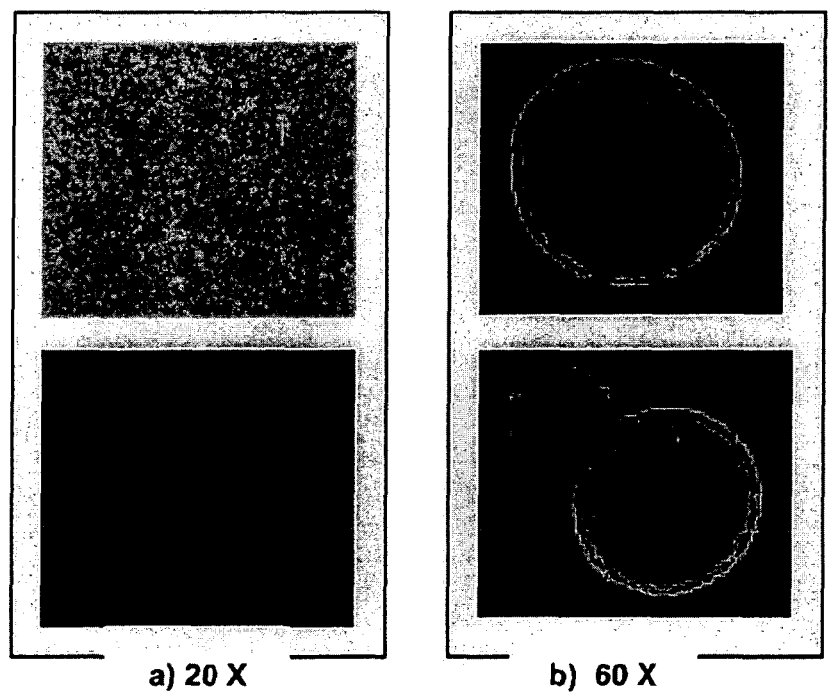
FIG. 2E shows an annexin V-FITC binding pattern on Jurkat T cells. The bottom figure a) is a control that is not fluorescing, and b) shows the results 0 to 5 minutes post-shock, with bright fluorescence.
Figure 32:
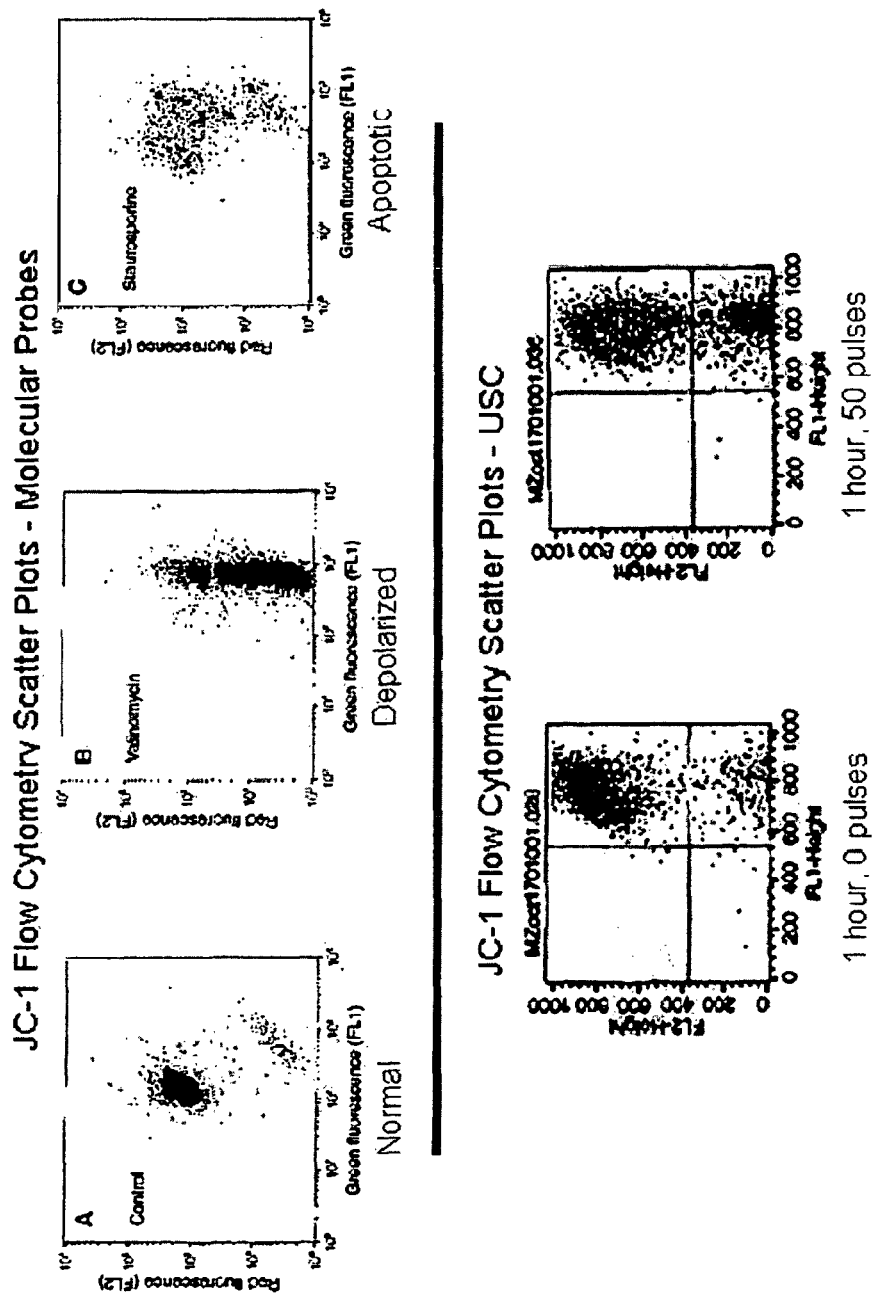
FIG. 32 shows JC-1 flow cytometry scatter plots for normal, depolarized, apoptotic, 0 pulsed, and 50-pulse cells.
Figure 33:
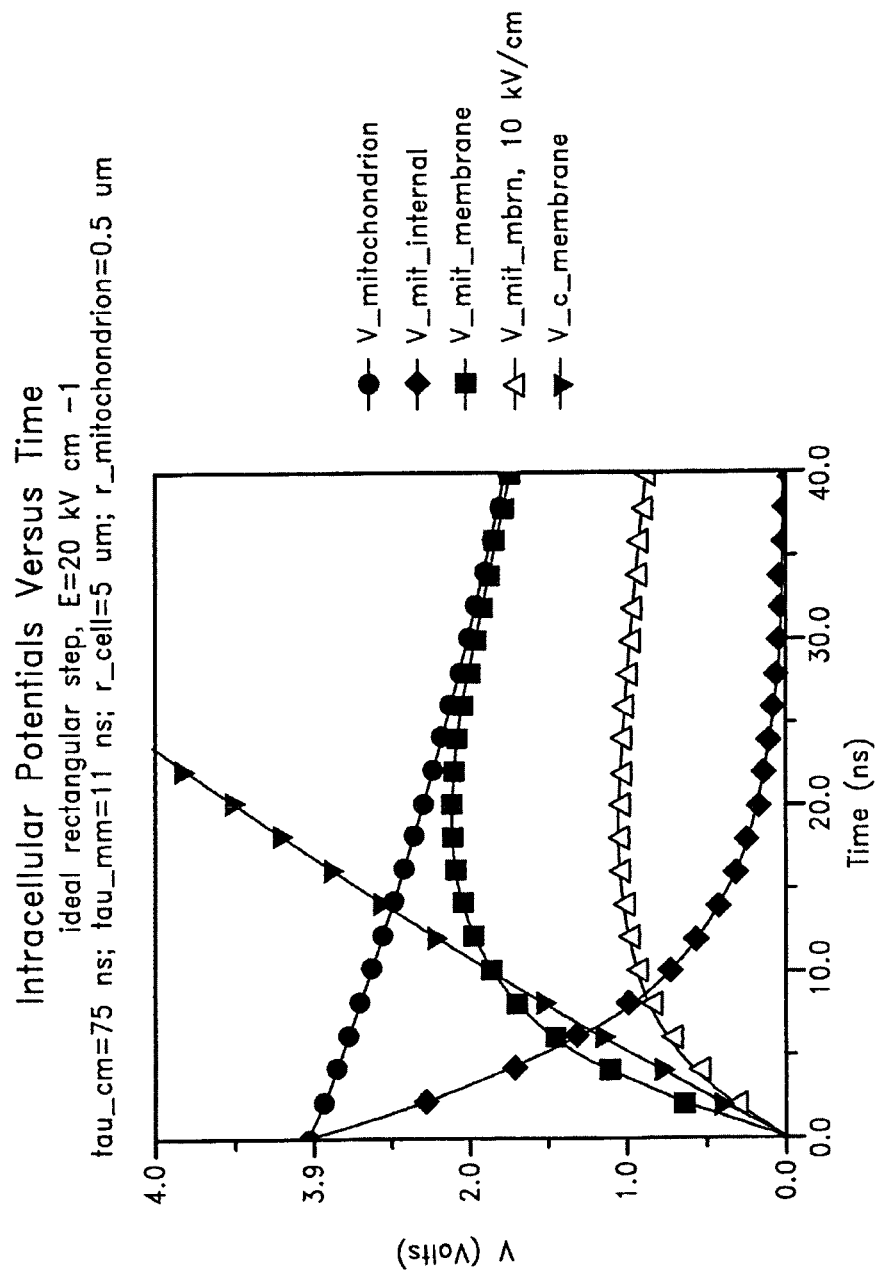
FIG. 33 is a graphical representation of intercellular potentials over time for cell and mitochondria and their respective membranes.

FIG. 2C shows evidence of loss of mitochondrial membrane potential, 3 hours after ultrashort pulsed electric field exposure. Fluorescence micrographs recorded three hours after exposure (excitation wavelength=436 nm, wideband emission) show a dose-dependent decrease in the punctuate, red fluorescence pattern. Similar results were observed 5 hours after shock. The potential-sensitive fluorochrome JC-1 (5,5',6,6'-tetrachloro-1,1',3,3'-tetraethylbenzimidazolylcarbocyanine iodide) binds to and forms red-fluorescing J-aggregates in normal, polarized mitochondrial membranes in living cells. A decrease in membrane potential reduces the affinity of the dye for the membrane and promotes formation of the cytosol-dispersed, green-fluorescing JC-1 monomer. Jurkat T cells were exposed in growth medium to 8, 20, and 50 pulses (3-nanosecond rise time, 20-nanosecond width, 2-megavolt/meter amplitude, 20-hertz repetition rate) and incubated at 37° C. A spectral shift was observed in the fluorescence of the mitochondrial membrane potential indicator JC-1. Shocked cells exhibited a shift from the red-fluorescing, J-aggregated, mitochondrial membrane-bound form of JC-1, to the green-fluorescing, monomeric form. This indicated the loss of mitochondrial membrane potential that typically accompanies apoptosis. FIG. 32 shows JC-1 flow cytometry scatter plots for normal (A), depolarized (B), apoptotic (C), 0 pulsed (D), and 50-pulse (E) cells. FIG. 33 is a graphical representation of intercellular potentials over time for cell and mitochondria and their respective membranes.

Affymetrix huGene FLTM array were hybridized with biotinylated in vitro transcription products (10 μg/chip) for 16 hrs at 45° C. using the manufacturer's hybridization buffer in a hybridization oven with constant rotation. The array then went through an automated staining/washing process using the Affymetrix fluidics station and was then scanned using the Affymetrix confocal laser scanner. The digitized image data were processed using the GeneChip software developed by Affymetrix. Hybridization on a microarray was performed as follows. Affymetrix huGene FLTM arrays (Santa Clara, Calif.) containing 6800 genes were used for mRNA expression profiling. Total RNA was isolated from Jurkat T cells treated with ultra-short electric shocks as described above. The cells were incubated in RPMI growth medium at a concentration of 1×106 cells/ml at 37° C. for 6 hrs before harvesting for total RNA isolation. Double-stranded cDNAs were prepared using the Life Technologies Choice System and an oligo(dT)$_{24}$-anchored T7 primer. Biotinylated RNA was synthesized using the BioArray™ HighYield™ RNA Transcript Labeling Kit (Enzo Diagnostics, Inc. New York), following the manufacturer's instructions. In vitro transcription products were purified using the RNeasy Mini kit (Qiagen).

cDNA preparations from post-shock cell populations were also analyzed, showing clear genetic expression variation in shocked versus control cells.

B. UPSET-Induced Gene Transcriptional Changes

UPSET treatments altered the Jurkat cells' biochemical and morphological state and altered specific transcriptional pathways. Oligonucleotide array technologies (Affymetrix™) were used to monitor gene expression profiles in Jurkat cells treated with 0, 8 or 50 ultrashort, pulsed electric shocks. Established data analysis included algorithms that define up-regulated or down-regulated genes as those exhibiting more than a 2-fold difference of expression levels between shocked (8 or 50 shocks) and unshocked (0 shock) cells. Using this oligonucleotide array-based expression profiling technology, 73 genes were identified whose expression increased in response to UPSET exposure after 6 hrs. These genes, included, but were not limited to ITPKA, AHNAK, EMP3, ADORA2B, POU2AF1, AIM1, ATP1G1, ASNS, ETS2, CD45, VIM, TGIF, LAT, CLIC4, SLC7A5, ZFP36L2, RUNX1, SLC3A2, IFRD1, and PrP.

The first major subset of up-regulated genes that appeared at 1 hr after UPSET exposure is associated with the cellular stress response and apoptotic cell death machinery. Genes that showed enhanced expression included, but were not limited to:

i) the enzyme asparagine synthetase (ASNS);
ii) CHOP, also known as GADD153 (CHOP is induced in response to cellular stress. CHOP is involved in the process of apoptosis associated with endoplasmic reticulum (ER) stress; and
iii) CLIC4 (Over-expression of CLIC4 reduces mitochondrial membrane potential, releases cytochrome c into the cytoplasm, activates caspases, and induces apoptosis).

Mitochondria are key organelles that integrate apoptotic signals in damaged cells. Therefore, these data indicated that CLIC4, like Bax, Noxa, CHOP, participate in a stress-induced cell death pathway converging on mitochondria and can serve as a target to enhance cancer therapy through genetic or therapeutic interventions. Thus, although not wishing to be bound by the following theory, it is believed that UPSET triggers the cellular stress response indicated by increasing transcription of the AP-1 family of early gene transcription factors after only 1 hr of exposure. FIG. 4 and FIG. 6 list up-regulated genes in response to electric field pulses. FIG. 4A list genes up-regulated after 6 hours. FIG. 4B lists genes up-regulated after 1 hour. It is also believed that UPSET triggers a cellular response by down-regulating several genes. FIG. 5 and FIG. 7 list these down-regulated genes. These down-regulated genes, alone or in conjunction with the up-regulated genes, are believed to play a role in a cell death or anti-proliferation pathway.

Activation of a second specific set of genes after only 1 hr included, but were not limited to, genes encoding both immuno-response and immune cell activation mediators and related regulating factors. The observed up-regulated genes in this subset included, but were not limited to:
i) CD45 (Involved in maturation, activation, and migration of immune cells);
ii) CD53 (Mediates cell activation);
iii) p36 (LAT), CD58 (A co-stimulatory molecule—blocking CD58 or its ligand);
iv) CD2 (Affects activation of T cells); and
v) AICL (A new activation-induced antigen).

Other genes that were affected at one hour included FOS, FOSB, DUSP1, JUN, TOB2, GADD34, CLK1, HSPA1B, JUND, EGR1, CACNA1E, CD69, and ETR01.

Studies at 6 hours also were conducted. One skilled in the art will understand that the studies conducted at 6 hours can be performed in essentially the same manner as that described above for the 1 hour protocol. One skilled in the art will also understand that studies can also be performed at time intervals other than post 1 hour and post 6 hours after treatment.

In one embodiment of the current invention, UPSET elicited the cellular stress response through mRNA transcriptional increases of specific members of the AP-1 family of early gene transcription factors after 1 hr of exposure. These results, alone and combined with the data from the 6 hrs of exposure, showed that the endoplasmic reticulum stress-mediated cell apoptotic pathways are mechanisms for UPSET exposure.

UPSET exposure perturbs mitochondrial structures or other intracellular stress sensors. When stress signals are unable to rescue and protect the cells, the apoptotic pathway is the default. Although not wishing to be bound by the following theory, it is believed that both mitochondria and death receptor pathways contribute to the apoptosis induced by UPSET exposure. mRNA transcripts corresponding to the genes known to be involved in the induction of apoptosis, such as caspases 1, 2, 3, 6, 7, 8, 11, 12, and 14, showed no changes at the transcriptional level. Other genes, e.g., Bcl-2, Bcl-w, Bag, Bax, Bak, Bad, Bid, and others known to be pro-apoptotic or anti-apoptotic were also typically unchanged. This indicates that, in one embodiment of the current invention, the UPSET exposure was not a global induction of apoptosis, but rather induced programmed cell death through a selective, defined pathway.

The up-regulation of the stress-associated protein CHOP (C/EBP Homologous Protein [C/EBP=CCAAT/Enhancer Binding Protein]), also known as GADD153 (Growth Arrest and DNA-Damage-inducible) provides one mechanism for electric pulse-induced apoptosis. Although not wishing to be bound by this theory, it is believed that under endoplasmic reticulum stress, the transmembrane protein p90ATF6 is cleaved to p50ATF6 and translocated to the nucleus, where it binds to the endoplasmic reticulum stress-responsive element (ERSE) of the CHOP gene, which then activates CHOP transcription (Maytin, E. V., M. Ubeda, J. C. Lin, and J. F. Habener, Exp. Cell Res. 267:193-204, (2001); Gotoh, T., S. Oyadomari, K. Mori, and M. Mori, J. Biol. Chem. 277:12343-12350, (2002), all herein incorporated by reference). CHOP, in turn, induces apoptosis.

Specifically, genes that were increased demonstrate that the pulse amplitude, using UPSET technology with nanosecond high field pulses to target the interior of cells, had dramatic and highly specific effects. These early response genes worked in concert to activate distinct DNA binding elements (e.g. AP-1), pushing rapidly dividing cells into a cell death pathway. This novel approach to targeting a rapidly dividing cell population, while protecting normal, nondividing or differentiated cell populations has many therapeutic applications. The nanosecond time resolution of UPSET exposures, and the striking and immediate physiological effects observed, provide productive applications of this tool to transcriptomic and proteomic studies. For example, the timing of early events in the apoptotic sequence, and the cause-and-effect relationships of a number of critical actors in apoptosis (caspase activation, cytochrome c release into the cytosol, the mitochondrial permeability transition, membrane phospholipid inversion, apoptosis-inducing factor) can be determined with the synchronization and uniformity of stimulus possible with UPSET treatments of single cells, cell suspensions, and tissues.

In one embodiment of the present invention, a method is provided in which tumors or other undesirable cells are disabled. Certain types of malignant cells, for example, are more sensitive than normal cells to a particular sequence of relatively ultrashort, relatively high-field pulses. This differential sensitivity has significant therapeutic applications. The subset of fewer than 50 significantly up-regulated genes from the 6800 examined is much fewer than is typical for chemotherapy treatments, which produce hundreds of varied regulated genes. Thus, UPSET treatment is a more selective form of "gene-modification therapy."

C. Pulsed-Power Technology and Instrumentation

In several embodiments of the current invention, pulsed power technology and instrumentation is provided. This pulsed power technology is used to develop practical electrodes, such as catheters for medical applications. Bioengineered pulsed power technology is particularly useful to specifically design both high field/short pulses in UPSET applications. For example, to apply a relatively high electric field to the biological cell, it is useful that the peak power at the load be relatively high, and that the design of pulse generator, transmission line, and coupling to the sample, whether solid tumor or individual cells. Existing electroporation devices cannot provide the relatively high field in a sufficiently short time. They typically turn on too slowly, due to limitations in circuitry, and basic switch properties.

In one embodiment of the present invention, MOSFET-driven, inductive-adding pulse generators using a balanced, coaxial-cable pulse-forming network and spark-gap switch were used for delivering electrical pulses to biological material for initial studies (FIG. 8). The initial UPSET experiments employed commercially available, rectangular electroporation cuvettes with 1- and 4-millimeter electrode separations to shock free-growing cells in growth medium. The cuvettes hold one hundred and eight hundred microliters of cell suspension, respectively, with cell concentrations up to $2 \times 10^7$ cells per milliliter. The pulse generator was designed and fabricated to allow fast rising high voltage pulses to be produced with solid state switches (I. Yampolsky and M. Gundersen, "Repetative power pulse generator with fast rising pulse" U.S. Pat. No. 6,831,377 filed May 3, 2001 and issued on Dec. 14, 2004g, herein incorporated by reference) and applied to the cuvettes and biological components.

MOSFET-Based Pulse Generators For High Field Applications

Figures 14A, 14B:
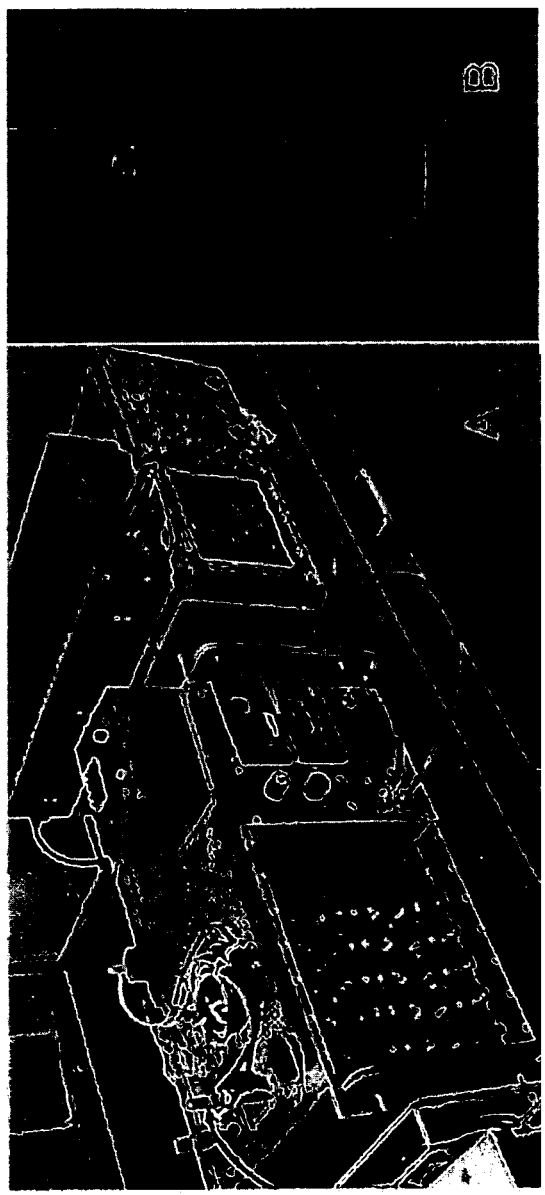
FIG. 14A shows an inductive adder pulse generator with a cuvette.
FIG. 14B shows a stand alone view of the cuvette.

In one embodiment of the current invention, a MOSFET-based pulse generator was used. FIG. 14A shows an example of a pulse generator known as an inductive adder based on MOSFETs. This adder produces over 40 kV with a 100 nanosecond pulse width and it has the advantage of having all input switches based at ground, reducing complexity of triggering, and alleviating the issue of series connections of the switches. This adder is particularly advantageous in applications where other switches are not practical.

Higher Power Pseudospark-Based Pulse Generation

In one embodiment of the current invention, a pseudospark-based pulse generator was used. This pulse generator, based on a pseudospark switch, operates in a less than about a 100 nanosecond pulse regime (FIG. 15), at a relatively high repetition rate, and a relatively high voltage. ("Low pressure, light initiated, glow discharge switch for high power applications," G. F. Kirkman and M. A. Gundersen, Appl. Phys. Lett. 49, 494 (1986); "High power pseudospark and BLT switches," K. Frank, E. Boggasch, J. Christiansen, A. Goertler, W. Hartmann, C. Kozlik, G. Kirkman, C. G. Braun, V. Dominic, M. A. Gundersen, H. Riege and G. Mechtersheimer, IEEE Trans. Plasma Science 16 (2), 317 (1988), all herein incorporated by reference). This combination, with an output impedance sufficiently low to match to the biological cuvette and transmission line, is particularly advantageous because it includes the following characteristics: i) high voltage; ii) fast rising (1 to few nanoseconds); iii) high repetition rate (to about 10 kHz); and iv) optimal impedance matching (range 20 to several hundred ohms). This provides repetition rates from 1 to 10,000 Hz, variable, and variable voltage.

Bioengineering of Advanced Pulsed-Power

For both laboratory and clinical applications, pulse generation for application of short pulses to the biological samples may be provided by, but not limited to, the following pulse generator types: 1) a MOSFET-based solid state pulse generator for higher voltages referred to as an inductive adder, 2) a minipulser, designed for cuvette experiments, and for experiments requiring close optical observation, 3) a more general purpose device based on an advanced gas phase switch (pseudospark), and 4) pulse generators designed for minimal size (Micropulser) for both therapeutic applications (incorporation into a catheter) and biophotonic studies (fitting into a microscopy system).

MOSFET-Based Inductive Adder

The inductive adder is a pulse generator technology especially suitable for high peak power applications requiring fast rising pulses. This system is particularly advantageous because it is highly efficient in producing a fast-rising high voltage, high current pulse, providing input switches in parallel which "add" the current.

High Voltage Nanosecond Pulse Generator Using Fast Recovery Diodes

Ultra-short, high-field strength electronic pulses may be used in the electroperturbation of biological cells. The voltage induced across a cell membrane may depend on the pulse length and pulse amplitude. Pulses longer than ~1 μs may charge the outer cell membrane and lead to opening pores, either temporarily or permanently.

Permanent openings may result in cell death. Pulses that are much shorter than ~1 μs can affect the cell interior without adversely affecting the outer cell membrane. Pulses lasting a few tens of nanoseconds and with a 2-10 MV/m amplitude may trigger apoptosis or programmed cell death.

Figure 34:
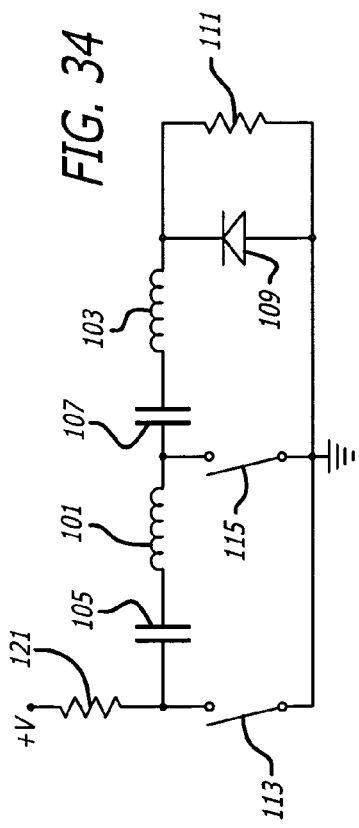
FIG. 34 is a simplified diode pulse generator.

FIG. 34 is a simplified diode pulse generator. As shown in FIG. 34, the diode pulse generator may include a tank circuit consisting of inductances 101 and 103 and capacitances 105 and 107. The tank circuit may be connected in series with a diode 109 across which a load to be driven 111 may be connected. The pulse generator may include a switching system, such as switches 113 and 115, which may be electronic. A voltage supply 119 may be connected to the diode pulse generator through a resistance 121.

Before the beginning of a pulse cycle, the switch 113 may be open and the switch 115 may be closed. This may cause the capacitance 105 to fully charge and the capacitance 107 to fully discharge.

At the beginning of the pulse cycle, the switch 113 may be closed and the switch 115 may be opened. This may cause charge to transfer from the capacitance 105 to the capacitance 107. During this transfer, the current through the tank circuit may rise and fall in approximately a sinusoidal manner.

This current may cause the diode 109 to be forward-biased as it travels travel through it. During this process, charge may be stored in the depletion layer of the diode 109.

At the end of the half-cycle, switch 115 may be closed. During the next half-cycle, the current flow may reverse in direction, causing the diode 109 to be reverse-biased. During the first part of the second half-cycle, current may still flow through the diode 109 while charge in its depletion layer is being depleted. Once the charge is depleted, the current through the diode 109 stops, causing the diode to appear as an open switch. This may cause the current through the inductance 103 to commute from the diode 109 to the load 111. The diode 109 may thus be configured to act as a opening switch, interrupting the current in the inductance 103 and commuting it into the load 111.

Current may now travel through the load 111 until the energy stored in the tank circuit consisting of the capacitance 107 and the inductance 103 depletes, thus delivering a pulse into the load 111.

The component values in the diode pulse generator shown in FIG. 34 may be selected so as to cause the charge in the diode 109 to be depleted at approximately the peak of the reverse bias current during the second half of the pulse cycle. When this occurs, the current through the load 111 is at maximum at the moment the diode 109 switches open, thus maximizing the peak voltage across the load 111.

To effectuate this peak timing, the capacitances 105 and 107 may be substantially the same and the inductances 101 and 103 may be substantially the same. This assumes an ideal circuit with ideal switches and lossless circuit elements. In a real circuit, adjustments to these values may be made to compensate, as will be discussed detail below in connection with FIG. 35.

As may now be apparent, the composition of the tank circuit that is shown in FIG. 34 changes as a function of the status of the switch 115. When the switch 115 is open, the tank circuit consists of the capacitances 105 and 107 and the inductances 101 and 103. When the switch 115 is closed, the tank circuit consists of the capacitance 107 and the inductance 103, but not the capacitance 105 and the inductance 101.

When the capacitances 105 and 107 are approximately equal and the inductances 103 and 101 are approximately equal, the resonant frequency of both tank circuit configurations may be substantially the same. Resonant frequency is a function of the product of the inductance and the capacitance. When the switch 115 is open, the total inductance is twice the inductance of the inductance 101 or 103 (assuming that the inductance 101 is about equal to the inductance 103), but the total capacitance is one-half of the capacitance of the capacitance 105 or 107 (assuming that the capacitance 105 and the capacitance 107 are about equal). Thus, the L-C time constant is equal to the capacitance 107 times the inductance 103.

When the switch 115 is closed, the L-C time constant is again equal to the capacitance 107 times the inductance 103. Thus, the closing of the switch 115 may not materially alter the resonant frequency of the tank circuit when the capacitances 105 and 107 are the same and the inductances 101 and 103 are the same.

On the other hand, the admittance of the tank circuit does change with the status of the switch 115. Admittance is a function of the square root of the capacitance divided by the inductance. When the switch 115 goes from open to close, the capacitance doubles and the inductance halves. Thus, the admittance of the tank in the diode pulse generator shown in FIG. 34 doubles when the switch 115 is closed. In turn, this causes the depletion layer in the diode 109 to discharge in the reverse-biased mode twice as fast as it took to charge in the forward-biased mode. If the diode 109 is never allowed to saturate when the diode is forward-biased, this may result in the depletion layer of the diode 109 being discharged at the moment the current in the second half of the cycle peaks.

The maximum output voltage of the diode pulse generator illustrated in FIG. 34 may be substantially equal to the peak current after the diode 109 has switched open, multiplied by the load 111.

The presence of the load 111 on the diode pulse generator shown in FIG. 34 may cause the magnitude of the pulse to the load 111 to decay to zero.

The switch 113 may be opened at any time after the switch 115 closes to initiate the second part of the cycle. This may cause the capacitance 105 to again charge in preparation for the next pulse that may be generated.

After the pulse to the load 111 decays, the switch 115 may be opened to ready the diode pulse generator shown in FIG. 34 to deliver the next pulse. After the charges have stabilized, the next cycle leading to the next pulse may be initialized by closing the switch 115, followed by the actions described above in connection with the first cycle.

In order to create extremely narrow pulses, the switch 115 may need to open and close very quickly. One approach to providing this fast switching speed is to use a saturable core transformer to serve as the switch 115.

Figure 35:
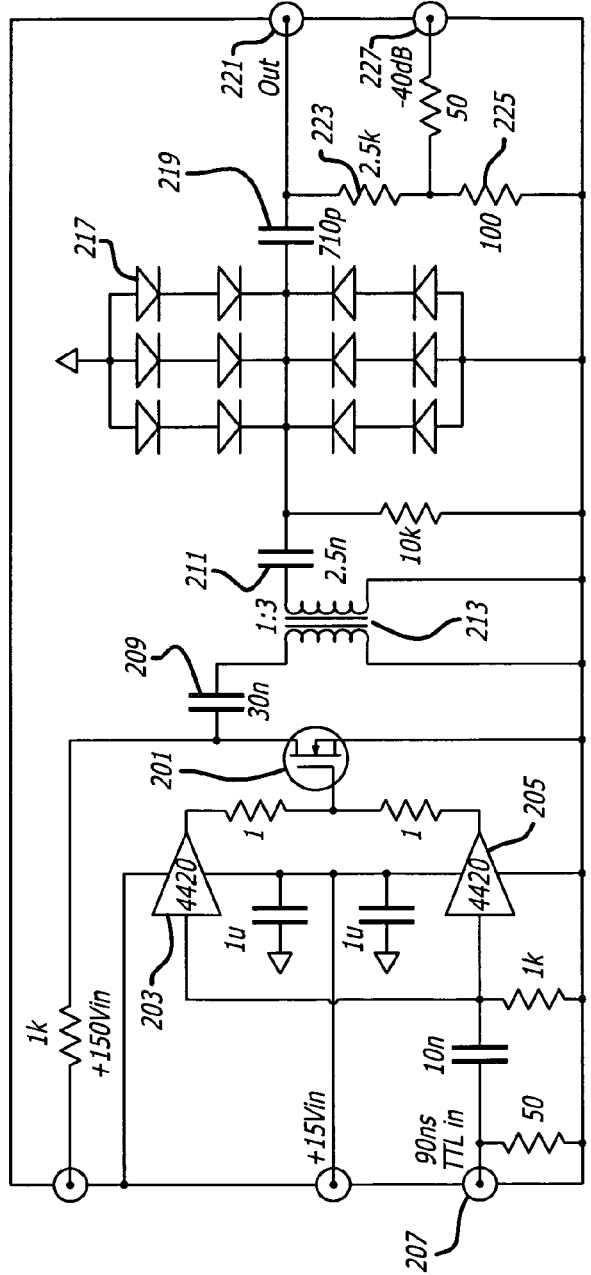
FIG. 35 is a diode pulse generator that utilizes a saturable core transformer.

FIG. 35 is a diode pulse generator that utilizes a saturable core transformer. The symbols and nomenclature that are shown in FIG. 35 are readily recognizable to the skilled artisan, thus obviating the need for a detailed description of every single component and connection. Instead, only selected areas of the circuit will be discussed.

As shown in FIG. 35, a MOSFET 201 may serve as the switch 113 shown in FIG. 34. This may be any type of MOSFET, such as an ATP 10035 JLL MOSFET.

The MOSFET 201 may be driven by a pair of drivers 203 and 205, such as an ON Semiconductor NCP4420, manufactured by Semiconductor Components Industries, LLC. The drivers may be triggered by the delivery of a pulse signal at an input 207. That input may be any type of signal, such as a 90 ns TTL pulse. This pulse may be repeated at a very high frequency.

A capacitance 209 in FIG. 35 may serve as the capacitance 105 in FIG. 34. Similarly, a capacitance 211 in FIG. 35 may serve as the capacitance 107 shown in FIG. 34. A saturable core transformer 213 may serve as the switch 115 shown in FIG. 34 and as the inductances 101 and 103 shown in FIG. 34. The capacitances 201 and 211 and the inherent inductances in the saturable core transformer 213 thus may serve as the tank circuit in FIG. 34.

In the absence of losses, the capacitance 209 may be substantially the same as the effective capacitance of the capacitance 211. The effective capacitance of the capacitance 211 my be its capacitance times the square of the ratio of turns in the saturable core transformer, which may be 1 to 3. Thus, the capacitance 211 may be equal to approximately nine times the capacitance 209 in a lossless system. In a practical system where there are losses, the value of the capacitance 209 may be larger to compensate, as reflected by the higher than nine-times value indicated in FIG. 35.

A diode array 217 may be used for the diode 109 shown in FIG. 34. The diode array 217 may consist of more than one diode in parallel and/or more than one diode in series. Connecting diodes in parallel may distribute the forward current across the diodes in the array, thus increasing the amount of time that current may be sent through the array before it becomes saturated. Connecting diodes in series may increase the amount of voltage that may be applied to the diodes when they are reverse-biased, thus allowing the output voltage of the pulse generator to be greater. The number of diodes that are placed in parallel and/or in series may be any number, so long as at least one diode is left. Using too may diodes may increase the capacitance of the circuit and slow its performance.

The diodes in the diode array 217 may be of any type, such as a MURS360, which is rated at 600 volts, 3 amps, and with a 75 ns reverse recovery time. One or more of the diodes may become saturated in less than 100 ns.

The saturable core transformer 213 may be configured to yield an energy storage inductance in its secondary winding that provides the needed fall time to achieve a desired output pulse width. The inductance current may decay as a function of the saturated secondary inductance of the transformer 213, divided by the load resistance that may be placed on an output 221. The minimum current that needs to be commuted into the load may be computed based on the desired peak output voltage, divided by the load resistance. The circuit may be designed to deliver an even higher output current to compensate for nonlinearities in the capacitance of the diode array 217, as well as other stray capacitances in the system.

The quarter period of the L-C circuit may be shorter than the diode recovery time to provide a fast current turn-off. A diode that is fully saturated with charge may delay its turn-off until after its recovery. As a consequence, the circuits shown in FIGS. 34 and 35 may be configured and operated such that the diodes do not saturate.

The fall time of the pulse that is delivered to the output 221 in the circuit shown in FIG. 35 may be shortened by the inclusion of a capacitance 219. A substantially attenuated version of the output may be generated by a resistor divider network, such as resistances 223 and 225, and delivered to an output test point 227.

The forward pumping current to the diode 109 may be equivalent to approximately π times the square root of the inductance 103 multiplied by the capacitance 107. The capacitance 107 may be selected so that this forward pumping current lasts for approximately half of the recovery time of the diode 109.

The saturable core transformer 213 may be wound on an amorphous core from Toshiba, type SA 14×8×4.5. The external cord dimensions may be: OD=16.3 mm, ID=6.3 mm, H=7.5 mm, and the effective core area $A_{core}$=10.3 mm². The core may support a flux swing of Φ=10.94 μWb and may saturate at $B_{sat}$=0.55 T. The inductance factor for intermediate frequencies may be $A_L$=3 μH/turn².

The core frequency response may not extend to the range that is actually being used. In this instance, the specifications set forth above may only be approximate. The inductance may be strongly frequency and excitation dependent, and the switching characteristics may be slower than what is necessary for efficient operation. Because of these issues, the transformer may be matched to the circuit by trial and error. Operation with the shortest output pulse at the full voltage rating of the diodes may be achieved with a 1:3 turns ratio. The primary may be a single turn of 16 awg solid copper wire and the second may be three turns of 20 awg solid copper wire evenly distribute around a toroid.

The circuit shown in FIG. 35 may generate a pulse length of no more than 3 nanoseconds at an amplitude of 1 kV and at a frequency of at least 100 kHz.

Figure 36:
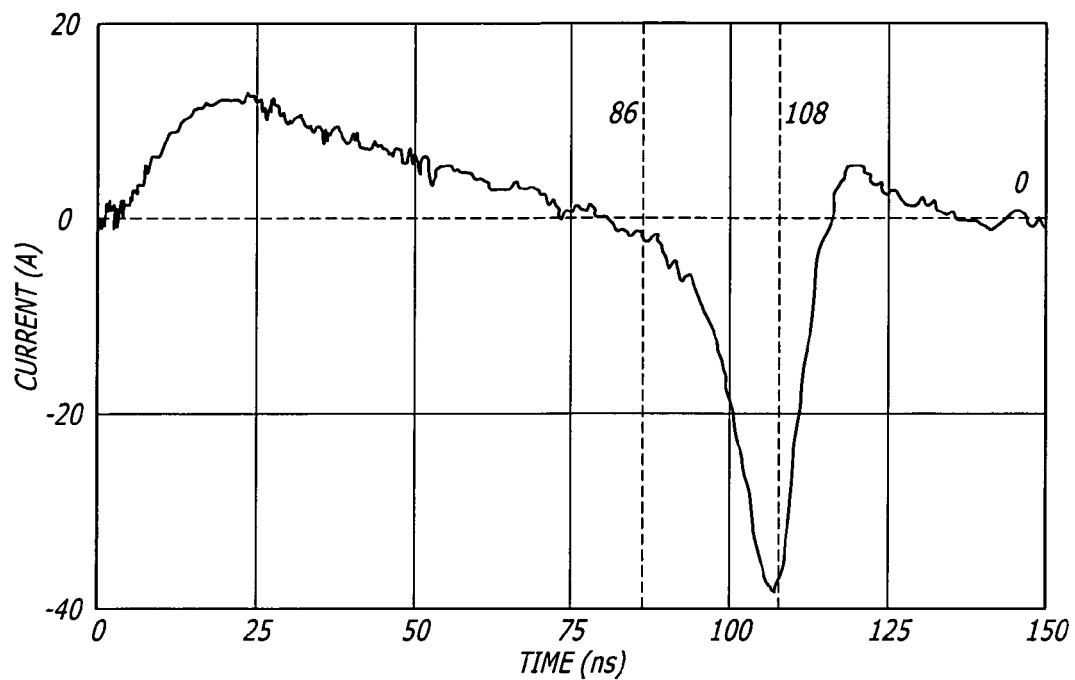
FIG. 36 illustrates current that may flow through the diode array 217 shown in FIG. 35.

FIG. 36 illustrates current that may flow through the diode array 217 shown in FIG. 35. As illustrated in FIG. 36, the diode array 217 may be forward-biased during approximately the first 86 ns. It may then be reverse-biased, following which the charge in its depletion layer may be quickly depleted and the diode switches off. This may open the circuit and commute the current from the diode array 217 to the load.

As can be seen from the values in FIG. 36, the saturated secondary inductance may be less than the designed value, and the peak current may be significantly higher. The higher current may compensate for the nonlinear diode capacitance and the losses of the saturable core. The forward diode pumping current may not be a pure half sine wave, as slow core saturation and resistive losses in the core and the primary MOSFET switch may cause distortion.

The circuits in FIGS. 34 and 35 may generate a unipolar pulse that is applied to a load. That unipolar pulse may instead or in addition first be converted into a bipolar pulse using any known approach.

One approach to convert the unipolar pulse into a bipolar pulse is to differentiate the unipolar pulse with a series capacitance. The resulting width of the pulse, however, may be more than is desired.

Figure 37:
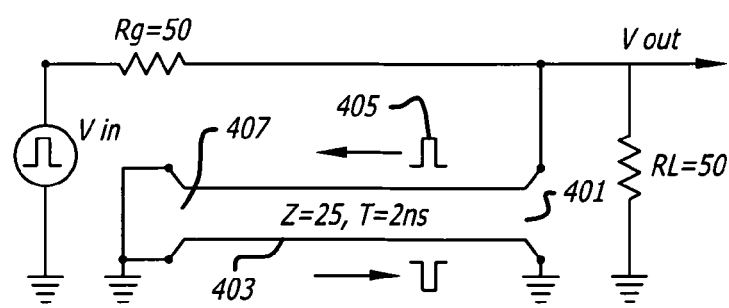
FIG. 37 illustrates a short transmission line used to convert a unipolar pulse to a bipolar pulse.

FIG. 37 illustrates a short transmission line used to convert a unipolar pulse to a bipolar pulse. As shown in FIG. 37, an input 401 to a short transmission line 403 may be connected to the unipolar pulse 405. The unipolar pulse 405 may travel to the end 407 of the transmission line 403 and be reflected back to the beginning 401 of the transmission line 403. The length of the transmission line 403 may be selected so as to cause the reflected pulse to arrive back at the input 401 just when the input pulse 405 falls. This length may be half the unipolar pulse width. The reflected pulse is inverted and is added to the input signal, resulting in a bipolar pulse.

The impedance of the transmission line 403 and the associated circuitry and connections may be selected so as to minimize spurious reflections, all in accordance with well known techniques. For example, the returning pulse may be terminated by the parallel combination of the pulse source and the load impedance. If these are both 50 ohms, the transmission line may be selected to have a 25 ohm impedance to match. Two 50 ohm coaxial cables may be connected in parallel to provide a transmission line with an effective impedance of 25 ohms.

Figure 38:
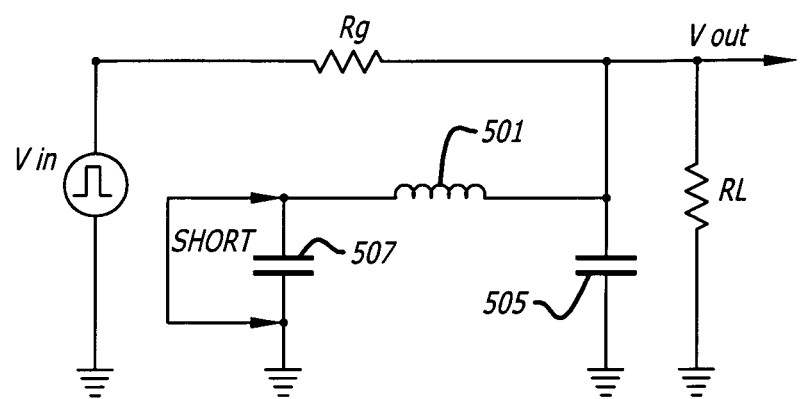
FIG. 38 illustrates a low-pass π network used to convert a unipolar pulse to a bipolar pulse.

FIG. 38 illustrates a low-pass π network used to convert a unipolar pulse to a bipolar pulse. The low-pass π network may be configured to provide electrical characteristics that are equivalent to the transmission line shown in FIG. 37. To a first order, for example, the inductance 501 may equal the delay time of the transmission line 403 multiplied by the impedance of the transmission line 403. Similarly, the total of the capacitances 503 and 505 may be calculated by dividing the delay time of the transmission line 403 in FIG. 37 by its impedance.

Figure 39A:
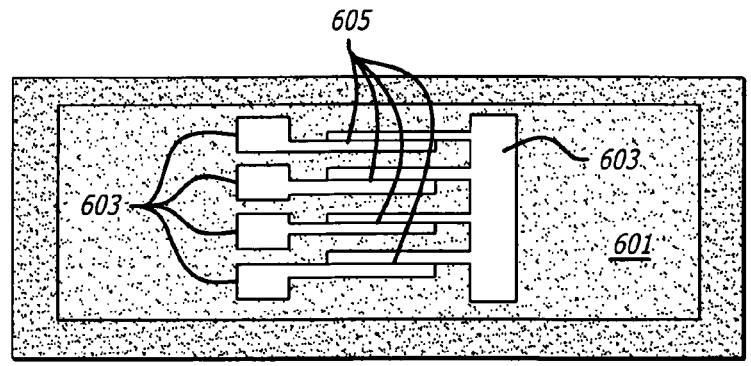
FIG. 39(a) illustrates an instrumented microscopic slide that may serve as a load for pulses generated by circuits, such as those shown in FIG. 34 and/or FIG. 35.

FIG. 39(a) illustrates an instrumented microscopic slide that may serve as a load for pulses generated by circuits, such as those shown in FIG. 34 and/or FIG. 35. As shown in FIG. 39(a), the slide may include a micro slide 601 on which several gold electrodes 603 may be deposited. Other suitable metals may also be used for the electrodes. The electrodes 603 may be positioned so as to form a plurality of channels 605 that may be of any width, such as approximately 100 μm.

Figure 39B:
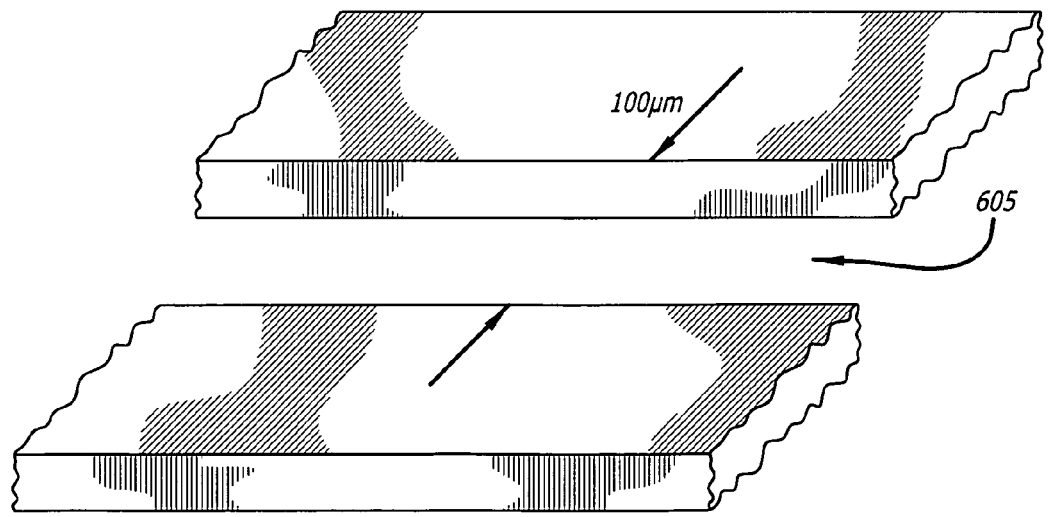
FIG. 39(b) illustrates an enlargement of one of the channels shown in FIG. 39(a).

FIG. 39(b) illustrates an enlargement of one of the channels 605 shown in FIG. 39(a). A solution of cells may be placed within one or more of the channels 605. The micro slide 601 may be covered by another micro slide (not shown) and placed under a microscope (not shown) for study.

Figure 40:
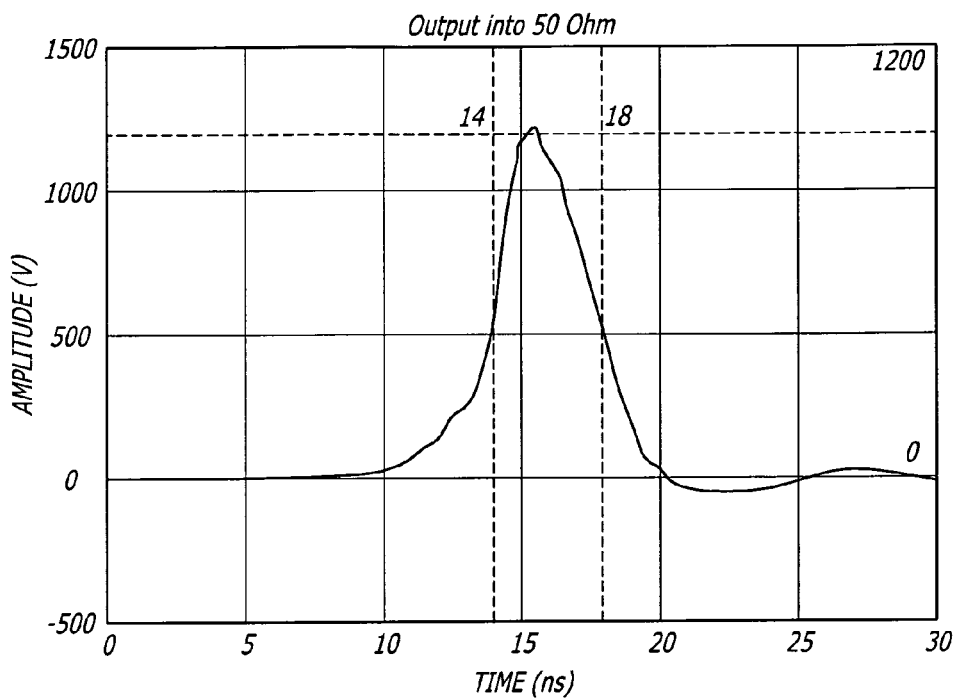
FIG. 40 illustrates a unipolar pulse that may be generated by the circuit shown in FIG. 35 when connected to a 50 ohm load.

FIG. 40 illustrates a unipolar pulse that may be generated by the circuit shown in FIG. 35 when connected to a 50 ohm load.

Figure 41:
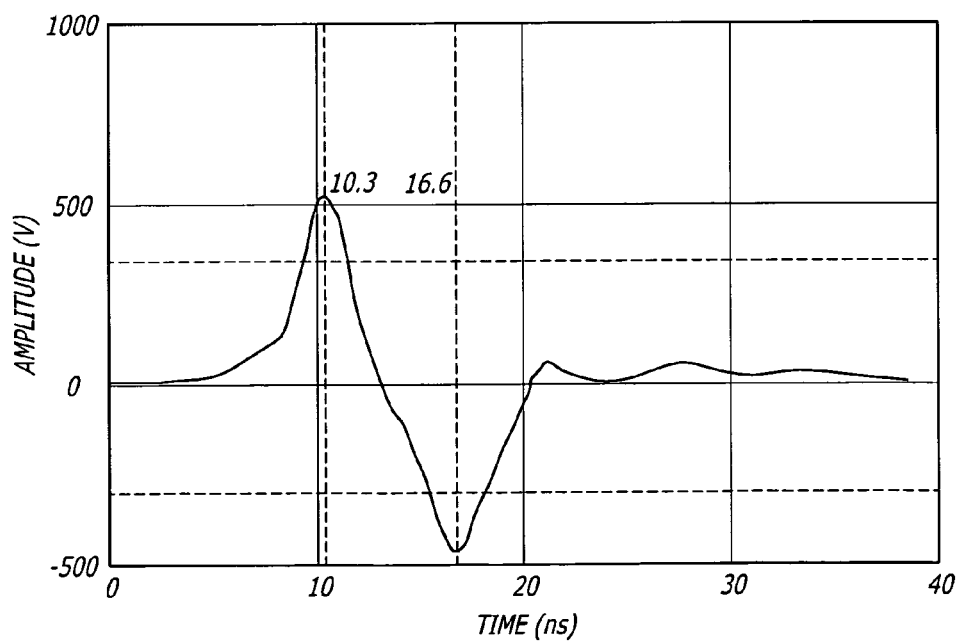
FIG. 41 illustrates a bipolar pulse that may be generated by the circuit shown in FIG. 35 when connected to a 50 ohm load.

FIG. 41 illustrates a bipolar pulse that may be generated by the circuit shown in FIG. 35 when connected to a 50 ohm load.

The components and steps that have been discussed are merely illustrative. Neither of them, nor the discussions relating to them, are intended to limit the scope of protection in any way. Numerous other embodiments are also contemplated, including embodiments that have fewer, additional, and/or different components, steps, features, objects, benefits and advantages. The components and steps may also be arranged and ordered differently.

For example, although capacitances, inductances, resistances and switches have been illustrated in the drawings and/or discussed as single components, they may instead each be made of multiple components, cooperating together to perform the illustrated or recited function.

Minipulser For Cuvettes

In one embodiment of the present invention, a small, compact pulse generator for use with cuvettes was used. A compact pulse generator using a Blumlein, which is a technique for stepping up the voltage for short pulses, was utilized to produce high current and high voltage pulses applied to a standard 1 mm electroporation cuvette. The pulse generator delivered pulses of $V_P=10$ kV peak amplitude and $\tau_P=5$ nanoseconds duration. Bursts of pulses with pulse repetition rate of 10 kHz were achieved, allowing study with various sequences of pulses. The load can be, for example, a standard electroporation cuvette. The electrode area in such cuvettes is typically 1 cm×2.5 cm, and the electrode gap is 1 mm. It is filled with a nutrient solution in which the cells are suspended. The water based solution has a resistivity of $\rho \sim 500$ Ωcm. The dielectric constant of the solution is close to that of water, $\in=81$. This load behaves as a parallel combination of a resistor and a capacitor, with an RC time constant, $\tau_L=\rho \in \in_0$, of approximately 3 nanoseconds. This is comparable to the pulse length. The pulse generator is thus designed to see a load impedance of $ZL \sim 20\Omega$. The known load characteristics and the desirability of lowest possible voltages suggest the Blumlein PFN configuration switched with a pressurized spark gap (FIG. 9). The Blumlein includes two identical series connected transmission lines charged to a common voltage. Each individual line has a characteristic impedance half that of the load.

The electrical length of each transmission line is half the desired output pulse length. The characteristic impedance of the water line is primarily determined by the width of the central strip conductor and the distance to the bottom ground. The interelectrode distance is chosen by the breakdown strength of water and the maximum charge voltage. The chosen width of the center electrode produces the desired $Z=10\Omega$ characteristic impedance. Alternative transmission line configurations can also be used. Two different versions of microstrip lines on high dielectric constant ceramic substrates can be used. In one embodiment of the present invention, these will use ceramic (barium titanate) microstrips that are smaller than the water lines.

In another embodiment of the present invention, a pulse generator (minipulser) that delivered pulses of $VP=10$ kV peak amplitude and $\tau_P=5$ nanoseconds duration with pulse repetition rate of 10 kHz was used.

Cuvette and Cells Electrical Load Characteristics

In one embodiment of the current invention, the load was a standard electroporation cuvette. The electrode area was 1 cm×2.5 cm, and the electrode gap was 1 mm. It was filled with a nutrient solution in which the cells were suspended. The water based solution had a resistivity of $\rho \sim 500$ Ωcm. The relative dielectric constant of the solution is close to that of water, $\in=81$. The load behaves as a parallel combination of a resistor and a capacitor, with an RC time constant, $\tau_L=\rho \in \in_0$, of approximately 3 nanoseconds. This is comparable to the pulse length. The pulse generator was designed to see A load impedance of $ZL \sim 20\Omega$.

Transmission Line Design

Figure 21:
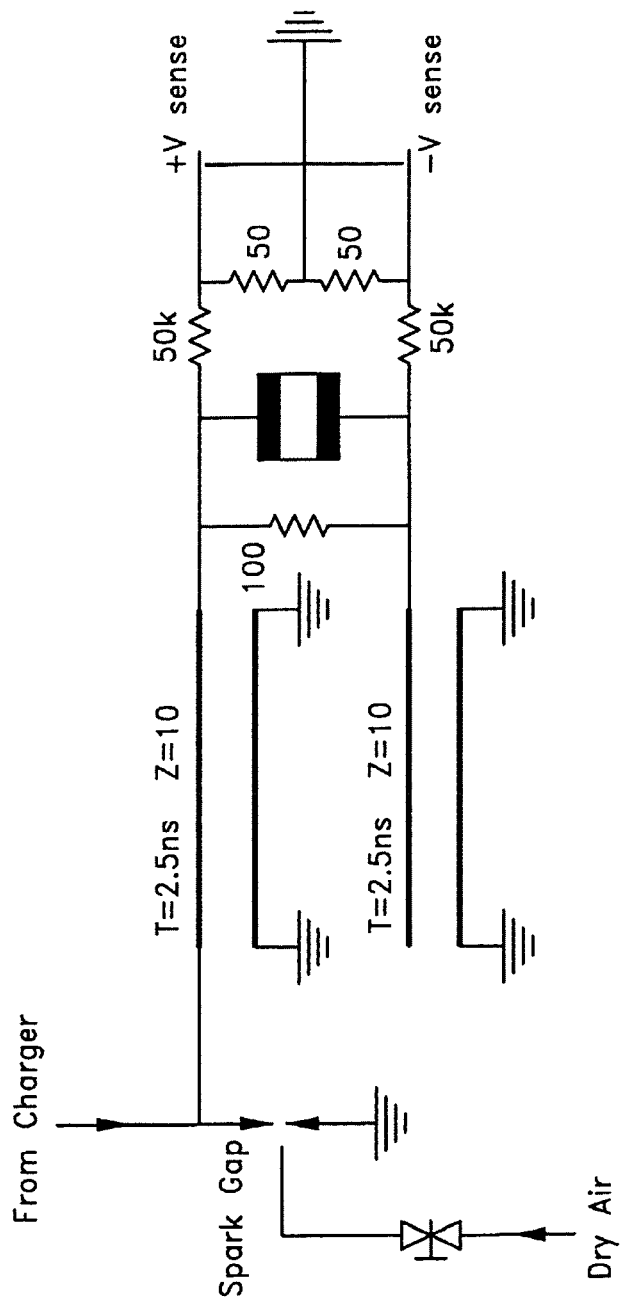
FIG. 21 illustrates the Blumlein PFN configuration.
Figure 23:
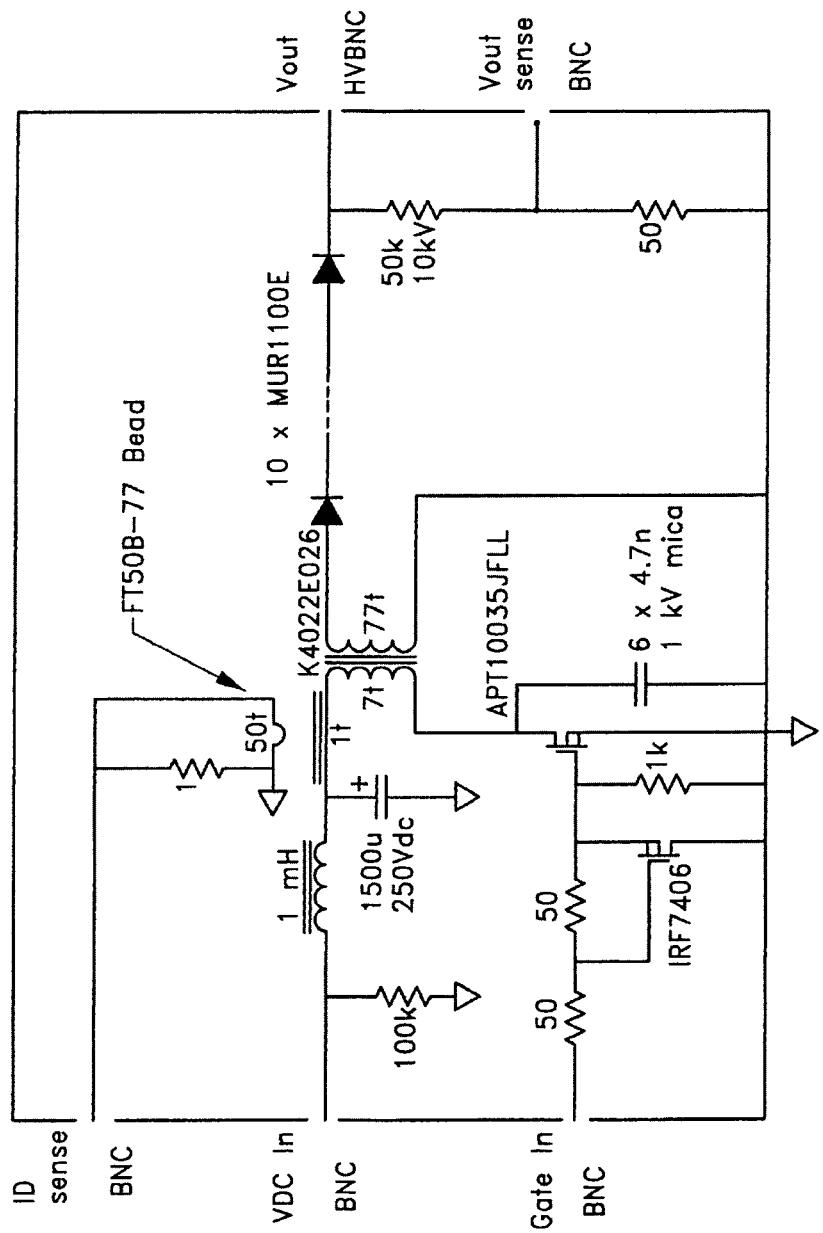
FIG. 23 illustrates a resonant charging circuit.

The known load characteristics and the desirability of lowest possible voltages suggest the Blumlein PFN configuration switched with a pressurized spark gap (FIGS. 21-23). The Blumlein includes two identical series connected transmission lines charged to a common voltage. Each individual line has a characteristic impedance half that of the load.

The electrical length of each transmission line is half the desired output pulse length, $T=\frac{1}{2}\tau_p$. The physical length, LBL, depends on the wave propagation speed in the dielectric medium storing the energy:

$$L_{BL} = \frac{c\tau_P}{2\sqrt{\varepsilon}} \quad (1)$$

Using a distilled water ($\in=81$) and glycol ($\in=37$) mixture as dielectric in an asymmetric stripline configuration, the dielectric constant, and hence the pulse length, was adjusted between $4 < \tau_p < 6$ nanoseconds. The mechanical configuration of the water transmission line is shown in FIG. 22.

The characteristic impedance of the water line was primarily determined by the width of the central strip conductor, w=9.5 mm, and the distance to the bottom ground, d=3.2 mm. The interelectrode distance was chosen by the breakdown strength of water and the maximum charge voltage. The chosen width of the center electrode produced the desired $Z=10\Omega$ characteristic impedance. The choice of water as dielectric led to the use of a relatively fast pulse charging system. The circuit diagram of the charger is shown in FIG. 23.

The circuit was largely immune to transients associated with the discharge of the transmission line. In this mode, the primary switching element of the resonant charger was in the off state when the transmission line is discharged. The circuit charged a 300 pF line to 10 kV in 1.1μ seconds. This charging time was less than the time constant of distilled water. The maximum repetition rate of the charger was f=10 kHz, limited only by the size of the primary DC storage capacitor.

Energy and Power

The energy per pulse, Ep, delivered to the load, RL, can be determined from the pulse length, Ep, and the pulse amplitude, VL:

$$E_P = \frac{V_L^2}{R_L}\tau_p, \quad (2)$$

and the required power, P, is:

$$P = E_p \frac{f}{\eta}. \quad (3)$$

Here, the pulse repetition frequency is f and the efficiency is η. Thus, the charger circuit delivered approximately EP=15 mJ per pulse and provided at least P=300 W of quasi continuous power.

Time Scales

During the charging interval, the water-insulated transmission line can be represented as a capacitor in parallel with a resistor. The capacitance, C, of this combination stored the pulse energy at the peak charging voltage, $$C = \frac{2E_p}{V_L^2}. \quad (4)$$

A properly terminated Blumlein output voltage equals the charging voltage, VL=VCH. The parallel equivalent resistance is calculated from the load capacitance and the time constant of the water dielectric, $\tau_W=\in_r\in_0\rho$, $$R = \frac{\tau_w}{C}. \quad (5)$$

Resistivity of distilled water is $\rho > 1$ MΩ-cm and the relative dielectric constant is $\in=81$, hence, the time constant is about 7 µs. Water eventually acquires an ion concentration that lowers its resistivity and time constant. Keeping the charge time, $\tau_{ch}=1.1$ µs, much less than the initial $\tau_w$, allowed several days of operation between water replacements.

The maximum allowable charge time defines a maximum inductance, LS, in series with the transmission line. The charging waveform is approximately one quarter of the period of the resonant circuit formed by this inductance and the load capacitance. This limits the inductance of the secondary winding of the high-voltage transformer, $$L_S \leq \frac{4\tau_{ch}^2}{\pi^2 C}. \tag{6}$$

Each charging cycle begins with the charging of the primary inductance, LP, to the pulse energy plus losses:

$$L_P = \frac{2E_P}{\eta I_P^2}. \tag{7}$$

The time, tR, it takes to ramp the current to this value, IP, depends on the DC power supply voltage, VDC $$t_R = \frac{L_P I_P}{V_{DC}}. \tag{8}$$

This being the dominant time interval, it sets the absolute maximum repetition rate as well:

$$f \leq \frac{1}{t_R + \tau_{ch} + \tau_P}. \tag{9}$$

Switch and Transformer

The fast turn off requirement led to the use of solid-state devices, such as MOSFETs, for the switching devices. In one embodiment, the selected switch was the APT10035JFLL MOSFET. Its maximum allowable drain voltage is VD=1 kV, and the maximum pulse current is IP=100 A. Typical turn off time is 6 nanoseconds. Fast turn off was achieved in practice by using a fast driving circuit. The circuit in FIG. 2 shows the driving arrangement.

During operation, the switch voltage rises to a maximum, VD, determined by the primary resonant capacitance, CD. The primary voltage was raised to the limit set by the switch rating, with about 10% safety margin, to reduce the turn ratio, $$N = 1.1 \frac{V_L}{V_D}. \tag{10}$$

In this case, the turn ratio is N=11. The primary inductance calculated from Eq. (7) is LP=3.4 µH, the secondary from $L_S=L_P N^2$ is LS=408 µH. The secondary inductance satisfies the inequality in Eq. (6). The primary resonant capacitance, from $C_D=C N^2$, is CD=36 nF. This capacitance needs to be adjusted if the coupling coefficient between the primary and secondary windings of the transformer is different from the optimum value of 64%. The consequences are a small reduction in efficiency, some ringing and modified charge time. In this circuit CD=33 nF, of which about 3 nF is supplied by the drain-source capacitance of the MOSFET. At the end of the current ramp, the energy is stored in the magnetic field of the primary inductance. This field is concentrated in the transformer core. The stored energy divided by the energy density of the magnetic field, BS, in the core indicates the minimum core volume, VC, $$V_C = \frac{2\mu_0 \mu E_P}{B_S^2}. \tag{11}$$

It is advantageous to limit the core volume to a relatively small core permeability, µ. Low permeability also helps to establish the optimum coupling coefficient for efficient resonant energy transfer. Simple separation of the primary and secondary windings, NP and NS turns, on different ends of the bobbin is adequate if µ<100, while external inductance in series with the secondary winding should be used to simulate the leakage inductance if the permeability is high. The minimum core cross section, AC, is given by the flux and the saturation field BS, $$A_C = \frac{L_P I_P}{N_P B_S}. \tag{12}$$

The nickel-iron powder E-core K4022E026 from Magnetics, Inc. has the proper cross section, AC=2.4 cm2, and volume, VC=23 cm3. Initial permeability is µ=26, and the saturation field is BS=0.5 T. A layered winding with monotonically decreasing number of turns on each successive layer results in reduced interlayer and interturn capacitance. The primary winding has NP=7 turns of 18 awg magnet wire placed at one end of the bobbin. The secondary winding is NS=77 turns of 24 awg magnet wire in four layers, separated from the primary winding by 6 mm. The first layer has 40 turns, the second 20 turns, the third 10 turns and the top layer is the remaining 7 turns. The layers are insulated by Teflon tape. The transformer primary inductance swings between 5.1 µH at the beginning of the current ramp to 3.4 µH at the peak of the current. The effective permeability of the core at 100 A peak current is µ=18. Due to this swing in inductance, the ramp time using VDC=48 V power supply is approximately $\tau_R \sim 10$ µs. Estimated temperature rise of the transformer at full power is 32° C. above ambient.

Pseudospark-Based High Voltage System

The pseudospark is a gas phase switch that has some features of thyratrons, but conducts higher current (up to 10's of kA), hold's off higher voltage (typically about 30 kV or more), and switches faster (less than or equal to about 20 nanoseconds). Such a generator will be useful for these applications because of the useful combination of specifications, including variable repetition rate. In one embodiment, the pulse generator delivered pulses of 70 kV peak amplitude and 50 nanoseconds duration. Bursts of 100 pulses with pulse repetition rate of 1 to about 100 Hz were provided within the first phase of the research. The final pulse amplitude was achieved by using a pulse transformer.

Micropulser

The responses of cell populations (1×106 cells in an electroporation cuvette) and of single cells (in groups of 10 or 20) in nanoliter-sized microchambers are used to determine the heterogeneity of the responses of members of a cell population to pulsed electric fields.

Figure 15:
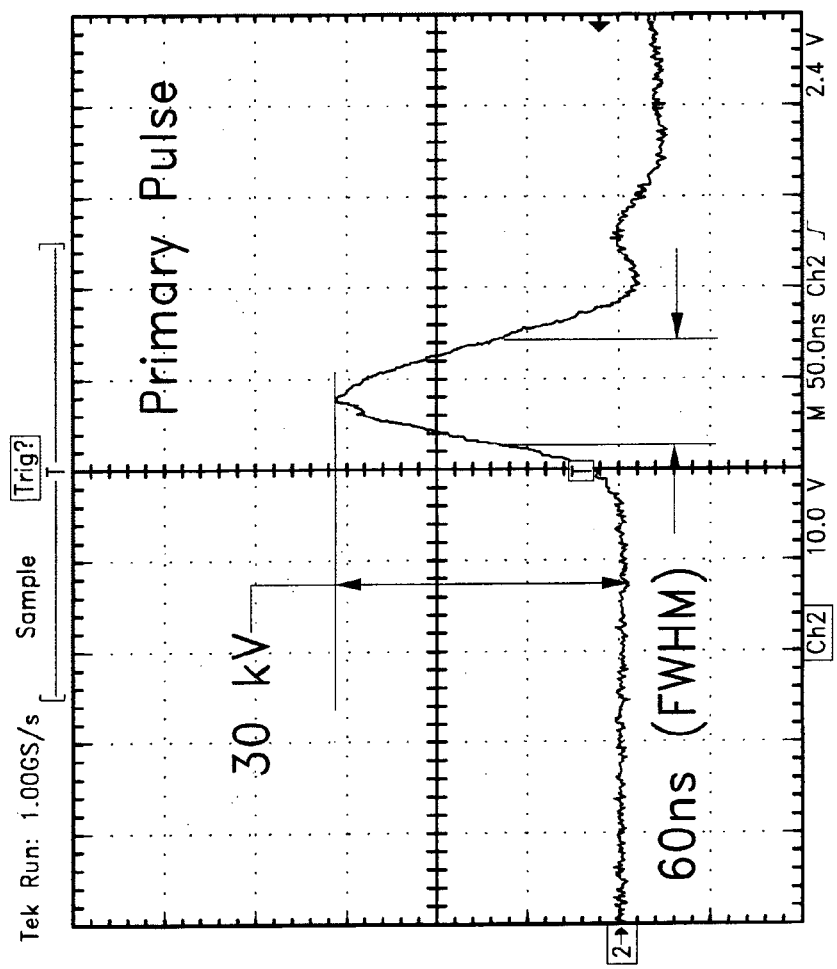
FIG. 15 shows the output of a pseudospark-based pulse generator. This pulse generator is designed for higher voltage needs, and is used along with other pulse generators, to provide a range of options.

Optics and biophotonic methods are used (FIG. 15). To support the pulsed power, microscope-slide-size cuvettes are fabricated with electrode structures, and fields are introduced using "micropulser" technology. These microscope-slide-based structures, fabricated with microelectromechanical systems (MEMS) technology, permit direct optical observation of individual cells during and after pulse delivery, in relatively real time (nanosecond time resolution).

Figure 16:
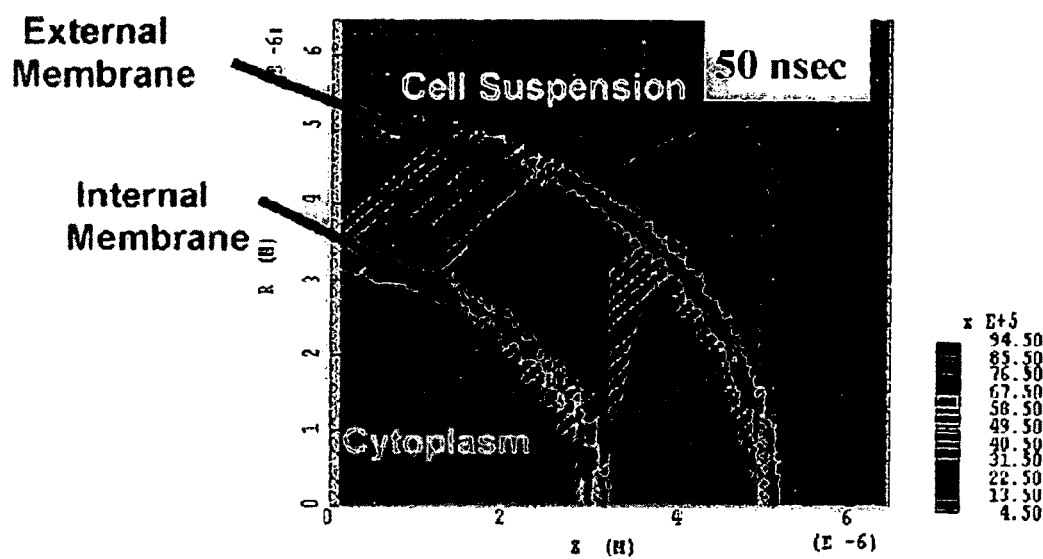
FIG. 16 shows a field across an internal nuclear or mitochondrial membrane, 10's of nanoseconds after pulse application.

A miniature solid state pulse generator (about 400 V) designed for the electroperturbation of biological cells in solution is used (FIG. 16). Typically, cell electroperturbation with nanosecond pulses is performed on a batch of cells in a cuvette with a volume of less than 1 mL. A "micropulser" designed to produce pulses with several hundred volts to a narrow channel of cells on a microscope slide is based on one or more fast power MOSFETs and form relatively square pulses of variable width. The pulse generator unit and slide holder are compact and designed for optical access and monitoring.

Figure 24:
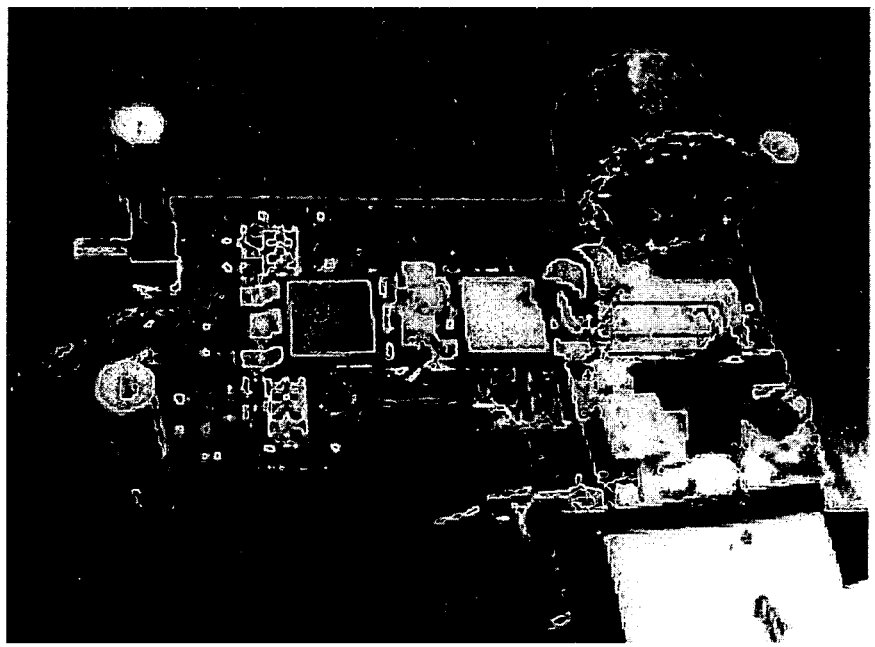
FIG. 24 is a photograph of a micropulse prototype circuit layout.

A micropulser (FIG. 24) designed to produce relatively intense pulsed electric fields on a microscope slide for cell electroperturbation is described herein. Pulse parameters for electroperturbation include fast rise time, amplitude, and width. The micropulser is designed to provide flexibility in these parameters along with maximum 25 MHz repetition rate. The micropulser provides both miniaturization and flexibility for any pulse width as a single-MOSFET output stage pulse generator.

Biological Load

The load for the micropulser is a glass slide having deposited platinum electrodes that form channels 25 μm wide, 25 μm deep, and 20 mm in length. Cells suspended in liquid growth medium are pipetted into the channels. The growth medium within one such channel presents an electrical load of 37 ohms in parallel with 14 pF. The microscope slide in process of fabrication has two channels 25 μm wide and two channels 50 μm, giving a total parallel load of 12 ohms in parallel with 42 pF.

Physical Requirements

In one embodiment, the microscope slide and micropulser unit fit on the stage of an optical microscope. Having the objective lenses beneath the stage allow for a more spacious working area. In one embodiment, the pulse generator has all RF power devices on stage, leaving the DC power source and trigger signal source as external equipment. Additionally, the fast rise time requirements lead to short current paths for low inductance. In one embodiment, components are surface mounted and coplanar over the ground plane. A MOSFET switched capacitor is well matched to the physical dimensions of the working environment.

Electrical Requirements

In one embodiment, the MOSFET used with the micropulser is the DEI275-501N16A, chosen for its fast 2 nanoseconds rise time and power handling capabilities appropriate for the intended biological load. Derating to 80% provides a maximum voltage of 400 V into 10 ohm load with 40 A current. Its pulsed current rating is 100 A. In one embodiment, only one MOSFET is used to drive the load directly. Integrity of the sharp pulse edge is maintained by mounting the slide coplanar and adjacent to the MOSFET and energy storage capacitor. Conduction paths are copper strips over an insulated ground plane. In one embodiment, the EVIC420 evaluation board serves as the base for the micropulser system.

In one embodiment, the gate driver is the matching DEIC420 chip incorporating the same low inductance design as the MOSFET. The fast switching speed of the MOSFET gate causes large oscillations in the drive circuit. Switching noise is sufficiently large to cause false triggering of the MOSFET after short pulses<60 nanoseconds. The gate pin noise with no filtering is 18.6 Vpeak having an oscillation frequency of 36 MHz. The gate drive IC propagates the noise through even to its logic level input pin. The DEIC420 driver VCC power pin is 15 V and shows 500 mV peak noise spike with or without gate filtering. Thus, power supply noise is not responsible for the large swings on the gate drive signal. The gate noise is also independent of MOSFET load and drain voltage.

Figure 10:
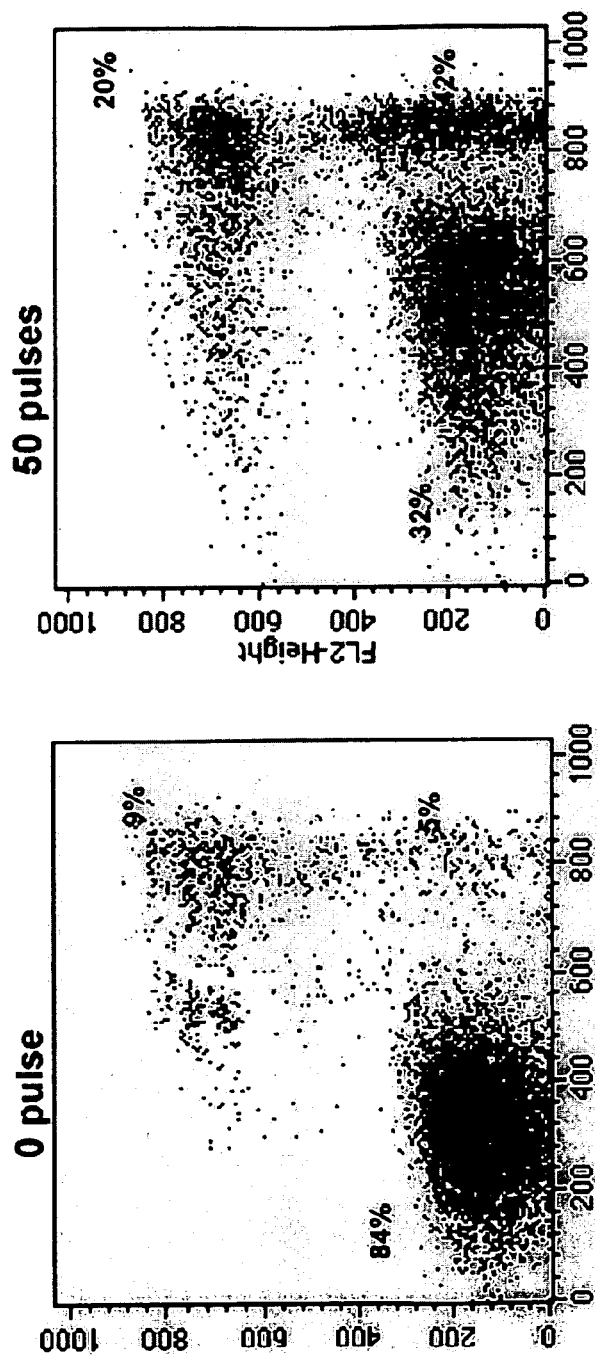
FIG. 10 shows the induction of apoptosis by 50 repetitive 20 nanosecond, 40 kV/cm pulsed electrical shock as measured by Annexin V-FITC and propidium iodide (PI staining of the shocked (50 pulses) and unshocked (0 pulse) cells at 8 hours after the shock treatment. The percentage of cells in the nonapoptotic (lower left), early apoptotic (lower right), and late apoptotic (upper right) quadrants is indicated. At right is depolarization of membrane as a function of the number of pulses.
Figure 11:
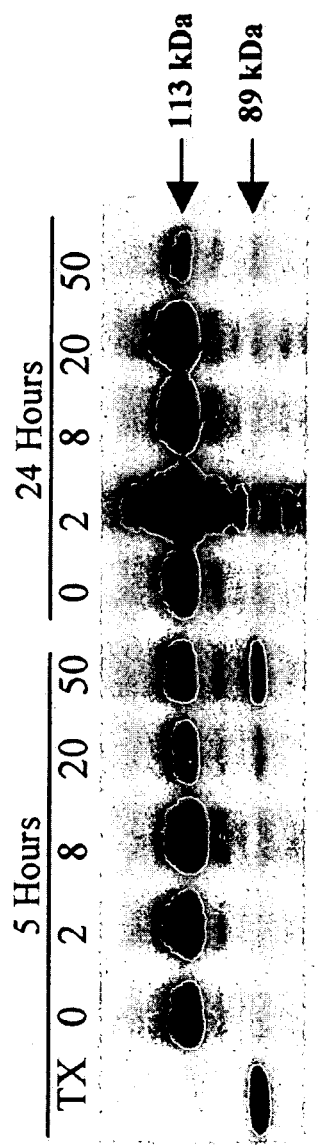
FIG. 11 is an immunoblot SDS-PAGE blot analysis of PARP cleavage in response to electric shock and triton X-100 (TX) treatments. The decrease in the quantity of native form of PARP (113 kD) and the increase in its proteolytic cleavage products (89 kDa) are characteristic of apoptosis.
Figure 12:
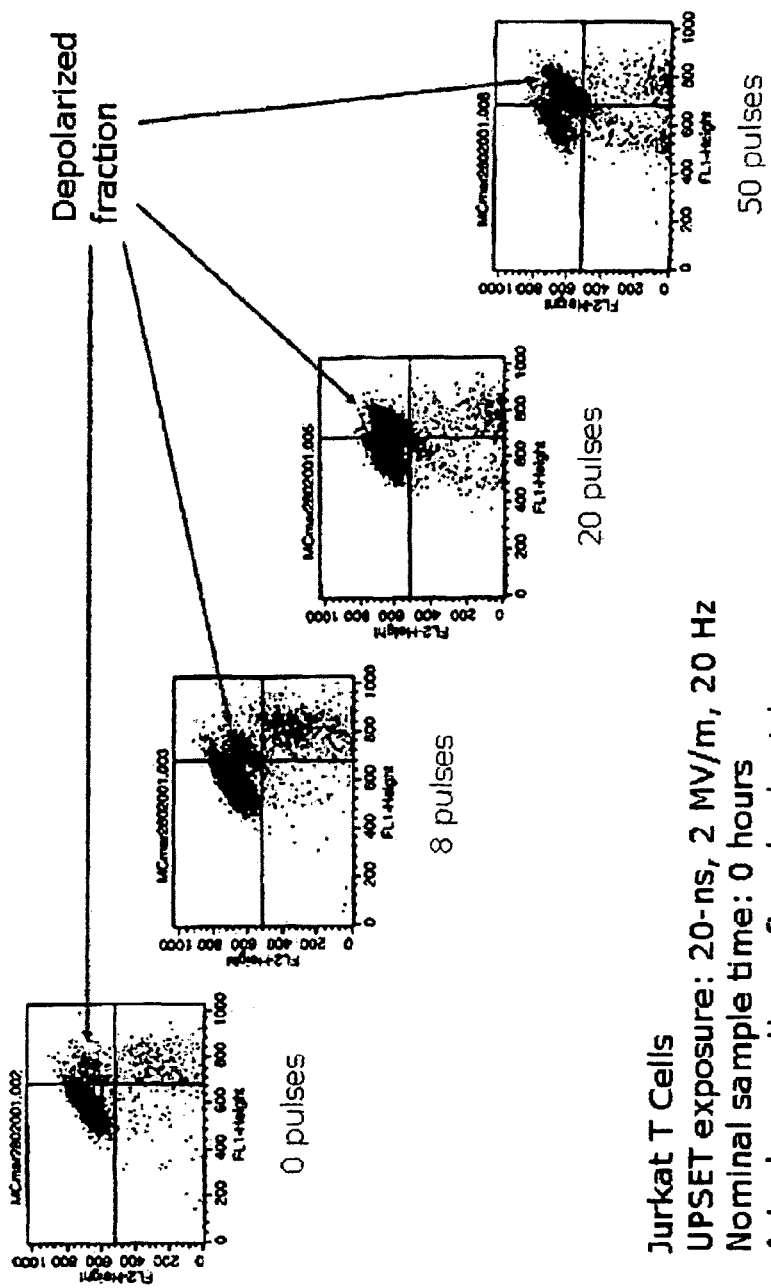
FIG. 12 is a flow cytometry analysis (JC-1 staining) showing increased mitochondrial membrane depolarization as function of pulses.
Figure 13:
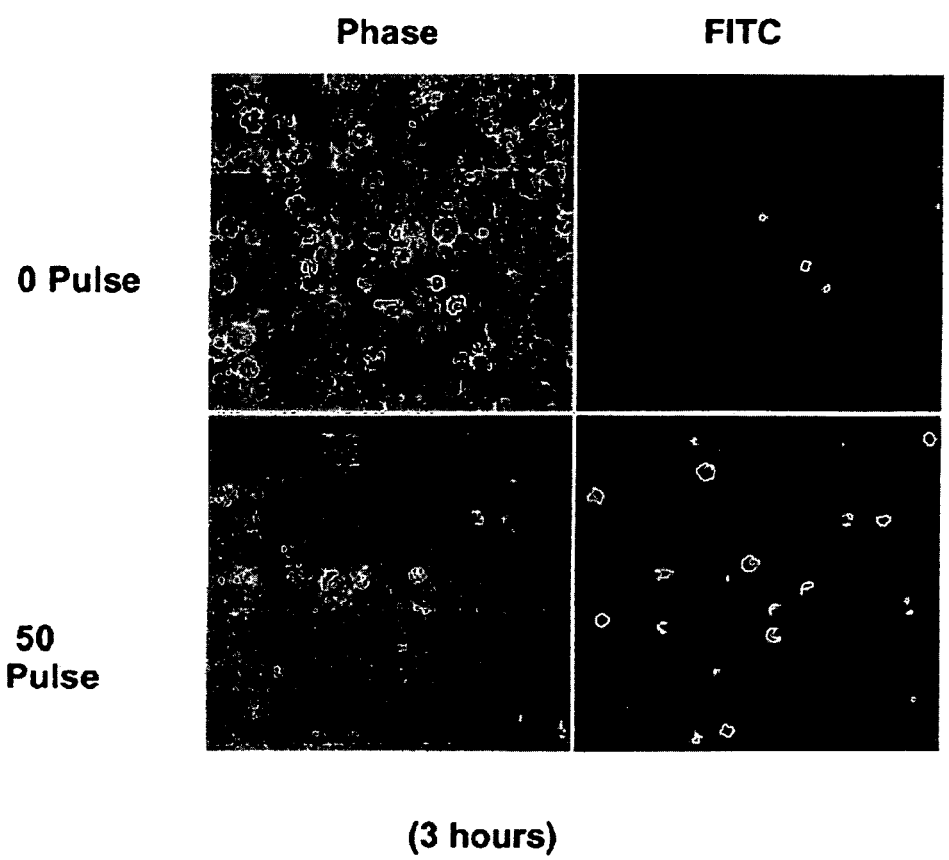
FIG. 13 shows capsase activation imaged with FITC-VAD-FMK.

Saturable reactor filtering is placed in series with the gate driver and gate to reduce switching spikes at the gate. Drain fall time is slowed from 3.1 nanoseconds to 3.8 nanoseconds by the addition of gate filtering for 16.2 Vpeak noise and partial false triggering of the MOSFET after turn-off from a 20 nanoseconds pulse. Sufficient inductance reducing the drain fall time to 4.2 nanoseconds results in 13.2 V peak noise on the gate and no false triggering of the MOSFET. The chosen filter inductor includes a copper wire and two saturable reactors in parallel. Both of the saturable reactors are Toshiba Spike Killer SA7×6×4.5 magnetic cores with one turn each. FIG. 10 shows the cost in drain fall time to achieve noise suppression using varying combinations of paralleled conductors and saturable reactors. At 13.2 V and below, the MOSFET experiences no false triggering after a 20 nanosecond pulse.

From the oscillation observed on the MOSFET gate pin, the equivalent series resistance and inductance of the gate driver and filter is calculated. The MOSFET has a known gate capacitance of 1.8 nF. The oscillation frequency gives the inductance from Eq. (13) and the known gate capacitance.

$$L=1/(4\pi 2F2C) \qquad (13)$$

Series resistance was determined from the decay constant of the oscillation according to Eq. (14).

$$V1=V0\exp(-2tL/R) \qquad (14)$$

Figure 25:
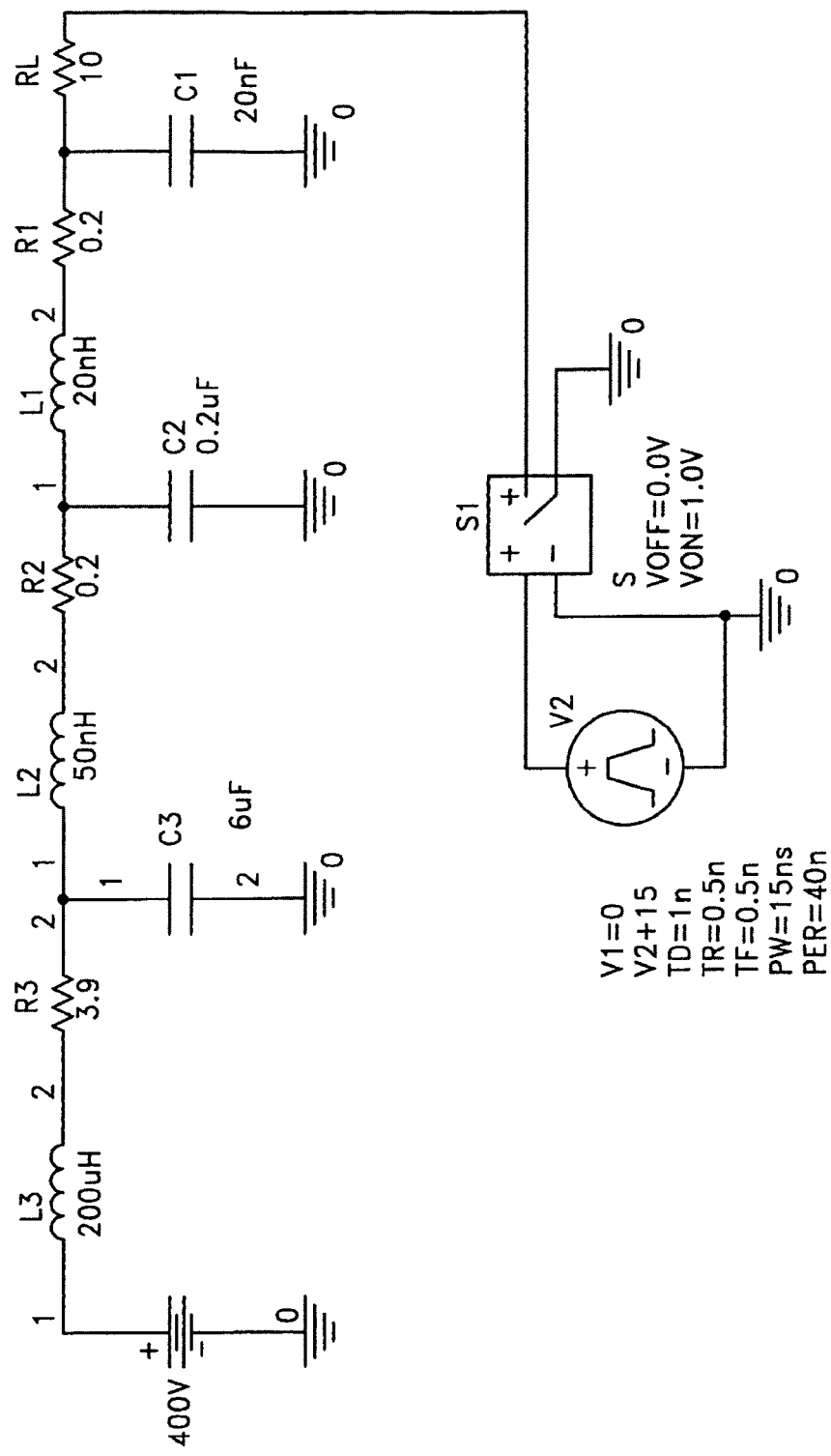
FIG. 25 illustrates a charging circuit design for a micropulser.
Figure 26:
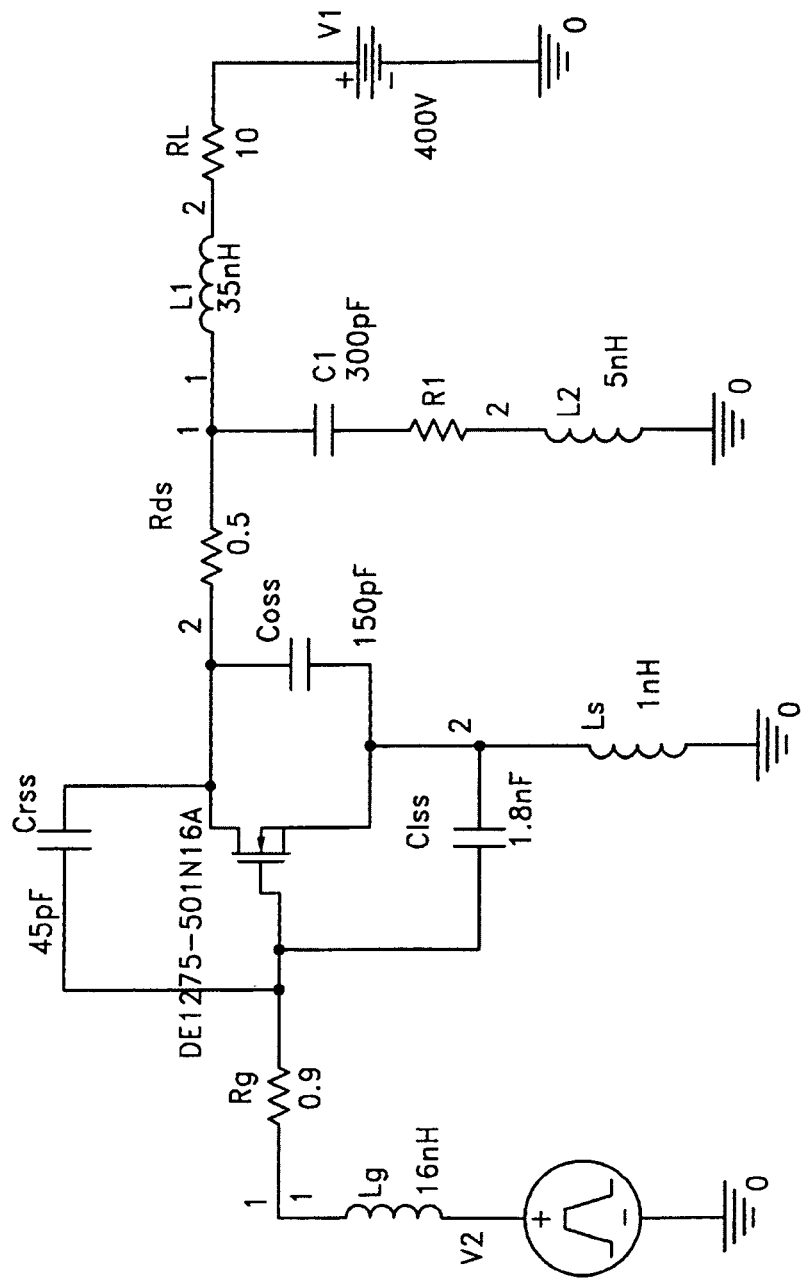
FIG. 26 is a micropulser RF circuit schematic.

The circuit characteristics are determined for each filter configuration that produced measurable gate oscillation. Specifications for the MOSFET give a gate resistance of 0.3 Ohms, leaving 0.28 ohms for the gate driver IC. To achieve 25 MHz pulse repetition rates, a charging network is used to maintain the charge on the primary energy storage capacitor. The duration of 25 MHz burst is limited by tertiary energy storage capacitor C3 in FIG. 25. The RF circuit is shown in FIG. 26.

In one embodiment, the charging network is designed to maintain the primary energy storage capacitor at >95% of full charge using a 400 W power source. Capacitor C1 is chosen at 20 nF for its appropriate physical size. The maximum allowable burst length dictates the minimum value of C3. For a 15 nanosecond wide pulse used during 25 MHz operation, the energy per pulse is 0.24 mJ given by Eq. (15).

$$E=tV2/R \qquad (15)$$

The value of C2 is as large as possible while minimizing low stray series inductance to the primary capacitor C1. Additionally, C2 maintains a charge of 380 V. Inductors L1 and L2 represent the equivalent series inductance of the capacitors and conduction paths. Energy efficiency is 96%.

Catheter-Based Micropulser

In several embodiments of the current invention, micropulsers can be designed for incorporation into handheld catheters. This includes, but is not limited to, both small cabled systems with a catheter head and systems with the pulse generation in the catheter, fed by a small pulse charging system. Pulse transmission preserving field is used in these systems for fast rising pulses. Such a system, i.e. a pulse generator for high field, fast pulses that can provide 10 to 100 kV/cm fields at the tissue in times of the order nanoseconds, can provide the desired parameters.

A typical catheter available from commercial sources is representative of an impedance-matched device. In one embodiment, the catheter is coupled to a cable matched to the pulse generator, in a manner very similar to UHF (Ultrahigh Frequency) coupled cable used for microwave measurements.

D. Sub-Cellular Responses to Ultrashort Electric Fields

Real-Time Optical Imaging of Sub-Cellular Responses to Ultrashort Electric Fields The in-situ the behavior of the cell over time and capturing events on the order of sub-seconds range are monitored to determine the mechanisms and processes that underlie the therapeutic effects of ultrashort electric fields. Non-invasive, real-time investigations of sub-cellular events resulting from the application of ultrashort electric fields using optical spectroscopy/imaging techniques are performed. These techniques include wide-field, confocal, multiphoton, and lifetime imaging microscopy. Taking advantage of both autofluorescence from native fluorophores in cells and the availability of sensitive and selective fluorescent/molecular probes for living cells, these approaches allow direct investigations of sub-cellular events at cell membranes, organelles and DNA levels. Using these techniques, the electrical response of cells (normal vs. tumorgenic, or terminally differentiated vs. rapidly dividing) to distinct regimes of pulsed electric fields, and the intra-cellular mechanism triggered by these fields, which may lead to apoptosis, are observed in real time.

An optical spectroscopy/imaging microscopy instrumental apparatus is used for repetitive 3-D functional and structural imaging of live cells treated with ultrashort electric fields. Methodologies for real-time imaging of cellular and sub-cellular events upon exposure to UPSET are used to observe, inter alia: (a) membrane dynamics (cytoplasmic and mitochondrial membranes) exposed to various pulsed field regimes (pulse width, intensity, frequency), (b) morphological and functional changes in cells and cell membranes induced at the ultrastructure level (at the cell surface, within the cell, at the organelles levels), (c) changes in intracellular ions homeostasis and Ca2+ channels, and (d) changes of NADH fluorescence emission.

Instrumental Apparatus Design

A microscopy system that would allow, not only for the functional/structural imaging of living cells, but also for direct shocking and incubation of cells (or cell cultures) on the stage of microscope, and temporal monitoring of sub-cellular changes, was used. In one embodiment, this system was achieved by integrating a microscopy system with a micropulser/microchannel system.

This microscopy system extends on current fluorescence microscopy and time-resolved fluorescence spectroscopy systems, including: (i) a motorized fluorescence inverted microscope (Carl Zeiss: Axiovert 200, Nomarski DIC, AxioCam digital camera, 5 photo-ports with confocal/multi-photon accessibility, AxioVision software control, imaging functions including time-lapse, multichannel, Z-stack, mark and find, distance measurements, angle calculations, statistics); (ii) an ultra-high repetition rate gated intensified CCD camera system (LaVision: PicoStar HR-12, gate widths down to 80 picoseconds); (iii) imaging spectrograph (Acton: Spectra Pro 308, dual output; triple-turret 2 gratings one mirror), various detectors (fast photomultipliers tubes, photodiodes), and supporting electronics (fast digitizers, gate delay generators, preamplifiers). Several laser sources (YAG-pumped OPO-doubler pulsed tunable 200 nm-2 micrometers; Argon; He—Ne) can also be used in accordance with several embodiments of the current invention.

Whole-Field Fluorescence Lifetime Imaging Microscopy (FLIM) with Optical Sectioning In one embodiment, a motorized Axiovert 200 upright microscope, the ultrafast gated ICCD camera system (Image Intensifier, CCD camera, advanced picosecond delay unit, software package including control, image acquisition, processing and analysis), a Ti-Sapphire laser and the supporting opto-electronic components are used in accordance with several embodiments of the current invention. A detailed description of an FLIM system with optical sectioning and its performance has been reported in the imaging art (S. E. D. Webb, et al.; A wide-field time-domain fluorescence lifetime imaging microscope with optical sectioning; Review of Scientific Instruments; Volume 73, Number 4; April 2002; M. J. Cole, et al.; Time-domain whole-field fluorescence lifetime imaging with optical sectioning; Journal of Microscopy, Vol. 203, Pt. 3, September 2001, pp. 246-257, all herein incorporated by reference. Due to photobleaching or dynamic changes in the fluorescence probes, the use of whole-fields approach based on structural illumination is used to acquire 3-D fluorescence information with a minimum excitation intensity and in minimum time. Using a multispectral imager, this technique also provides multiple spectrally resolved images (on a single detector) of a single spatial region. This approach is advantageous for monitoring fast sub-cellular events occurring at short time periods after cells exposure to electric field. The sensitivity of lifetime (time-resolved fluorescence measurements) is exploited for i) monitoring changes in the chemical environment of the fluorophores (ion concentration and binding, Ca, K); ii) monitoring the redox state of pyridine nucleotides NADH and NADPH; iii) contrasting the emission of specific fluorophores against the autofluorescence background arising from the same detected microscopic volume element; and iv) discriminating (in multi-labeling experiments) of molecules with overlapping fluorescence emission bands (different fluorescence decays). (R. Cubeddu, et al.; Time-resolved fluorescence imaging in biology and medicine; Topical Review; Institute of Physics Publishing, J. Phys. D; Appl. Phys, 35 (2002) R61-R76); M. Wakita, et al.; Some Characteristics of the Fluorescence Lifetime of Reduced Pyridine Nucleotides in Isolated Mitochondria, Isolated Hepatocytes, and Perfused Rat Liver In Situ; J. Biochem. 118, 1151-1160 (1995); B. W. Pogue, et al.; In vivo NADH Fluorescence Monitoring as an Assay for Cellular Damage in Photodynamic Therapy; Photochemistry and Photobiology, 2001, 74(6); 817-824, all herein incorporated by reference). One skilled in the art will understand that FLIM can also be used as a technique for DNA chip reading, thus providing direct evaluation of gene expression.

Confocal and Multiphoton Scanning Microscopy

The microscopic system described above can be customized for laser scanning microscopy measurements by adding a scanning module and the corresponding electronics and software control modules. Confocal and multiphoton imaging microscopy provide protocols for imaging sub-cellular structure and dynamic processes with high spatial resolution, both in vitro and in vivo. Applications include, but are not limited to, subcellular imaging of NADH autofluorescence, monitoring of cell division, protein localization and gene expression, Ca2+ uncaging and dynamics, and cell developing neuritic outgrowths. Moreover, these techniques provide for imaging thick biological specimens, thus allowing imaging of UPSET effects on cell culture or 3-D geometry.

Fluorescence Spectroscopy

Although 2- or 3-dimensional display of data provided by fluorescence imaging is useful whenever the localization of any marker is desired, point spectroscopy is particularly advantageous in providing a detailed knowledge of the parameters that characterize the fluorescence emission, such as spectral features, decay time and polarization. These parameters provide a relatively accurate and quantitative interpretation of fluorescence information. These features are provided by integrating a motorized Axiovert 200 upright microscope with an imaging spectrograph (Spectra Pro 308) and a photomultiplier (gated microchannel plate). The dual output of the imaging spectrograph system allows imaging and spectroscopy within the same system. This system facilitates the study of the membrane dynamics and provided quantitative membrane potential data.

NADH Autofluorescence

When excited with wavelengths at about a 350-360 nm range, NADH in cells exhibits strong fluorescence with peak emission at about 450-460 nm. Both steady-state and time-resolved (lifetime) fluorescence spectroscopy/imaging methods are used to study fluorescence in living cells. The changes in the cellular NADH fluorescence emission upon UPSET exposure are monitored. Autofluorescence imaging of mitochondrial and nuclear NADH complement the real-time tracking of the mitochondrial membrane potential, providing an additional, time-resolved indicator of the metabolic status of pulsed cells, and revealing information about the role of early PARP activation in stress-induced apoptosis.

Real-Time Life-Cell Imaging of Sub-Cellular Events

In one embodiment of the present invention, subcellular transformations resulting from UPSET exposure are provided in several cell lines, including Jurkat T lymphoblasts, WERI-Rb-1, C6/LacZ7, and DI TNC1. One skilled in the art will understand that other cell types can also be used in accordance with several embodiments of the current invention. In one embodiment, a plurality of cells are shocked using a micropulser/microchamber, as described above. A perfusion microchamber with controlled temperature and atmosphere and with UPSET electrodes for long-term, continuous, microscopic observation of individual cells after pulsed field exposure are used. Data is acquired in real-time for a single cell or a few cells (up to about 10) and cell culture. Wide-field fluorescence microscopy systems are used for imaging.

Membrane Dynamics (Cytoplasmic and Mitochondrial Membranes)

The dynamic process occurring at the cell membrane level exposed to various pulsed field regimes, such as pulse width, intensity, frequency, are studied. The fluorescence emission of fast-response voltage-sensitive membrane potential fluorescent probes is measured. Typically, the fluorescence intensity for these dyes changed linearly with the membrane potential. Examples include: (1) RH dyes (e.g. RH 421, RH 414) which show (fast decrease of fluorescence upon membrane depolarization. For instance RH 421 has exhibited >20% change in fluorescence per 100 mV applied to neuroblastoma cells; (2) Charge-shift styryl dye di-4-ANEPPS or di-8-ANEPPS, which are sensitive probes for detection of sub-millisecond membrane changes. Di-8-ANEPPS has a fairly uniform 10% per 100 mV changes in fluorescence intensity in a variety of tissue, cell and model membrane systems, for example. These two dyes have been successfully used to investigate the membrane potentials in cell neurobiology studies (mapping of membrane potential along neurons and muscle fibers, imaging of membrane potentials evoked by visual and olfactory stimuli, detection of synaptic and ion channel activity, Ca2+ measurements) as well as to study the membrane potential induced by external electric fields during classic electroporation (square-wave electric pulses); (3) JC-1, fluorescence ratio detection, which allow comparative measurements of membrane potential and the determination of the percentage of mitochondria within a population that respond to an electric stimulus, so that subtle heterogeneity in cellular responses are discerned.

Membrane dynamics studies provide valuable information regarding: (i) membrane potential changes under variations in electric field conditions (intensity, duration, number and frequency) and under different environmental conditions (pH, and ionic strength); (ii) time constants for processes ongoing at the membrane; (iii) pore formation kinetics and resealing, (iv) dielectric membrane breakdown, (v) correlations of experimental observations with analytical models; and (iv) differences in membrane dynamics between normal and tumor cells.

Morphological and Physiological Transformations

The morphological and physiological changes in cells and cell membranes induced at the ultrastructure level, such as at the cell surface, within the cell, and at the organelles, by different regimes of electric fields are monitored in real time. Dynamic sub-cellular changes that take place during shocking, at short time intervals (minutes) and within several hours, are observed. Organelle-specific, DNA-specific and apoptosis-specific fluorescent probes are used, including JC-1, annexin V-FITC, propidium, FITC-VAD-FMK. One skilled in the art will appreciate that other similar probes can also be used in accordance with several embodiments of the current invention.

In several embodiments of the present invention, Green Fluorescence Protein (GFP) and Hoechst 33342 are used as fluorescent probes. GFP is a useful tool for monitoring complex phenomena such as gene expression, protein localization, and organelle structure in prokaryotic, eukaryotic and mammalian living cells. GFP permits direct and indirect biomolecular analysis at the genomic, proteomics or signal transduction level (Zhu, X., Craft C. M., 2000. The carboxyl terminal domain of phosducin functions as a transcriptional activator. Biochemical and Biophysical Res. Comm. 270: 504-509; Zhu, X., Ma, B., Babu, S., Murage, J., Knox, B. E., Craft, C. M., 2002. Mouse cone arrestin gene characterization: promoter targets expression to cone photoreceptors. FEBS Letts 524 (1-3):116-122, all herein incorporated by reference). By co-transfecting GFP mutants, the nucleus and mitochondria are visualized simultaneously in living cell, thus allowing direct study of protein redistribution and protein-protein interaction. By fusing GFP to specific proteins (eg., vesicle docking and fusion, receptors or channels), GFP provides a tool for in vivo monitoring of the sorting and intracellular fate of these proteins. Hoechst 33342, a DNA stain with blue fluorescence upon binding to DNA, is largely used in many cellular applications, including cell-cycle and apoptosis studies. Rapid, real-time visualization of changes in cell and organelle shape, size, and function (with phase contrast or with appropriate fluorescent-tagged reporters) can reveal field-induced rearrangement or disruption of vacuoles and intracellular compartments, the time course of membrane phospholipid translocation, and alterations in cytoskeletal integrity and organization.

Intracellular Ca2+ and Ca2+ Channels

In several embodiments, ion-sensitive fluorescent probes are used. These probes include, but are not limited to, Fura, Indo, Calcium-Green, Calcium-Crimson; voltage-gated calcium channel blocker Verapamil and stretch-activated calcium channel blockers gadolinium chloride and cobalt chloride. Using well-established protocols, localized or cell-wide changes in intracellular Ca2+ concentration following pulse exposure are identified (Fluorescence and luminescent probes for biological activity. A practical guide to technology for quantitative real-time analysis. Biological techniques series, WT Mason Ed., Academic Press, 1999, herein incorporated by reference). Not wishing to be bound by the following theory, it is believed that electric field-induced apoptosis is caused by the perturbation of normal interactions between calcium compartments in the endoplasmic reticulum and the Ca2+-sensitive mitochondria.

D. Computational Science and Simulations

Computational Modeling

Computational modeling has been developed for solving a variety of electromagnetic problems. The primary tools for this type of work are particle-in-cell codes (PIC) that solve self-consistently Maxwell's equations for electromagnetic fields and the motion of particles in those fields (R. G. Hemker, F. S. Tsung, V. K. Decyk, W. B. Mori, S. Lee, and T. Katsouleas, "Development of a parallel code for modeling plasma based accelerators," IEEE Particle Accelerator Conference 5, 3672-3674 (1999), herein incorporated by reference). These codes solve for electric and magnetic fields by solving finite difference equations in the time domain. Typically, these codes use the Finite Difference Time Domain ("FDTD") method to solve wave equations in a medium. The electro-manipulation and diagnosis of cells performed in accordance with several embodiments of the present invention were complemented with a computational modeling program that provided electromagnetic simulation for the study of the electrical response of living cells to tailored electrical pulses.

Figure 17:
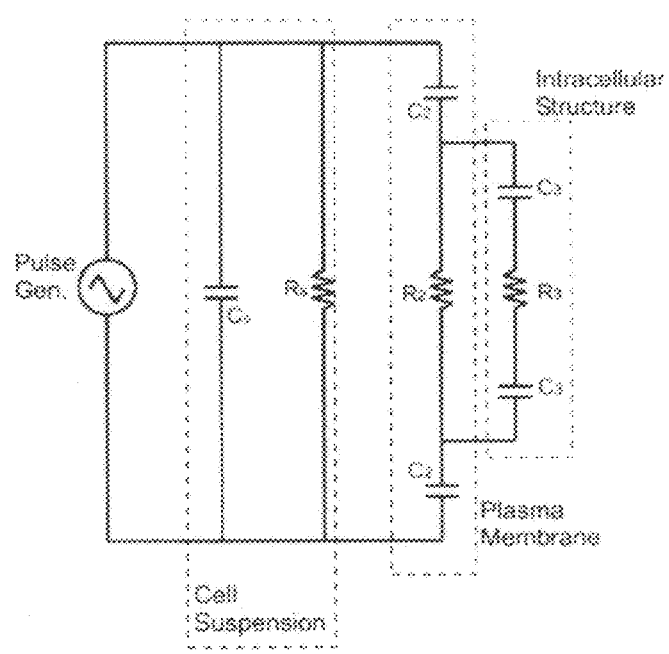
FIG. 17 illustrates simple lumped circuit elements.
Figure 18:
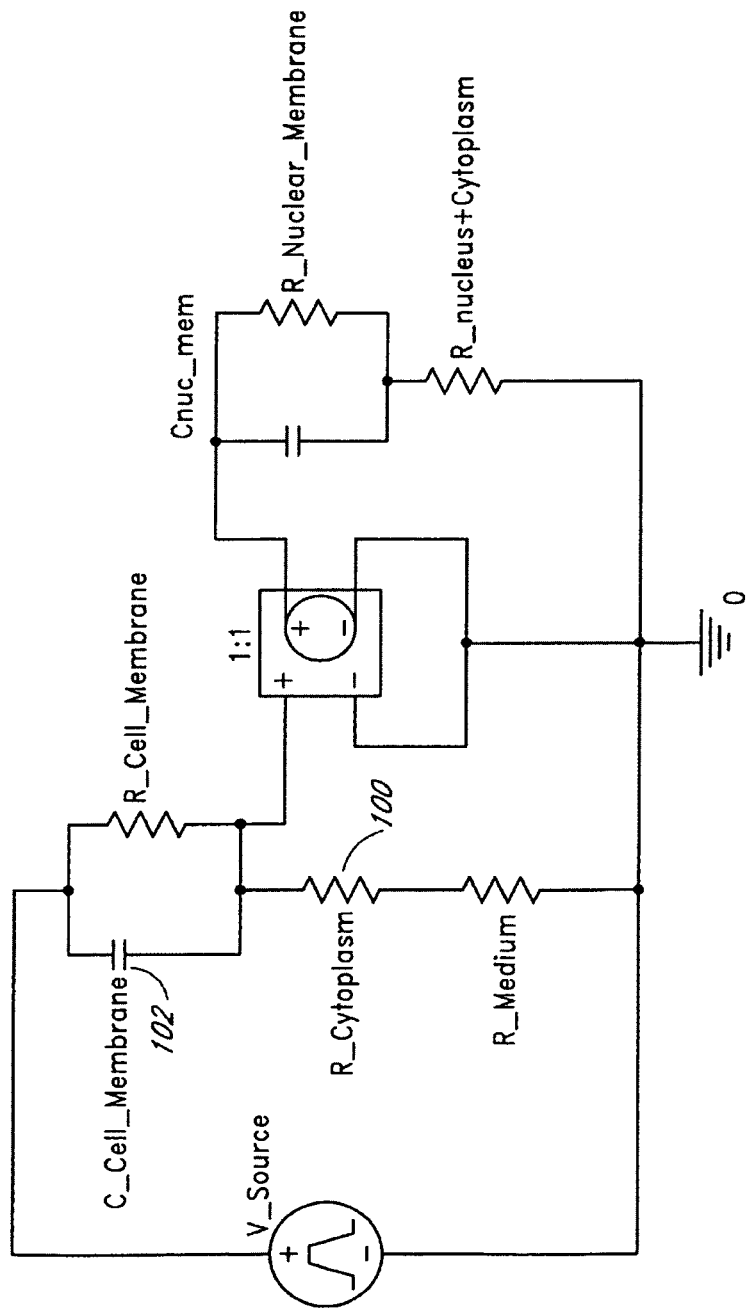
FIG. 18 illustrates a phenomenological lumped element circuit model of a biological cell.

In order to calculate the electrical response of a cell to a fast-rising, or short electrical pulse, phenomenological data for cell dielectric properties were incorporated as parameters in an electrical circuit model for a cell. The analysis, shown schematically in FIG. 16, shows that high frequency, or more precisely, fast-rising pulsed electrical fields, will introduce electric fields into the intracellular media of mammalian cells. The concept can be illustrated using simple lumped circuit elements (FIG. 17). Circuit parameters for the distribution of current flow for cells, membranes, etc. were estimated based upon published values (Kotnik, T., and D. Miklavcic. 2000. "Theoretical evaluation of the distributed power dissipation in biological cells exposed to electric fields", Bioelectromagnetics 21:385-394; DeBruin, K. A., and W. Krassowska. 1999, "Modeling electroporation in a single cell. I. Effects of field strength and rest potential", Biophysical Journal 77:1213-1224; Joshi, R. P., and K. H. Schoenbach. 2000, "Electroporation dynamics in biological cells subjected to ultrafast electrical pulses: a numerical simulation study", Physical Review E 62:1025-1033; Marszalek, P., D.-S. Liu, and T. Y. Tsong. 1990, "Schwan equation and transmembrane potential induced by alternating electric field", Biophysical Journal 58:1053-1058; and Freeman, S. A., M. A. Wang, and J. C. Weaver. 1994, "Theory of electroporation of planar bilayer membranes: predictions of the aqueous area, change in capacitance, and pore-pore separation", Biophysical Journal 67:42-56, all herein incorporated by reference).

Simulations performed in accordance with several embodiments of the current invention showed penetration of the intense, but low energy, electric fields to the interior of the cell. For these studies, an intracellular organelle was modeled as a small sphere (compared to cell radius) surrounded by a dielectric membrane, typically having a relative dielectric constant of 4 and a thickness of 5 nm.

Figure 19:
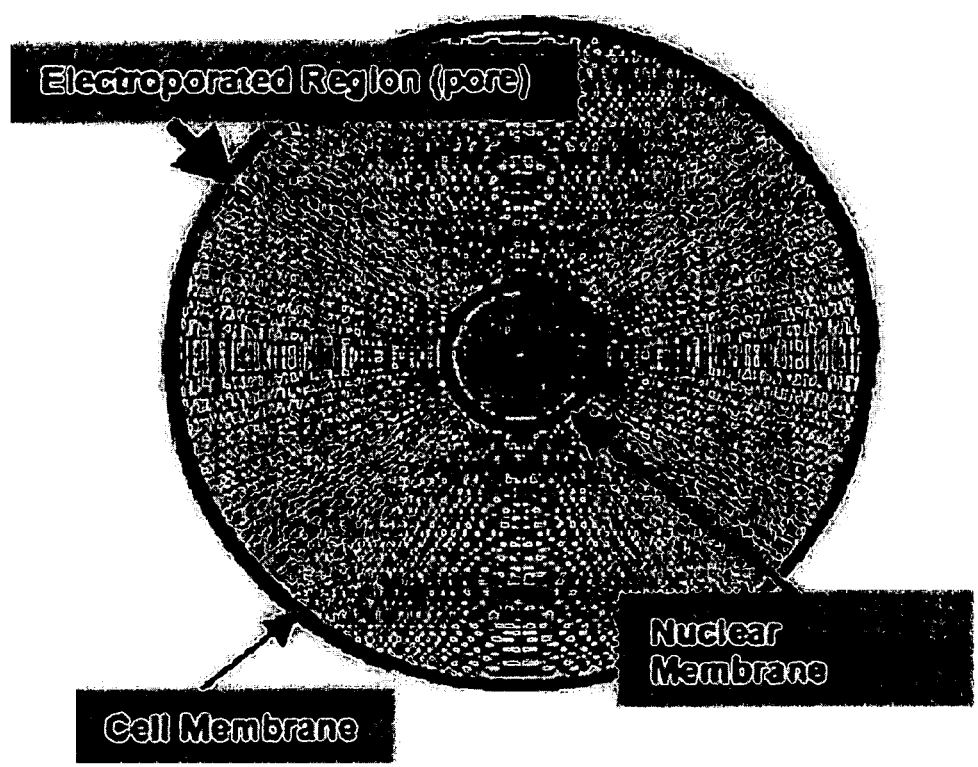
FIG. 19 is a 2-D simulation model showing a computational grid, where cylindrical or spherical symmetry can be modeled.
Figure 20:
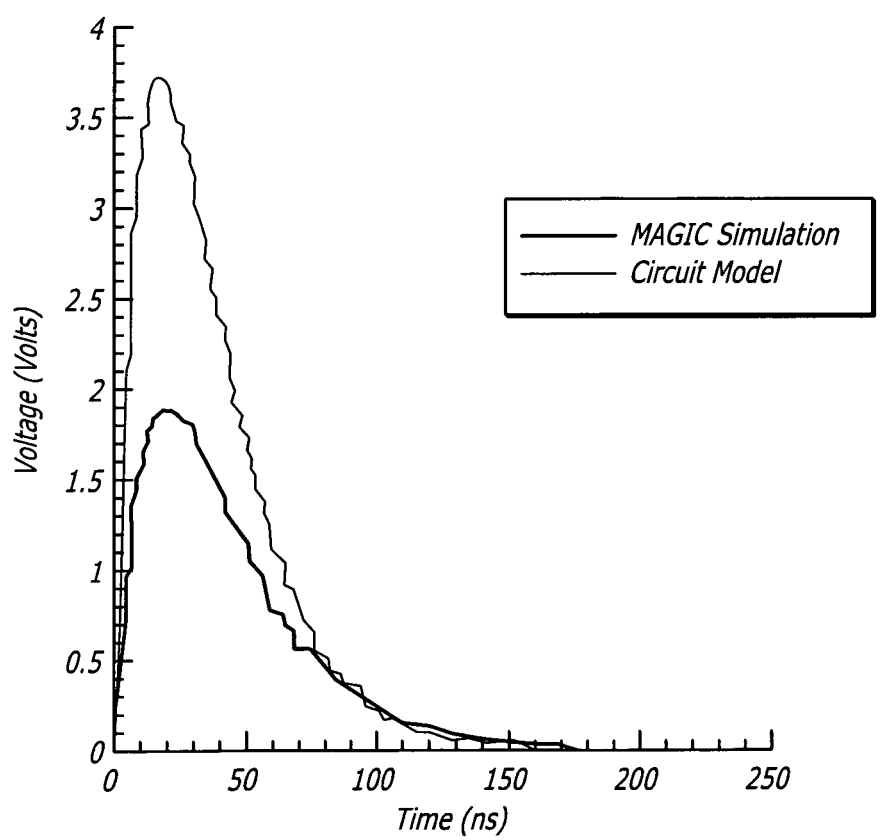
FIG. 20 is a graphical comparison of 2-D and circuit (1-D) models for nuclear membrane potential induced by an ideal pulse step.

The models provided a clear indication of conditions (pulse width, amplitude) under which field will perturb organelles within the cell. In order to develop an electromagnetic model with more detail than a lumped circuit element model, a finite difference time domain method was used. This method is particularly advantageous because it has the advantage of flexibility and a well-documented code, and is suitable for defining material properties. MAGIC software for electromagnetic calculations in the presence of conductive media, available from Mission Research Corp., was used in several embodiments of the present invention. However, one skilled in the art will understand that other similar software programs can also be used. Initially, the effects of the larger intracellular structures on the field distribution were determined using simulations with different sizes of mitochondrion membrane to compare differences between MAGIC and the circuit model. FIG. 19 and FIG. 20 show the results of MAGIC simulations. The voltage across the nucleus membrane from MAGIC simulations and the circuit simulation for a step pulse with 1 picosecond rise time and 160 V peak voltage applied to the cell are also shown. These results showed that including the geometric effects not present in the circuit model increased the electric field predictions in the interior membrane.

The shape, time duration and amplitude of the applied voltage were factors in cell electro-manipulation. The electrical and hence biological response of a cell differs based on its environment, the state of the cell in its life-cycle, the density of surrounding cells, and the geometry and type of cell (e.g., normal vs. tumorigenic; terminally differentiated vs. rapidly dividing). Thus, a realistic electrical model of the cell and its surroundings was useful in guiding experimental design and in interpreting the results.

In several embodiments of the current invention, various computational codes were used to determine cell modeling. The codes described herein are particularly were well-suited to the modeling of biological cells under the influence of pulsed voltages.

In one embodiment, the FDTD approach was used to determine the time-dependent response of the cell. Typically, short pulses have a broad frequency content, making harmonic methods less attractive. In addition, the framework of these codes provided an opportunity to use the resulting fields to "push" particles with appropriately modified force laws in electrically-gated channels. Moreover, the collision and ionization packages were straightforward to modify to model, for example, the electrically-catalyzed formation of key proteins in the mitochondrion. The codes were in 3-D, enabling the modeling of off-axis organelles and mitochondria that lack spherical symmetry. Another advantage of the codes used in several embodiments of the current invention include the ability of the codes to run on parallel platforms. This is particularly useful because the separation of spatial scales between the nanometer-scale cell membranes and the micron-scale cytoplasm and inter-cell spacings forces a small computational mesh or grid to resolve the smallest features and consequently an extremely large number of grids to cover the entire system.

In one embodiment, MAGIC was used. MAGIC is particularly useful because of its ability to handle materials with generalized dielectric constant and conductivity. However, one skilled in the art will understand that other software codes can also be used. The effects of cell geometry on the circuit properties of the system were modeled. A simple one-dimensional model having 4 layers corresponding to a cell membrane, cytoplasm, mitochondrion and mitochondrion membrane were used as an initial model. The MAGIC simulator was used to analyze the voltage drops across the different layers. The layers were assumed to have constant conductivity and permitivity. The 2-D model provided insight into the effect of cell geometry on the fields reaching into the nuclear membrane. (FIG. 19 and FIG. 20). There are a number of differences introduced by the more realistic geometry. First, as shown in FIG. 20, the 2-D MAGIC model yielded higher fields in the nuclear membrane by a factor of two. The deviation is due to the modification of the field in the cytoplasm by the non-negligible size of the nucleus. Second, the distributed model provided information about the amplitude and localization of fields in the cell not readily available from earlier models. An example is shown in FIG. 27 for a 50 nanosecond pulse at two different times. These data show the propagation of the field from the outer to inner membrane and the localization of the field in the nuclear membrane at t=50 nanoseconds.

MAGIC was used in 2-D to study in detail the spatial and temporal evolution of the electric fields in spherical cells. This complements laser techniques to spatially resolve the effect of the fields. The 2-D code was used to quantify the effect of size of the interior structure on membrane potentials and other factors. This system also allows investigations into off-axis structures (e.g., mitochondrial membrane potentials) with 3-D codes.

The effects of different cell environments on the electrical response of the cell were also analyzed according to several embodiments of the current invention. The conductivity and other properties of the surrounding fluid and tissue altered the circuit properties of the pulser-fluid-cell system and changed the optimization of pulser characteristics needed to achieve a given field in the cell interior. Once a biological response was optimized empirically using in vitro experiments, the simulations were then to used to predict the desired pulser characteristics needed to achieve the same intra-cellular fields under different environmental conditions (e.g., in different tissue, in vivo, etc.)

The effects of surrounding cells were also studied. In one embodiment, when the density of surrounding cells was high, the electric field penetration into an individual cell was modified by the surrounding cells. A 2-D periodic model was used to estimate the effect of these surrounding cells. This allowed the pulser design from the in vitro environment with widely spaced cells to be applied more readily to the in vivo environment of closely packed cells.

There are a number of physical situations that benefit from 3-D modeling. These include irregularly shaped cells, as well as off-axis organelles. The importance of the position of the mitochondria on the peak membrane potential it experiences was studied, for example, using 3D modeling. The state of the cell in its life cycle and changes in its electrical response were modeled. For example, during mitosis, microtubules become stretched and more fragile. Models of these aspherical shapes can be created with 3-D electromagnetic models.

Selectivity modeling was also used to differentiate normal vs. tumorigenic tissue, or terminally differentiated vs. rapidly dividing cells. One difference between the two cell types is the large number of mitochondria present in tumor cells. Thus, pulsed biases that act through modifying the mitochondrial membrane potential typically had a greater effect on tumor cells. However, the high density of mitochondria can alter the electric field structure in the cell.

In one embodiment, the electric field distribution of the applied fields was used to cause electroporation. Electrode designs, such as the electrode array geometry used in in vivo catheter experiments to simulate the effect of non-planar fields (gradients, etc.), were used to provide a desired field distribution (Gilbert, M. Jaroszeski, R. Heller, Biochimica et Biophys. Acta 1334, 9 (1997), herein incorporated by reference).

In one embodiment MAGIC in 3-D scaled simulations were used. In one embodiment, cell size was decreased while adjusting the conductivity and permittivity of the cytoplasm and membranes to preserve the time constant for charging the system. The computational time needed to model a single cell for 100 nanoseconds at full-scale in 3-D can be on the order of 104 CPU hours and the required memory can be on the order of 10 GBytes. To reduce computational requirements, the biological cell models were implemented on parallelized-PIC and reduced approximation (quasi-static) codes. The quasi-static codes take advantage of parallelized Poisson solver's to find the electrostatic field. The resulting currents were solved either by introducing a local conductivity or by pushing particles with appropriate mobility. The timestep was then advanced either by solving the continuity equation for the charge density or by using standard current deposition routines from the PIC algorithm. The models were solved on a Cartesian grid (of variable size in the case of MAGIC). In another embodiment, finite element approaches (e.g., tetrahedral mesh generators), such as FEMLAB, can also be used for reducing computation time.

Chemistry modules and non-linear physics modules were incorporated into the electromagnetic models. Electromagnetic models were interfaced with chemistry models developed for the electrically-gated production and transport of key ions and proteins. A force model was implemented in the "pusher" module of the particle-in-cell codes. Electrically gated chemical reactions were directly modified to the case of field-induced chemical production in biological cells by appropriately modifying the cross-sections and types of particles created.

The following Examples illustrate various embodiments of the present invention and are not intended in any way to limit the invention.

EXAMPLES

In one embodiment, dose-response and time course apoptosis-induction of UPSET on normal and tumor cell lines in vitro were provided. Repetitive 20 nanoseconds, 20 kv/cm pulsed electrical shock of Jurkat T cells at 20 hz led to a shock number-dependent apoptotic effect. Responses of the following terminally differentiated and rapidly dividing cell lines to the UPSET treatment were determined:

1. Jurkat T (ATCC#: TIB-152): In one embodiment, methods using these cells for ultrashort, pulsed electric shock induction of apoptosis are provided.
2. WERI-Rb-1 retinoblastoma cells (ATCC#: HTB-169): In one embodiment, this cell line is used to compare the response of the rapidly proliferating tumor cells with the retinoic acid (RA)-treated, terminally differentiated cells from the same cell lines. RA induces terminal cell differentiation in WERI-Rb-1 cells. This cell line and its global gene expression changes in response to RA during the cell differentiation process has been characterized.

3. C6/LacZ7 glioma cells (brain glial cells) (ATCC#: CRL-2303): This cell line is a subclone of the C6/LacZ cell line (ATCC#: CRL-2199), which was developed from the C6 rat glioma cell line (ATCC#: CCL-107). The C6/LacZ7 cells stably express the E. coli LacZ reporter gene, which can facilitate single tumor cell identification on tissue sections by histochemical stain. In one embodiment, these cells are used to study the therapeutic effect of UPSET on brain tumors in the rat glioma model.

4. DI TNC1 rat brain type 1 astrocytes (ATCC#: CRL-2005): This is one of very few normal brain cell lines available. The response of normal brain cells to the UPSET treatment are characterized and their responses compared with those of the brain tumor cell line C6/lacZ7 to define the appropriate shock parameters for in vivo use for brain tumor in the rat glioma animal model.

Cell Culture Protocol

In one embodiment, both the suspension cell lines Jurkat and WERI-Rb-1 and the adherent cell lines C6/LacZ7 and DI TNC1 are cultured following standard cell culture procedures and ATCC's instruction. All the tumor cell lines (Jurkat, WERI-Rb-1 and C6/LacZ7) are also be treated with appropriate concentrations of RA using an established protocol to induce each cell type to terminally differentiate (Li, A., Zhu, X., Craft, C. M., 2002. Retinoic acid upregulates cone arrestin expression in retinoblastoma cells through a Cis element in the distal promoter region. Invest Opthalmol V is Sci 43:1375-1383; Li, A., Zhu, X., Craft, C. M., 2003 (in press). Gene expression networks underlying retinoic acid-induced differentiation of human retinoblastoma Cells Invest Opthalmol V is Sci, in press, all herein incorporated by reference). Terminal differentiation of the cell phenotype is confirmed by morphological and cell cycle analysis through fluorescence-activated cell sorting (FACS) and global DNA microarray as described above.

UPSET Protocol

A protocol for UPSET treatment of the Jurkat cells is described above. The same protocol may be used for WERI-Rb-1 cells, because it is also a suspension cell line. For the adherent cell lines, the cells were detached with trypsin-EDTA, washed and resuspended in the appropriate growth medium before applying the shock treatment. The dose-response and the time course of the apoptotic effect and gene expression changes after the UPSET treatment were determined. The shock parameters that have the strongest apoptotic effect on the Jurkat cells may be characterized, and then the response of the normal brain cell line DI TNC1 and the RA-treated, terminally differentiated cells with the rapidly dividing tumor cells will be compared using these shock parameters.

Methods and Materials for Apoptosis Analysis:

Cell culture: Jurkat human T-lymphoblast (Weiss A, Wiskocil, R L, Stobo J D. 1984. J. Immunol. 133:123-128.) and Weri-Rb-1 retinoblastoma cells (American Type Tissue Culture, Rockville, Md.) were maintained in suspension culture in RPMI 1640 medium supplemented with 10% fetal bovine serum (FBS), 2 mM L-glutamine, 100 U/ml penicillin and 100 µg/ml streptomycin (growth medium) at 37° C. in an atmosphere containing 5% CO2.

UPSET treatment of the cells: Cells were seeded at rate $5 \times 10^5$ cells/ml and in a fresh RPMI growth medium, on the day before the experiment. Cells were harvested by centrifuging at 1,000 rpm for 3 minutes and resuspended in fresh RPMI growth medium to a final concentration of $2 \times 10^7$ cells/ml. Aliquots of 100 µl of cell suspensions were transferred into standard 1-mm gap electroporation cuvettes and subjected to repetitive ultra-short, pulsed electric shock treatment with a field strength of 40 kV/cm and a pulse duration of 20 nanoseconds using 0 (control), 2, 8, 20, and 50 monophasic pulses at room temperature. After shocking, the cells were transferred into 6-well tissue culture plates, diluted with RPMI growth medium to a final concentration of $1 \times 10^6$ cells/ml and incubated at 37° C. Aliquots of cell suspensions were taken at 0, 1, 2, 5, 8 and 24 hrs after shock for trypan blue exclusion/cell counting, annexin V binding-propidine iodide (PI) penetration assay, JC-1 staining and PARP cleavage assays. As a positive control for apoptosis, cells were treated with 0.0075% Triton X-100, which has been shown to induce apoptosis in a variety of cell lines (Borner M W, Schneider E, Pirnia F, Sartor O, Trepel J P, Myers C E. 1994. FEBS Lett. 353:129-132, herein incorporated by reference).

Annexin V apoptosis assays: The annexin V-FITC apoptosis detection kit I (BD PharMingen) was used to identify apoptotic cells. The assays were performed according to the manufacturer's instructions. Briefly, for each assay, about $4 \times 10^5$ cells (400 µl of cell suspension) were transferred from the above 6-well plates containing the treated cells into microcentrifuge tubes, washed once with cold PBS (200 g, 3 minutes) and resuspended in 300 µl of 1× binding buffer. One hundred microliters of resuspended cells was transferred into a culture tube and 10 µl combined annexin-V-PI solution was added. Samples were incubated in the dark for 15 minutes at room temperature, and 400 µl of 1× binding buffer was added to each tube. Samples were then analyzed by flow cytometry using a FacStar analyzer (Becton-Dickinson, San Jose, Calif.) within one hour. Results were processed using CellQuest software (Becton-Dickinson).

Analysis of Poly-ADP-ribose)-polymerase (PARP) cleavage: Poly-ADP-ribose-polymerase (PARP), a 113-kDa DNA binding protein, was cleaved into 89- and 24-kDa fragments during apoptosis, which could serve as an early specific marker of apoptosis. An anti-PARP polyclonal antibody (Roche Molecular Pharmaceuticals) was used to detect the cleavage of the 113-kDa PARP protein.

Protein immobilization: Cells ($5 \times 10^5$) were collected from the above 6-well plates 5 and 24 hrs after the shock treatments, washed with PBS, and sonicated 1 second×10 on ice in 100 µl of PBS. Equal amounts (50 µg) of proteins from whole cell homogenates were electrophoresed on 11.5% sodium dodecyl sulfate-polyacrylamide gel electrophoresis (SDS-PAGE) and were electrophoretically transferred to Immobilon-P membranes (Millipore, Bedford, Mass.) as previously described (Craft C M, Xu J, Slepak V Z, Zhan-Poe X, Zhu X, Brown B, and Lolley R N, 1998. PhLPs and PhLOPs in the phosducin family of G beta gamma binding proteins, Biochemistry 37:15758-15772, herein incorporated by reference). The immobilized immunoreactive proteins were detected on the membrane with anti-PARP (1:1, 000) followed with anti-rabbit secondary antibody, using an Enhanced Chemiluminescence Kit (Amersham).

Trypan blue exclusion and cell counting: During observation, cells were stained and inspected under an inverted microscope using trypan blue (Sigma-Aldrich). Normal cells are defined as those that are not stained. Stained cells reflect the uptake of dye due to a permeable outer membrane while normal live cells appear highly illuminated with clearly defined edges.

Preparation of Biotinylated Probes and Hybridization on Microarray: Affymetrix huGene FL™ arrays (Santa Clara, Calif.) containing 6800 genes were used for mRNA expression profiling. Total RNA was isolated from Jurkat T cells treated with 0, 8 or 50 ultra-short electric shocks with a field strength of 40 kV/cm and a pulse duration of 20 nanoseconds as described above. The cells were incubated in RPMI growth medium at a concentration of $1 \times 10^6$ cells/ml at 37° C. for 6 hrs before harvested for total RNA isolation. Double-stranded cDNA was prepared using the Life Technologies superscript choice system and an oligo(dT)24-anchored T7 primer. Biotinylated RNA was synthesized using the BioArray™ HighYield™ RNA Transcript Labeling Kit (Enzo Diagnostics, Inc. New York) following the manufacturer's instructions. In vitro transcription products were purified using the RNeasy Mini kit (Qiagen).

Affymetrix huGene FL™ array were hybridized with biotinylated in vitro transcription products (10 μg/chip) for 16 hrs at 45° C. using the manufacturer's hybridization buffer in a hybridization oven with constant rotation. The array then went through an automated staining/washing process using the Affymetrix fluidics station and was then scanned using the Affymetrix confocal laser scanner. The digitized image data were processed using the GeneChip software developed by Affymetrix.

Dose-response and time course of Jurkat cells in response to the UPSET treatment: 20 to 50 repetitive UPSET shocks of 20 kv/cm, 20 nanoseconds with a 3 nanosecond rise time at 20 Hz caused significant apoptosis and gene expression changes in Jurkat cells. To characterize the dose-response of the Jurkat cells to the UPSET shocks, parameters were changed sequentially one parameter at a time. The field strength in the range of 10 kv/cm to 300 kv/cm, the pulse width in the range of 0.1 nanosecond to 100 nanoseconds, and the pulse frequency in the range of 1 hz to 10 khz were tested. The pulse pattern and the rising time of the pulses were also examined.

The Jurkat cells were shocked at $2 \times 10^7$ cells/ml concentration in a standard 1-mm gap electroporation cuvette. After the shock, the cells were returned to culture dishes and incubated at 37° C. in a CO2 incubator. Aliquots of cells were taken and measured for apoptotic markers at 1, 3, 5, 8 and 24 hrs after shock. Apoptosis was detected with the annexinV/PI flow cytometer method to monitor PS translocation and integrity of the cell membrane, immunoblot analysis of the PARP cleavage, FITC-VAD-FMK stain to detect caspase activation, and genomic DNA isolated and analyzed by gel electrophoresis to determine the rate of DNA fragmentation. Also, real-time optical imaging of subcellular responses to the UPSET treatment were conducted. For example, the time course of changes in mitochondrial membrane, potential (depolarization) following exposure to apoptosis-triggering electric pulses were monitored by JC-1 staining, and cytochrome c release by mitochondria were analyzed using immunocytochemical, fluorescence-tagged, and microspectrophotometric analysis of cytochrome c distribution in cells exposed to ultrashort, high-field electric pulses. Release of cytochrome c from the mitochondrial intermembrane space was a recognized early event in apoptosis.

The responses not only of cell populations ($2 \times 10^6$ cells in an electroporation cuvette), but also of single cells (in groups of 10 or 20 cells) in nanoliter-sized microchambers are examined in order to determine the heterogeneity of the responses of members of a cell population to pulsed electric fields. The microchamber containing 10-20 cells in a single row is electric shocked on the objective stage of a microscope, and the real-time response of the cells to the shock is recorded by real-time optical imaging.

Gene Expression Regulation by UPSET Treatment:

In one embodiment of the resent invention, global DNA microarray analysis of pulse-treated Jurkat cells revealed up-regulation and down-regulation of specific genes by the UPSET treatment. The time course of gene expression changes were analyzed following the apoptosis-inducing shock treatment. Also, the up-regulated and down-regulated genes in the above cell lines were compared to determine whether or not the shock treatment specifically activates or inactivates certain genetically programmed pathways. The Affymetrix oligo array technology and the human gene full-length array containing about 6,800 human genes was used for these analyses. However, one skilled in the art will appreciate that other array technologies can also be used. Although not wishing to be bound by the following theory, it is believed that specific pathways of early gene activation are involved in later downstream activation/inactivation of signal transduction pathways leading to apoptosis. Proteomic analysis with mass spectroscopy (MALDI) was also performed, where the role of the newly identified proteins and their posttranslational modifications from pathways of the identified transcribed genes were characterized by the Affymetrix Genechip technology.

The apoptotic responses of the four different cell lines above are compared. First, the normal brain cell line DI TNC1 and the tumor cell lines Jurkat, WERI-Rb-1 and C6/LacZ7 are shocked with the most effective apoptosis-inducing parameters defined for Jurkat cells and are tested for the appearance of apoptotic markers at various time points after shock. Jurkat, WERI-Rb-1 and C6/LacZ7 tumor cell lines are then treated with RA to induce cell differentiation. The suspension cell lines are treated in suspension and the adherent cells in attachment cultures. Terminal differentiation of each cell line is confirmed by morphological and cell cycle analysis using the FACS method. The treated, terminally differentiated and untreated cells were shocked and apoptosis induction is examined.

In one embodiment, the therapeutic effects of UPSET are analyzed in an in vivo animal model of brain cancer. In one embodiment, the rat glioma animal model is used (DeAngelis, M. 2001. Brain Tumors New England Journal of Medicine 344:114-123. See also Watanabe, K., Sakamoto, M., Somiya, M., Amin, M R, Kamitani, H, Watanabe, T. Feasibility and limitations of the rat glioma model by C6 gliomas implanted—at the subcutaneous region. Neurol Res 2002. 24(5):485-90; and Barth, R F. Rat brain tumor models in experimental neuro-oncology: the 9L, C6, T9, F98, RG2 (D47), RT-2 and CNS-1 gliomas. J Neurooncol. 1998. 36(1):91-102, all herein incorporated by reference). Using the in vitro data (i.e. for rat glioma cells and normal astrocytes) as a foundation, the effects of UPSET in C6 glioma cells are studied in situ by placing a microcatheter directly within the tumor to deliver the pulses. A time course study is conducted to assay the tumors for induction of apoptosis using a variety of histochemical measures, including the FITC-VAD-FMK stain to detect caspase activation and the TUNEL method to detect DNA fragmentation. Both caspase activation and DNA fragmentation are demonstrated in in vitro experiments during UPSET induction of apoptosis in C6/LacZ7 cells and other cell lines. In one embodiment, the animal model allows evaluation of the UPSET technology in the normal brain and provided a method for investigating neurotoxicity of UPSET. This novel technology has important therapeutic relevance as an adjunct to surgical therapy, where delivery of UPSET pulses to the surgical resection cavity following tumor removal can lead to improved local disease control. In one embodiment, the stereotactic placement of a microcatheter to deliver an electric pulse directly to a surgically inaccessible tumor in the brain will complement stereotactic radiosurgery or be used instead of stereotactic radiosurgery.

The biological effects of ultrashort, high-field electric pulses in vitro using a well-established glioma cell line C6/LacZ7, as well as a normal brain astrocyte cell line D1 TNC1, are studied. The parameters derived from these in vitro investigations form the basis for further in vivo study using C6/LacZ7 cells. Here, the therapeutic effects of UPSET are evaluated in both an intracranial and a flank model of rat glioma using C6/LacZ7 cells. The flank model provides ready access to the C6/LacZ7 tumors, which grow as a solid mass in the subcutaneous tissue. The flank model provides an advantage over the intracranial model in that animals with intracranial masses typically die within 3 weeks. The flank model is used to investigate the response of C6 tumors to UPSET pulses, define the optimal working parameters and assess the apoptotic response and then transition to the intracranial model to evaluate UPSET in the setting of a brain tumor. The LacZ marker of the tumor cells provides single tumor cell identification on tissue sections.

In one embodiment, Wistar rats are injected with 100,000 C6/LacZ7 cells subcutaneously in the flank. The tumors are allowed to grow to approximately 1 cm3. The tumors are exposed and the microcatheter device are directly placed into the tumors for both the control and the experimental groups of the rats. Tumors of the experimental group are treated with the ultrashort high electric field pulses delivered through the microcatheter device, while the control group is not treated. Tumor tissues are harvested for histological and immunohistochemical analysis for apoptotic markers (FITC-VAD-FMK stain to detect caspase activation and TUNEL stain to detect DNA fragmentation), as well as tumor cell markers (LacZ) at various time points (hours to days). The sizes of the tumors are also measured. The cells that are positive for apoptotic markers are significantly increased in the treated animal group as compared to the untreated group. In contrast, the sizes of the tumors in the treated group are significantly decreased compared to the control group. Through repeated application of the UPSET treatment, removal of the tumors is provided according to several embodiments of the current invention.

In one embodiment, for intracranial studies, animals are stereotactically injected with 100,000 C6/LACZ7 cells into the right parietal lobe of the brain. After 10 days, the animals are re-anesthetized, and using the original bony openings, the microcatheter device is placed directly into the tumor for delivery of ultrashort high field electric pulses. Half of the animals are treated with the UPSET as the experimental group, and the other half is not be treated and thus serves as a control group. At various time points (hours to days) after the pulse treatment, the animals are sacrificed and the brains are harvested for histology and immunohistochemical analysis, as described above for the flank studies. There are fewer LacZ-positive cells and more apoptotic cells in the experimental group than in the control group. Although not wishing to be bound by the following theory, it is believed that the LacZ-positive tumor cells are killed through apoptosis induction without extensive injury of the normal brain tissues by repeated pulse treatment or by controlling the pulse dosage (repetitive pulses for each treatment).

Combination Therapy

In one embodiment, a method of sensitizing a eukaryotic cell to a therapeutic agent is provided. In one embodiment, at least one electric field pulse is applied to a cell to produce a sensitized cell. Each electric field pulse has a pulse duration of less than about 100 nanoseconds. In one embodiment, at least one electric field pulse has a pulse duration of less than about 10 nanoseconds. In another embodiment, the pulse duration is less than about 1 nanosecond. One or more therapeutic agents is applied to the sensitized cell and the effect of the therapeutic agent is enhanced in the sensitized cells. Therapeutic agents include, but are not limited to, nucleic acids, polypeptides, viruses, enzymes, vitamins, minerals, antibodies, vaccines and pharmaceutical agents. In one embodiment, the pharmaceutical agent is a chemotherapeutic compound. One skilled in the art will understand that one or more therapeutic agents can be applied to the cell and that these agents can be applied before, after or during sensitization of the cell. In one embodiment, the pulse duration is less than about 1 nanosecond and the electric field is greater than about 10 kV/cm.

In another embodiment, a method of sensitizing a eukaryotic cell to a therapeutic method is provided. In one embodiment, at least one electric field pulse is applied to a cell, wherein each electric field pulse has a pulse duration of less than about 100 nanoseconds, to produce a sensitized cell. One or more therapeutic methods is then applied to the cell. The effect of the therapeutic method is enhanced in the sensitized cells. Therapeutic methods include, but are not limited to, photodynamic therapy, radiation therapy and vaccine therapy. One skilled in the art will understand that one or more therapeutic methods can be applied to the cell and that these methods can be applied before, after or during sensitization of the cell. In one embodiment, at least one electric field pulse has a pulse duration of less than about 10 nanoseconds. In one embodiment, the pulse duration is less than about 1 nanosecond and the electric field is greater than about 10 kV/cm.

III. Cellular Marking

In several embodiments of the current invention, a method is provided in which one or more electric field pulses are applied to a cell to mark or target the cell for diagnostic or therapeutic procedures. In one embodiment, at least one electric field pulse is applied to one or more cells. At least one electric field pulse has a pulse sufficient to induce a cellular response in said cell, wherein the cellular response marks the cell for diagnostic or therapeutic procedures. In a further embodiment, the duration of each pulse is less than about 100 nanoseconds. In one embodiment, at least one electric field pulse has a pulse duration of less than about 10 nanoseconds. In another embodiment, the pulse duration is less than about 1 nanosecond. In one embodiment, the cell is "marked" by affecting one or more characteristics of the cell, including but not limited to, gene transcription, gene translation, protein synthesis, post-translational modifications, protein processing, cellular biosynthesis, degradative metabolism, cellular physiology, cellular biophysical properties, cellular biochemistry and cellular morphology. In one embodiment, the cellular response induced by the electric field pulse includes the inversion of the phosphatidylserine component of the cytoplasmic membrane of the cell. In another embodiment, intracellular membranes including, but not limited to, the cytoplasmic membrane, nuclear membrane, mitochondrial membrane and segments of the endoplasmic reticulum are affected. In one embodiment, the diagnostic or therapeutic procedure includes lysing the cell.

In another embodiment of the present invention, a method of disrupting an intracellular membrane of a eukaryotic cell is provided, including, but not limited to, the cytoplasmic membrane, nuclear membrane, mitochondrial membrane and segments of the endoplasmic reticulum. In a further embodiment, at least one electric field pulse is applied to a cell at a voltage and duration sufficient to induce disruption of the intracellular membrane. In a further embodiment, each electric field pulse has a pulse duration of less than about 100 nanoseconds. In another embodiment, the duration is less than about 1 nanosecond. In a further embodiment, the electric field is greater than about 10 kV/cm. Disruption of the intracellular membrane includes, but is not limited to, translocating membrane components. These components include, but are not limited to, phospholipids, including phosphatidylserine, proteins or other components. One skilled in the art will understand that translocating membrane components includes inverting or rearranging one or more membrane proteins, phospholipids, etc.

In another embodiment of the present invention, a method of marking a eukaryotic cell for phagocytosis is provided. In a further embodiment, at least one electric field pulse is applied to a cell at a voltage and duration sufficient to induce a cellular response in the cell, wherein the cellular response marks the cell for phagocytosis. The cellular response includes, but is not limited to, translocating membrane components. These components include, but are not limited to, phospholipids, including phosphatidylserine, proteins or other components. In a further embodiment, each electric field pulse has a pulse duration of less than about 100 nanoseconds. In one embodiment, the duration is less than about 1 nanosecond. In another embodiment, the electric field is greater than about 10 kV/cm.

In one embodiment, cells are exposed to one or more pulsed electric fields, as described above. These pulses cause translocation of the membrane phospholipid phosphatidylserine to the outer leaflet of the cytoplasmic membrane, which is assayed as described above. Rearrangement of other components of the cytoplasmic membrane are detected by the fluorescent microscopic or flow cytometric observation of migration of fluorescent-tagged membrane lipids and proteins, or by changes in binding of fluorescent-tagged antibodies to membrane constituents.

IV. Cell Tolerance

It is yet another object to provide a method in which one or more electric pulses are applied to a cell to determine cellular tolerance to electric pulses. In one embodiment, a first electric field pulse is applied to one or more cells, and electroperturbed cell are identified, isolated and assayed for one or more indicators of cellular response. Then, a second electric field pulse that is not equal to the first electric field is applied to the cells. After this second treatment, the electroperturbed cell are again identified, isolated and assayed for one or more indicators of cellular response. The indicators of cellular response after application of the first electric field are compared with the indicators of cellular response after application of the second electric field. The indicators of cellular response include, but are not limited to, changes in gene transcription, gene translation, protein synthesis, post-translational modifications, protein processing, cellular biosynthesis, degradative metabolism, cellular physiology, cellular biophysical properties, cellular biochemistry and cellular morphology. Methods of applying electric pulses to cells and methods of determining cellular responses to these pulses are performed in a manner similar to that described above. Clinical applications in accordance with several embodiments of the current invention include the assessment of cellular tolerance to radiation emissions from cellular phones and to microwave radiation.

V. Selective Electroperturbation

In several embodiments of the current invention, a method is provided to selectively electroperturb a population of cells based upon the cell's dielectric constant. In one embodiment, the dielectric constant is exploited to selectively reduce proliferation of rapidly dividing cells in a patient. In one embodiment, dielectric properties of one or more cells in two populations of cells is determined. An electric field pulse based on these dielectric properties is then determined, wherein the electric field pulse selectively electroperturbs the first sub-population of cells without substantially affecting the second population of cells. This electric field pulse is then applied to the cells. The first sub-population of cells includes, but is not limited to an abnormal or unhealthy cells, such as rapidly dividing cells. The second population of cells includes cell that are to remain unaffected by the electric pulse, such as terminally differentiated cells. In another embodiment the first sub-population of cells includes one type of rapidly dividing cell and the second population of cells includes a second type of rapidly dividing cell. In a further embodiment, the electroperturbation induces changes in a cellular response, including, but not limited to, changes in gene transcription, gene translation, protein synthesis, post-translational modifications, protein processing, cellular biosynthesis, degradative metabolism, cellular physiology, cellular biophysical properties, cellular biochemistry and cellular morphology. Methods of applying electric pulses to cells and methods of determining cellular responses to these pulses are performed in a manner similar to that described above.

In another embodiment, a method of selectively regulating gene transcription in rapidly dividing cells is provided. In this embodiment, a group of cells, containing both rapidly dividing cells and terminally differentiated cells, is obtained and at least one electric field pulse is applied to the cells. Each electric field pulse has a pulse duration and intensity sufficient to induce gene transcription primarily only in the rapidly dividing cells.

In one embodiment, dielectric properties of a given cell type include critical voltage and charging time constants for external and internal membranes. Because of the complexity of the extracellular and intracellular environments, these are determined empirically for each cell type. The critical voltage, or the voltage at which a large increase in membrane conductance is observed, is determined by loading the medium (extracellular or intracellular, depending on the membrane being characterized) with a membrane-impermeant fluorochrome, and observing at which point in a stepped-voltage sequence the membrane becomes permeable. In some cases, it is desirable or necessary to use a patch-clamp measurement of the pulse current across the membrane.

In another embodiment, one or more dielectric permittivities and conductivities of membranes and extracellular and intracellular fluids, from which the charging time constant are derived, is determined by time domain dielectric spectroscopy as described in Poleyva, Y., I. Ermolina, M. Schlesinger, B.-Z. Ginzburg, and Y. Feldman, Time domain dielectric spectroscopy study of human cells II. Normal and malignant white blood cells, Biochim. Biophys. Acta 1419: 257-271, 1999, herein incorporated by reference. Once the dielectric properties of a given cell population are known, pulse amplitude, duration, and sequence may be tailored to the critical voltage and charging time constant of the target structures. In one embodiment, structures with shorter time constants and lower critical voltages are selectively affected by pulses which are too short and-or too low in amplitude to disturb other structures.

VI. Treating Target Tissues

In several embodiments of the present invention, a therapeutic method is provided in which a patient's tissue is removed and subsequently treated with one or more electric field pulses. In one embodiment, a method of reducing proliferation of rapidly dividing cells in a patient is provided, in which a portion of a patient's tissue that contains rapidly dividing cells and terminally differentiated cells is removed. At least one electric field pulse is applied to one or more cells in the tissue, wherein each electric field pulse has a pulse duration of less than about 100 nanoseconds. The tissue is then reintroduced to the patient. The tissue includes, but is not limited to, blood, cerebrospinal fluid, lymphatic fluid and bone marrow. In one embodiment, at least one electric field pulse has a pulse duration of less than about 10 nanoseconds. In another embodiment, the pulse duration is less than about 1 nanosecond. In one embodiment, electric field pulses greater than about 100 nanoseconds in length are combined with pulse durations of less than 100 nanoseconds.

In another embodiment, a method of reducing proliferation of rapidly dividing cells in a patient is provided. In one embodiment, a target cell population in the patient is identified, where the cell population includes rapidly dividing cells and terminally differentiated cells. At least one electric field pulse is applied to a portion of the target cell population, thereby reducing proliferation of the rapidly dividing cells in the target population. Each electric field pulse has a pulse duration of less than about 100 nanoseconds. In one embodiment, at least one electric field pulse has a pulse duration of less than about 10 nanoseconds. In another embodiment, the pulse duration is less than about 1 nanosecond. Electric field pulses greater than about 100 nanoseconds in length can also be combined with pulse durations of less than about 100 nanoseconds. In one embodiment, the rapidly dividing cells are tumorigenic cells. In another embodiment, the terminally differentiated cells are non-tumorigenic cells.

In a further embodiment, a method of treating a tumor in a patient is provided. In one embodiment, one or more tumor in a patient is identified. A catheterized electrode is then applied proximate to the tumor. The catheterized electrode is capable of providing at least one electric field pulse. One or more one electric field pulses is then applied to a portion of the tumor, thereby treating said tumor. Each electric field pulse has a pulse duration of less than about 100 nanoseconds. In one embodiment, at least one electric field pulse has a pulse duration of less than about 10 nanoseconds. In another embodiment, the pulse duration is less than about 1 nanosecond. Electric field pulses greater than about 100 nanoseconds in length can also be combined with pulse durations of less than about 100 nanoseconds. In one embodiment, treating the tumor includes reducing the proliferation of rapidly dividing cells in the tumor. In one embodiment, the catheterized electrode is coupled to an endoscope. In another embodiment, the catheterized electrode is applied to the patient in conjunction with an endoscopic procedure.

VII. Combined Long and Short Pulse Technology

It is another object of several embodiments of the current invention to provide a method in which at least two electric field pulses are applied to a cell to facilitate entry of a diagnostic or therapeutic agent into a cell's organelles. In one embodiment, a "long" electric field pulse is applied to cell followed by a "short" electric field pulse. In one embodiment, the method includes applying at least one first electric field pulse to the cell sufficient to cause electroporation, incubating the cell with the therapeutic agent, and applying one or more second electric field pulses to one or more cells in the tissue, wherein each second electric field pulse has a pulse duration of less than about 100 nanoseconds. The therapeutic agent includes, but is not limited to, nucleic acids, polypeptides, viruses, enzymes, vitamins, minerals, antibodies, vaccines and pharmaceutical agents. In a further embodiment, the pulse duration of the "short" pulse is less than about 1 nanosecond and the electric field is greater than about 10 kV/cm. In another embodiment, the pulse duration of the "long" pulse is greater than about 100 nanoseconds. The application of electric pulses to cells and the evaluation of cellular responses to these pulses are performed in a manner similar to that described above.

In one embodiment, the long pulse, or series of pulses, permeabilizes the external membrane, and serves as a conventional electroporating pulse. Amplitude, duration, and sequence for this pulse, or series of pulses, are determined by the cell type and medium as described above. The short pulse, or series of pulses, facilitates entry of the therapeutic agent into an intracellular structure, which may or may not require permeabilizing the internal membrane. Pulse parameters are determined by the methods described above and optimized empirically for each agent and cell type.

VIII. Identification of Therapeutic Agents

In one embodiment of the present invention, a method of identifying an effective therapeutic agent is provided. In one embodiment, at least one putative therapeutic agent is applied to a cell. The regulation of at least one cell-cycle control gene, stress-response gene or immune response gene is then determined. If at least one of these genes is up-regulated, the putative therapeutic agent is identified as an effective therapeutic agent. Such an agent can be an effective therapeutic agent in reducing cell proliferation. Agents that induce apoptosis can also be identified in accordance with several embodiments of the current invention. In one embodiment, the cell-cycle control genes, stress-response genes or immune response genes include, but are not limited to ASNS, CHOP (GADD153), CLIC4, CD45, CD53, p36, CD58, AICL FOS, FOSB, DUSP1, JUN, TOB2, GADD34, CLK1, HSPA1B, JUND, EGR1, CACNA1E, CD69, ETR01, ITPKA, AHNAK, EMP3, ADORA2B, POU2AF1, AIM1, ATP1G1, ASNS, ETS2, CD45, VIM, TGIF, LAT, CLIC4, SLC7A5, ZFP36L2, RUNX1, SLC3A2, IFRD1 and PrP.

In one embodiment, the putative therapeutic agent includes, but is not limited to, nucleic acids, polypeptides, viruses, enzymes, vitamins, minerals, antibodies, vaccines and pharmaceutical agents.

Broadband Power Measurement of High-Voltage, Nanosecond Electric Pulses

Experimental studies have shown that nanoelectropulses of sufficiently short rise time and duration can trigger apoptosis (programmed cell death). Specifically, pulses with a duration less than 20 ns have been shown to kill a wide variety of human cancer cells in vitro as well as induce tumor regression in vivo. To better understand the mechanisms by which nanopulses affect cancer cells, the electrical characteristics of the cells should be characterized so that it is clear how electrical energy is delivered.

A power measurement device that integrates into a nanopulse transmission line used for in vivo experiments has been designed, built, and calibrated. The device provides broadband voltage and current measurements without disturbing the transmission of the pulse to the biological sample. The fidelity of pulse is preserved by using a 50Ω microstrip line that provides a proper impedance match between the measurement device and the transmission line. As the pulse travels along the microstrip line, the voltage is measured by a high impedance voltage divider, and the current is measured by a current transformer. Depending on the way in which the measurement device is integrated into the transmission line, the electrical impedance of the in vivo sample can be characterized either by a direct voltage/current measurement or by measuring the incident and reflected voltage pulse and using time domain reflectometry to calculate the impedance. The bandwidth of both the microstrip line and the voltage attenuator has been measured to be 1 GHz and 500 MHz respectively.

Figure 42:
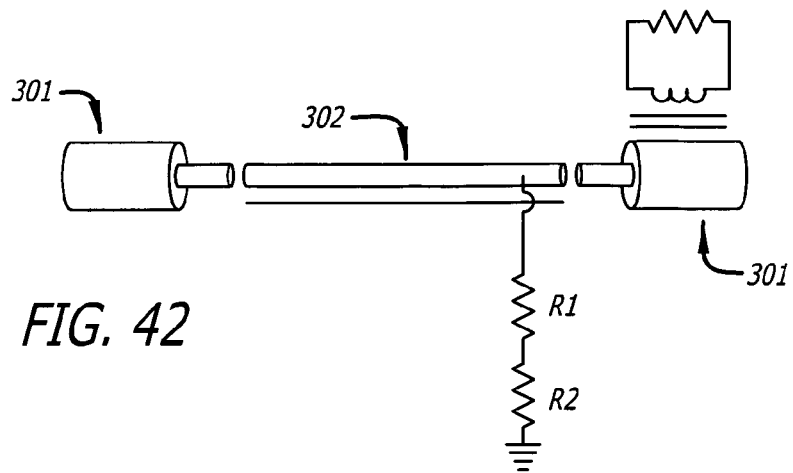
FIG. 42 depicts a voltage/current measurement device.

FIG. 42 displays an alternative embodiment of a present voltage/current measurement device set up. To obtain broadband performance for high voltage pulses, SHV (Safe High Voltage) connectors 301 were soldered onto the input and output lines of a 50Ω microstrip line 302, which is a transmission line usually used in RF designs. To prevent high voltage flashover at the input and output of the strip, approximately ⅛" of the ground plane was cut away at the input and output. The width of the line that would provide a 50Ω match was obtained from the following equations:

$$\frac{w}{h} = 0.6366 \left\{ B - 1 - \ln(2B - 1) + \frac{\epsilon_r - 1}{2\epsilon_r} [\ln(B - 1) + 0.39] \right\} \quad (16)$$

$$B \quad (17)$$

Measurement data included in the next section shows that the width of 0.135" obtained from the calculation provides a good match with a 3 dB bandwidth of 1 GHz.

Attenuation of the pulse was obtained with a voltage divider, which has the following transfer function:

$$\frac{V_o}{V_i}(S) = \frac{R_2}{R_1 + R_2} \quad (18)$$

$$\tau_1 \quad (19)$$

$$\tau_2 = R_1 \| R_2 (C_1 + C_2) \approx R_2(( \quad (20)$$

Figure 43:
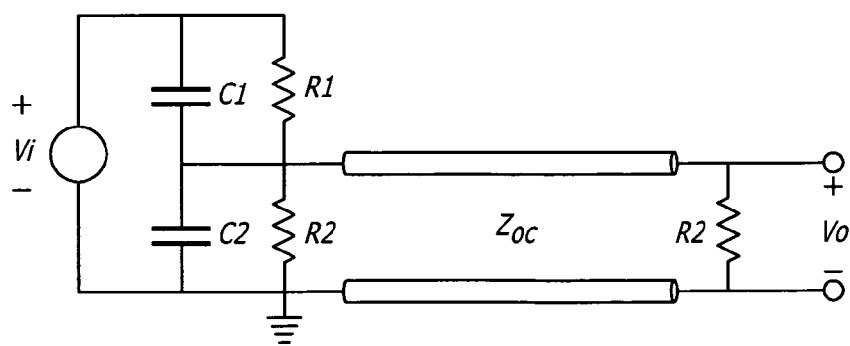
FIG. 43 depicts an attenuator network wherein C1 and C2 are the parasitic capacitances that limit the bandwidth

The time constant $T_1$ dominates the frequency response because R1=2.5 kΩ which is so much larger than R2=50Ω (FIG. 43). As a result, the attenuation falls off with increasing frequency and has a 3 dB bandwidth of 500 MHz.

Measurement Results

Figure 44:
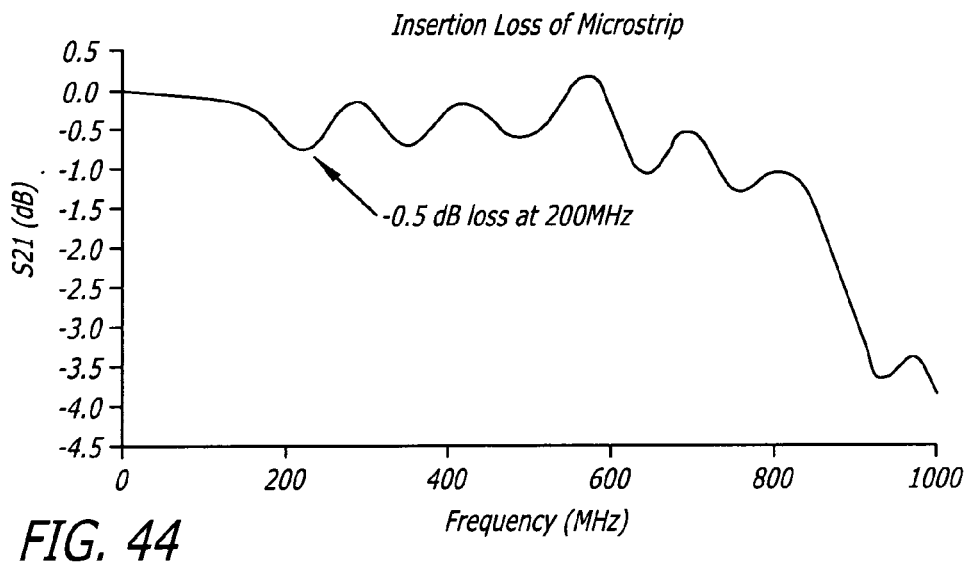
FIG. 44 depicts the plot of the insertion Loss of the measurement Box.
Figure 45:
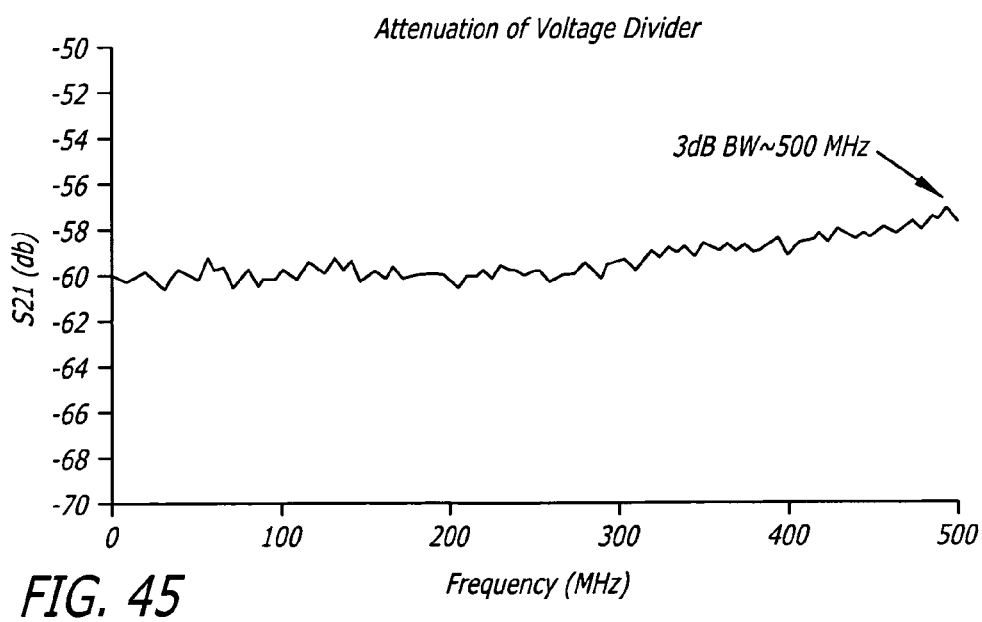
FIG. 45 depicts the plot of attenuation of the voltage divider augmented with a commercially available 20 dB attenuator.

The plots of FIGS. 44 and 45 illustrate the insertion loss and attenuation of the measurement device, respectively. FIG. 45 depicts the plot of attenuation of the voltage divider augmented with a commercially available 20 dB attenuator.

Figure 46:
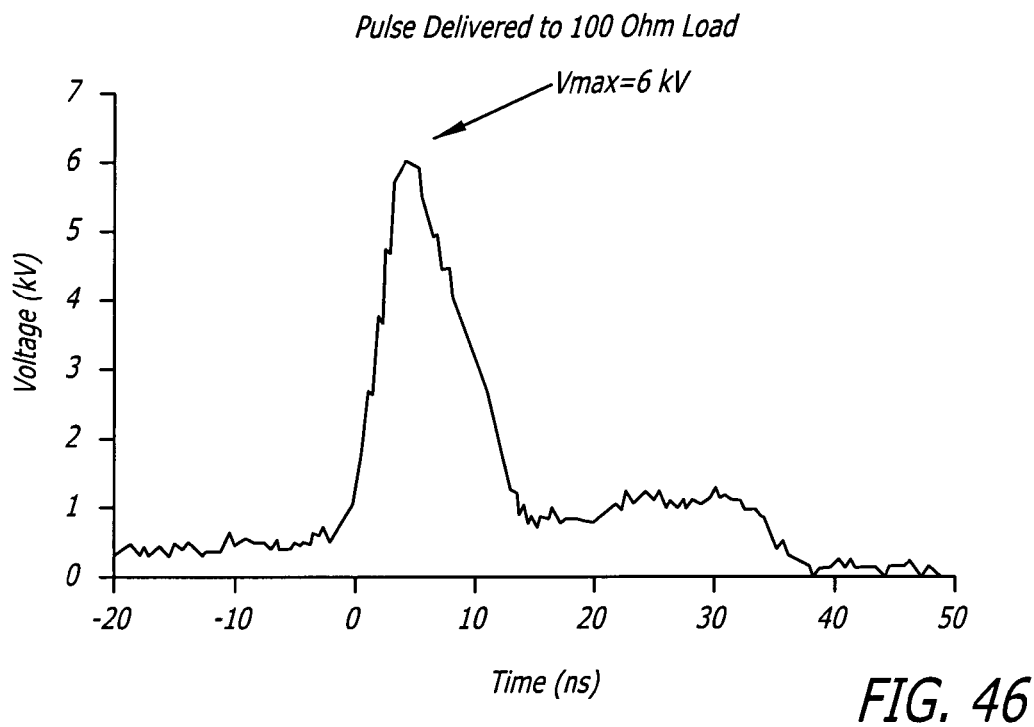
FIG. 46 depicts a plot of output pulse measured with the inserted VI measurement box.
Figure 47:
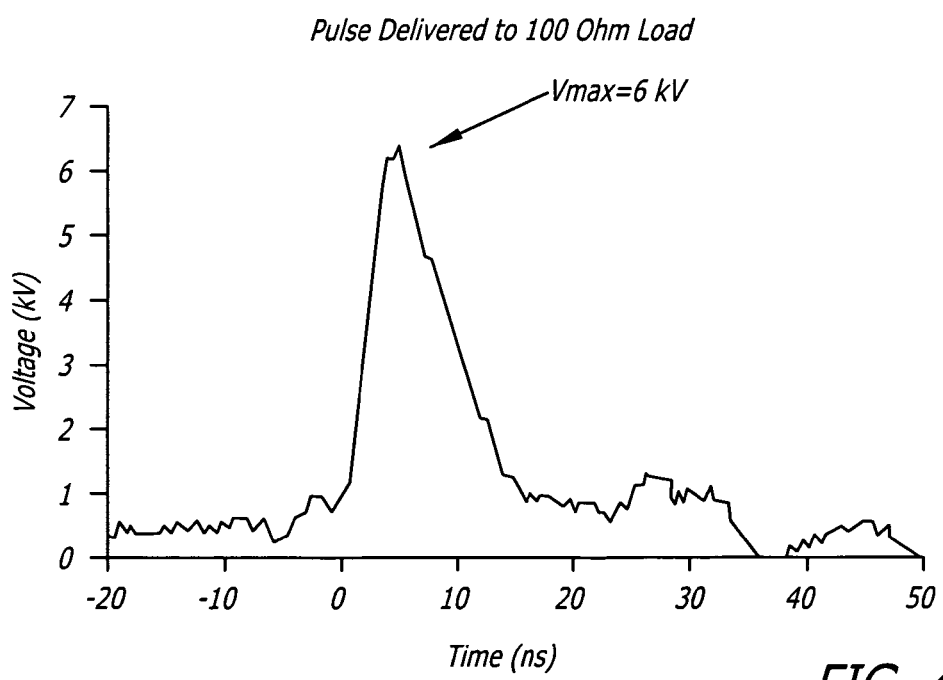
FIG. 47 depicts a plot of output measured with the VI measurement box replaced with a cable union.

The next two plots of FIGS. 46 and 47 are of time-domain measurements that verify that the insertion loss due to the measurement device for a 5 ns pulse (fo=200 MHz) is about 0.5 dB. A 3' cable connected the output of the pulser to the input measurement device, and a 6' cable connected the output of the measurement box to a 100Ω dummy load. Two measurements were taken: one with the measurement device inserted between the two cables and one with the measurement device replaced by a female-female union. A Tektronix high voltage probe was used to observe the pulse delivered to the load.

A quick calculation reveals that the attenuation that occurs due to the insertion loss of the measurement device is 0.42 dB, which is consistent with the frequency measurement shown above.

System Architecture and Placement of the Detection Circuitry Along the Transmission Line in a Medical Device for Use in Clinical Treatments The circuits described to sense and deliver accurate waveform measures can effectively be located in one or more of a few points in the treatment system.

The pulses are typically generated in a system component called a pulse generator, which drives the pulses down an impedance controlled cable and into the portion of the device which contacts the patient via electrodes and delivers the treatment in the form of these pulses into the tissue near the contact point. The cable and portion of the device which contacts the patient is referred to here as the "delivery system". The delivery system may include a "wand" or handle component which would allow the clinician to effectively place the electrodes onto the patient during treatment.

The pulse generator is typically controlled by a microprocessor-based control unit referred to here as the "controller". The software which runs in the controller serves to provide control signals to the pulse generator and other system components (such as power supply, display, user interface, etc.) to deliver varied treatments based on control of pulse parameters, such as strength or power level, timing, duration of pulses, number of pulses, etc. These settings can either be set explicitly by a clinician or calculated by the system itself based on a combination of entered, system-resident (e.g. tables), sensed and calculated values.

The locations at which the output can be sensed via the voltage divider circuit for measuring delivered voltage, and the current loop circuit for sensing delivered current, include the output of the pulse generator, along the delivery system cable, including the entry into the "wand" portion of the delivery system, or very near to the electrodes at the end of the system. These points are indicated in FIG. Placing the sensed portion very near the electrodes have the advantage of combining any reflections in the system along with the transmitted energy, and thus providing the most accurate real time reading nearest the patient tissue.

All things being equal, while it may be best from a measurement integrity standpoint to position both the voltage and current sensing circuits closest to the electrodes, this may not be possible due to sizing, interface restrictions, potential issues with interference and maintenance of the recorded voltages back up the delivery system cable. Placing the detection circuits at the output of the pulse generator is perhaps an easier solution in that there is no need to cable the circuitry external to the unit, but would serve to include the reflected portion of the signal at a later time point in the reading and this would have to be taken into account and potentially "looked for" by the processing elements which will ultimately use the measured data in the system.

When placed either on a printed circuit board at the output of the pulse generator, or a small circuit board or other discrete implementation in the delivery system, the stripline approach is a useful and important design element to include to both ensure minimal disruption to the delivery of the pulses to the patient and to get an accurate reading with controlled attenuation over the frequency bands of interest.

System Applications

A voltage-current monitor which can accurately reflect the pulse characteristics in real time, with little distortion and very flat attenuation across a broad spectrum is very useful for monitoring the integrity of pulse delivery into a patient for medical applications.

The pulses captured by the monitor circuit would be useful in a number of areas at the system level:
1. Ensuring the system was functional, delivering pulses as indicated for the treatment, and able to reach the full voltage and current levels, within some acceptable tolerance, for the desired level of treatment
2. Counting the actual pulses delivered or the net energy transferred in treatment to a particular site, which could be noted in a patient record or used to determine a course of treatments over multiple sessions. This treatment record particular to a patient could be maintained in the system, and along with some measure of the condition being treated being input by the clinician or otherwise available to the system, could support the system calculating and delivering a regimen for adjusting these pulses on subsequent visits to the same area
3. Ensuring the delivery system was in good contact with the tissue of the patient, as the peak current and its timing with respect to the voltage output is dependent upon this contact. Having this information as the treatment is delivered would let the clinician know whether the delivery system needs to be adjusted relative to the patient or not. These cues for adjusting the position of the delivery system could come in several forms, including but not limited to auditory form, via a display component in the system, or via vibratory feedback to the delivery system wand or handle which could be sensed by the clinician in real time Data Handling and Use of the Measured Pulse Characteristics From the voltage and current waveforms which have been sensed by the monitor circuit, one or more of the following paths could be taken in recording and handling the information from the waveforms—
1. In either the voltage or current signals, peak detection and subsequent analog to digital conversion would result in useful peak values of each to system software. These could be correlated in time, also, in the analog domain, which would yield additional information for the above applications.
2. The waveforms could be integrated over an appropriate time interval in the analog domain and used for a "net energy delivered" calculation with the final integrated value(s) digitized and made available to software for additional processing and the above applications.
3. The entire waveform, or critical portions of it could be sampled and digitized at a high rate (100K samples/second or higher) and stored in memory, made available to system software for more sophisticated digital processing to provide fine detail over critical portions of pulse delivery for use in more sophisticated algorithms A hybrid method of analog detection circuitry to detect these critical sections and trigger the high rate of sampling or potentially to provide for more strategic, limited lower rate sampling could also be employed.

Pulsed Power for Biology/Cell Electromanipulation

Ultrashort high field pulses are another exemplary embodiment that can be effective in electroperturbation of cancer cells. The ultrashort pulses may require subnanosecond rise time, high voltage pulses delivered to low impedance biological loads. Here we present an exemplary embodiment of a compact solid-state pulse generator developed for this application.

The pulse can be generated by switching a chain of avalanche transistors configured as a tapered transmission line from high voltage to ground. The system may feature a built in 1400:1 capacitively compensated resistive voltage divider. The divider, with a 3 dB point at 910 MHz, may overcome challenges in the direct measurement of the high frequency components of the output pulse. The generator can produce a 0.8 ns rise time, 1.3 ns wide, 1.1 kV pulse into a 50$\Omega$ load at a repetition rate of 200 kHz.

Intracellular electro-manipulation may require subnanosecond high voltage pulses delivered to low impedance biological loads. We present here the design and construction of an experimental setup that can deliver such subnanosecond high voltage pulses to biological cell solutions. This low-parasitic electronic setup interfaces our avalanche transistor-switched pulse generation system with the imaging and monitoring apparatuses used that can be used for bio-photonic studies of pulse-induced intracellular effects.

The setup features a custom fabricated microscope slide to hold the cell solution under study, and a printed circuit board designed that can carry the output pulse from the pulse generator to micro-machined electrodes on the glass slide. The pc-board and the slide are designed that can match the load impedance of the pulse generator. This may minimize reflections back into the pulse generator, and minimizes distortion of pulse shape and pulse parameters. Further, the pc-board contains a custom-made high bandwidth voltage divider that can allow for real-time monitoring of pulses delivered to the cell solution.

We have designed a viable interface to deliver high voltage subnanosecond pulses from a compact solid-state pulse generator to low impedance biological loads. The interface consists of a micro-machined glass slide that may contain the cells under study; and a low-parasitic pulse delivery system designed that can be used as an impedance matching network. The system can carry an undistorted subnanosecond pulse to a cell solution load on the microscope slide. This setup, along with the subnanosecond pulse generator, a high bandwidth voltage monitor and a microscope imaging system may be used to conduct biophotonic studies of intracellular effects induced by subnanosecond high voltage pulses.

Ultra-short, high-field strength electronic pulses may be used in the electroperturbation of biological cells. The voltage induced across a cell membrane may depend on the pulse length and pulse amplitude. Pulses longer than ~1 $\mu$s may charge the outer cell membrane and lead to opening pores, either temporarily or permanently. Permanent openings may result in cell death. Pulses of a length much shorter than ~1 $\mu$s can affect the cell interior without adversely affecting the outer cell membrane.

Pulses lasting a few nanoseconds and with a 2-10 MV/m amplitude may be used to trigger intracellular calcium release, translocate phosphatidylserine (PS) across the cell membrane, cause chromatin rearrangement and induce programmed cell death (apoptosis) in malignant cells without permanently damaging the outer cell membrane. These effects have, among other things, generated interest in the electromanipulation of intracellular structures for inducing apoptosis and understanding gene transfection mechanisms.

Subnanosecond Pulse Generation for Electromanipulation

Shorter and higher amplitude electronic pulses are useful for cell biology research to probe and manipulate intracellular structures such as nuclei and mitochondria. Effective manipulation of intracellular structures using electropulses requires pulses that are short enough to bypass the cytoplasmic membrane and deposit their energy across intracellular membrane-bound structures.

According to molecular dynamics simulations, electropulses that can create transmembrane fields of the order of 5-20 MV/m (i.e. transmembrane potential of >1 V) cause nanometer-diameter pores to form in the phospholipid bilayers within 1-2 ns of application. This indicates that subnanosecond risetime 5-20 MV/m pulses could minimize nanoporation of the cell membrane, enable the voltage across the inner membranes to exceed that across the outer membrane, and allow intracellular electromanipulation to dominate over membrane effects.

Intracellular electro-manipulation experiments aimed at understanding the biological effects and clinical implications of electroperturbation require subnanosecond high voltage pulses delivered to low impedance biological loads.

Ultrashort high voltage pulse generation technology for low impedance biological cell loads is limited to 3-4 ns 10 MV/m pulses. Their pulse width and rise time are well above the time required for nanometer diameter pores to form in the phospholipid bilayers of the outer membrane, and thus not suitable for comprehensive studies of intracellular electromanipulation.

The main constraints imposed by the need to apply <1 ns at >1 kV pulses to biological cell solution loads are:
1) Using ultrafast high power switches (for the high field short pulse generation)
2) System should be compact and robust (need for solid state choices instead of spark gaps and gas switched generators) to interface easily with an in vitro or in vivo biological test setup. Further, pulse generator should have high repetition rate (several kilohertz) so as to facilitate observation of the effects of many pulses on the cells with good statistics.
3) Low impedance of the biological load under study (order of magnitude), and possible variability of this load. Further it is hard to characterize the exact impedance of a biological cell solution under study—so we want a pulse generation system capable of driving a variable, complex low impedance load.

Subnanosecond High Voltage Pulse Generation Architectures

Radio frequency MOSFET switched capacitors have also been used to generate ultra-short pulses. However, MOSFET switched capacitors may not be able to generate pulses that are narrower than 15-20 ns. This may be due to complications of MOSFET driving circuits and inherent limitations of many MOSFET devices.

Switching diodes with saturable transformers is another pulse generation technique. These pulse generators are based on diode opening switch and saturable core transformer. This design may be limited to 2>ns rise time because of inherent limitations in the diode switching characteristics.

Other switches have been used having similar limitations wherein the best rise times may have been over 2 ns for ~1 kV.

Spark gap switched transmission lines for generating ultra-short pulses may be physically large and have only a low repetition rate. They may also have only a relatively short lifetime, and provide erratic pulses with a large amount of jitter. The transmission line capacitance may also need to be charged rapidly in order to overvolt the spark gap to meet a fast rise time requirement.

A high repetition rate subnanosecond high voltage pulse generation systems have been developed for high impedance loads like the Pockel's cell. However, given the high frequency components in the pulse, small mismatches between the generator and the load could lead to high frequency ringing, reflections and result in the pulse energy not being delivered to the load.

In an exemplary embodiment of the present invention we present a pulse generator that is capable of delivering approximately the same pulse regardless of the variability of the impedance of the cell solution (different cell solutions can have different impedances).

Thus we present a compact, robust, high field sub-nanosecond electric pulse generation techniques with high repetition rate capabilities for low impedance biological loads to facilitate manipulating intracellular biomolecular structures.

Measurement of Subnanosecond High Voltage Pulses

The high voltage needs to be divided before it is fed into an oscilloscope for measurement in order to avoid instrument damage. Commercial oscilloscope voltage probes for high voltage applications are designed to withstand low frequency and DC high voltage signals. However, measurement of high voltage pulsed power requires resolution of the high frequency characteristics of the pulse. Thus a voltage divider may have a very high bandwidth, and tolerate very high instantaneous power for low duty cycles.

Measurement of subnanosecond high voltage pulses may need ~1 GHz bandwidth in order to resolve the subnanosecond rise time. Voltage division techniques that are purely based on inductive coupling or capacitive compensation may be impractical because of limitations imposed by self resonant frequencies of circuit components.

PC-Board parasitics combine the challenges of direct measurement of kilovolt transitions in hundreds of picoseconds. The lack of reliable broadband voltage dividers has caused other avalanche transistor pulse generator designers to infer output pulse characteristics using indirect methods such as quantifying the effect on the load and back-calculating pulse parameters.

However, in our application, it is important to know the pulse parameters in order to understand the effects on the load (the biological cell solution under study). Hence back-calculation is not an option. Further, it is important for our experiment to have an online voltage measurement device that measures the voltage and current delivered to the load, as the pulse is delivered so that the cellular responses can be interpreted continuously. Thus there is a need to develop a custom radiofrequency voltage division technique that is applicable to such electrobiological experimental setups.

In an exemplary embodiment we have designed an avalanche transistor switched pulse generation system that can produce 1.1 kV pulses, a rise time of 0.8 ns, and pulse width of 1.3 ns into a low impedance biological load, at a repetition rate of tens of kilohertz (i.e. 200 kHz). The system may consist of the pulse generator, a high bandwidth voltage monitor to measure pulses delivered to the load, a setup to interface the pulse generator with a biological cell solution under microscopic observation, and a microscope imaging system that may be used for biophotonic studies of intracellular effects induced by subnanosecond high voltage pulses.

Pulse Generator Design

A) Avalanche Transistors or Switching Setup

Existing pulse generators used in ultra-short pulse electroperturbation research are based on diode opening switch and saturable core transformer based designs. These designs are limited to >2 ns rise times because of inherent limitations in the diode switching characteristics. Avalanche transistors, with nonlinear high gain characteristics, have been known to switch in the 100 s of picosecond regime, and were therefore chosen to be suitable for our design goals [5,6]. Like in [5], we chose SOT-23 Zetex FMMT417 avalanche transistors because of their high VCBO rating (320 V) and compact low inductance packaging. Further, these transistors have a peak collector current rating of 60 A for pulses shorter than 20 ns and are therefore more than well suited to our peak current requirement of 25 A.

B) Trigger Circuit

Figure 48:
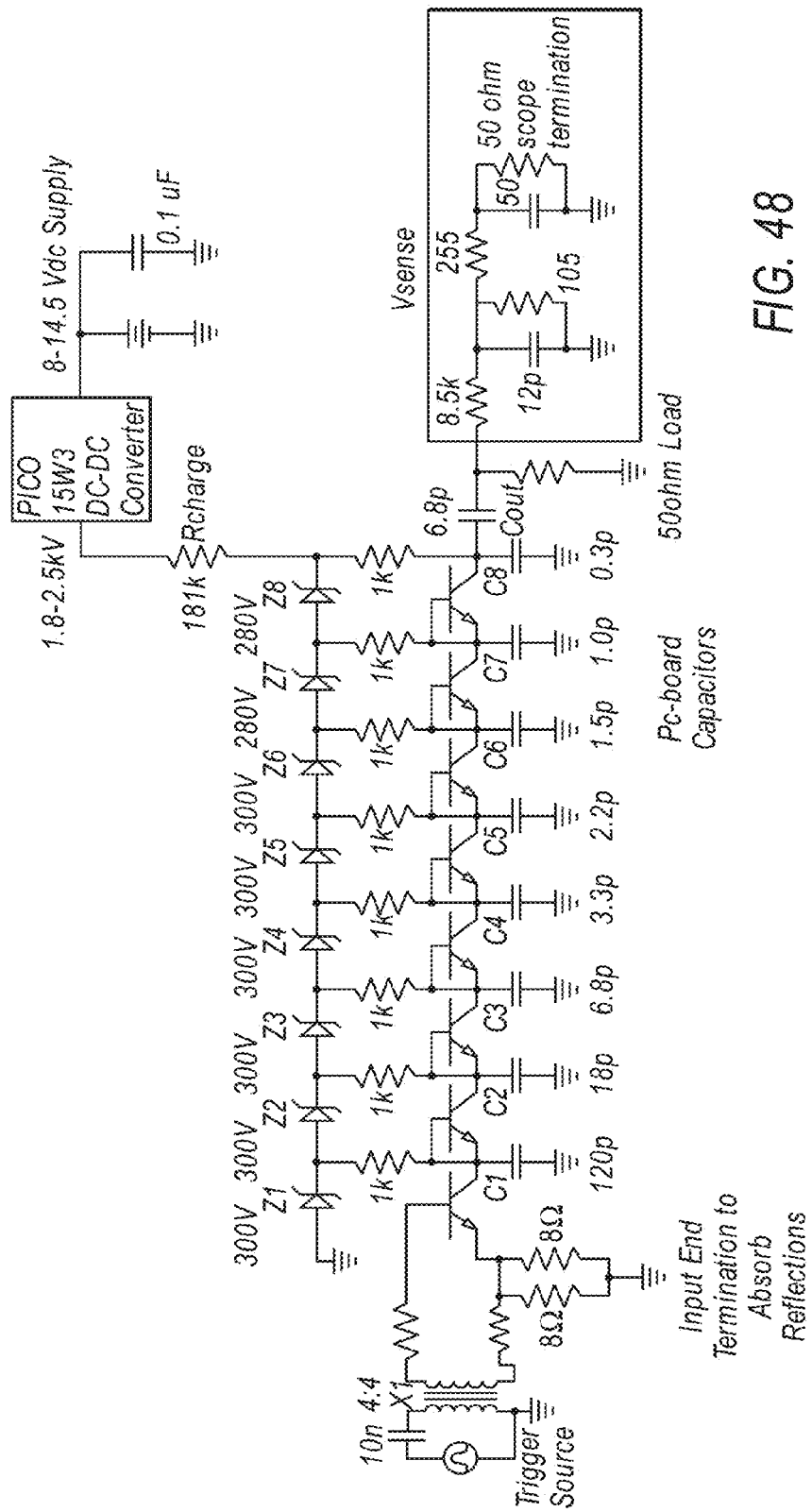
FIG. 48 depicts a complete avalanche pulse generator circuit.

In the exemplary embodiment the basic pulse generating circuit can be a series chain of avalanche transistors and capacitors configured as a tapered transmission line from high voltage to ground. The circuit diagram is shown in FIG. 48. The line is switched from high voltage to ground by triggering the bottom of the transistor cascade via an amorphous saturable core TX1 from Toshiba.

This choice of design can ensure every stage avalanches faster than the previous stage i.e. that the rise time sharpens progressively through the pulse generator.

Before the circuit is triggered, the first transistor appears to have an open base and a common emitter. Therefore it is more prone to $V_{CEO}$ than a shorted base-emitter type $V_{CBO}$ breakdown. The $V_{CEO}$ breakdown occurs at a lower voltage of 100 V and is characterized by current runaway. The avalanche breakdown is more desirable because it lets us hold off a much higher voltage ($\sim V_{CBO}=320$ V) across the first transistor. Moreover a $V_{CBO}$ avalanche breakdown of the first transistor generates the charge carriers needed to cause the succeeding stages to avalanche. To force the first low-side transistor into $V_{CBO}$ avalanche breakdown, the trigger signal may force the base to be shorted to the emitter. This can be achieved by driving $TX_1$ to saturation—i.e. by having a trigger signal that is short and rises as fast as 0.5-1 ns.

Pulse generation and sharpening mechanism: The line may be switched from high voltage to ground by triggering the bottom of the transistor cascade via an amorphous saturable core, and forcing the lowest end avalanche transistor into VCBO breakdown. This breakdown can generate an avalanche current necessary to force successive higher end stages into non-destructive avalanche breakdown. Successive stages can avalanche faster and faster to give an output pulse rise time of the order of 100 s of picoseconds. The fall time may be controlled by choosing an output capacitor such that the load-output capacitor time constant is small enough to obtain an output pulse with width ~1 ns.

C) Tapered Transmission Line Lay Out

A tapered transmission line is used to ensure that the rise time sharpens progressively from stage to stage. The rise time can sharpen progressively only if every stage avalanches faster than the previous stage i.e. if each stage has a greater over voltage across it than the previous stage. Since it is a series chain, current through each stage remains approximately the same. Therefore, successive stages are designed to have higher impedance than the preceding ones, with the first stage having the lowest impedance.

The low impedance of the 1st stage causes its collector to be placed close to ground upon triggering. Since stage 1 goes into avalanche breakdown upon triggering, it feeds in the avalanche current necessary to turn on stage 2 and overvolt it. Since stage 2 has higher impedance than stage 1, there is a larger over voltage across stage 2 than across stage 1. This causes stage 2 to go into faster non-destructive avalanche breakdown than stage 1. Stage 2 then feeds in avalanche current to stage 3, causing it to turn on faster and go into an even faster avalanche breakdown. Successive stages avalanche faster and faster in a similar fashion to cause C8 to discharge into ground within several 100 picoseconds.

This gives us an output pulse rise time of the order of 100 s of picoseconds. By choosing Cout such that $R_{load}*C_{out}$ is small, we can control the fall time and obtain a sub-nanosecond output pulse. Since the impedance of each succeeding stage is less than that of preceding stages, the effective transmission line impedance, $Z=\sqrt{(L/C)}$, is tapered so the lower end stages have higher capacitances. This helps keep the avalanche current on until the higher end stages have turned on. The capacitance for the first stage is chosen so as to allow it to switch 200 V within a rise time of 1 ns. Since the desired current in the chain is 25 A, the capacitance C1 is given by:

$$C1=\Delta Q/\Delta V=I\times dt/dV=25\ A\times 1\ ns/200V=125\ pF \quad (21)$$

The closest commercially available value is 120 pF. Modeling the Zetex transistor as having an inherent inductance of L=2 nH, and using the formula $Z=\sqrt{(L/C)}$, C1=120 pF gives a first stage impedance of 4Ω. The impedance of the line must therefore taper uniformly from 4Ω at the triggered end to the 50Ω load impedance at the high end.

A preliminary characterization of the FMMT 417 transistors revealed that about half of the DC voltage across any transistor would be applied to the load when the transistor is in avalanche mode. But to keep transistors out of their breakdown region, the DC voltage across every transistor is limited to VCBO=320 V. Therefore the number of stages for a 1.25 kV output pulse is given by:

$$N=V/(0.5*VCBO)=1250/160=7.8\square 8 \quad (22)$$

It is desirable to keep the tapering smooth so as to avoid significant reflections due to abrupt impedance jumps. So to taper from 4Ω to 50Ω in 8 stages, we can estimate a linear impedance taper of (50-4)/7=6.6Ω per stage. This lets us calculate the capacitances C2-C8, as shown in Table 1 of FIG. 49. All capacitors used are NPO type (American Technical Ceramics) ATC 100C capacitors rated at 2500 V. They are chosen since they are ultra low ESR components that have very low variability (~5%) over the rated voltage range.

Since the resulting configuration is a discretely tapered transmission line with finite impedance jumps, reflections are unavoidable. Reflections degrade the output waveform by causing a jittery rising edge and a long tail. Reflections also degrade the transistors over time. Therefore, we have placed two paralleled input termination resistors each having a value of 8Ω to match the impedance of the triggered end and absorb any reflections.

This technique forces the line to behave like a two-end terminated coax cable. It ensures a smooth rise, and improves reliability of the pulse generator by ensuring that reflections going back and forth will not re-trigger the transistors.

D) DC Charging Circuit

Forcing transistors into VCBO breakdown may require them to be DC-biased to the VCBO voltage. Thus, all the transistors in the line may have a DC bias of 280-320 V. The dc bias for the transistor chain may need to be divided uniformly among the 8 stages. If some transistors have higher dc collector to emitter bias than others, they may turn on due to dc overvoltage and the circuit produce pulses spuriously before an external trigger signal is supplied. The symmetry of DC bias and voltage division may be achieved by using a chain of high voltage zener diodes across the 8 transistors in our circuit.

The dc bias for the transistor chain needs to be divided uniformly among the 8 stages. If some transistors have higher dc collector to emitter bias than others, they turn on due to dc overvoltage and the circuit produces pulses spuriously before an external trigger signal is supplied. The symmetry of voltage division is achieved by using a chain of high voltage zener diodes ($Z_1$-$Z_8$). Avalanche pulse generators may have 320 V zener diodes to ensure that transistors are not biased beyond their $V_{CBO}$ rating.

In practice, however, this choice of zener diodes is not completely effective in maintaining equal dc voltage bias across all 8 transistors. In order for all 8 diodes to hold off their nominal voltages, the zener chain needs to conduct a nominal current, $I_z$ of 1-1.2 mA from high voltage end to ground. However, if the nominal zener voltage is high enough for the transistors to 'turn on' under dc collector to emitter bias, the higher end transistors will draw significant leakage current from the zener chain. Leakage of current from the zener diode chain at the high end causes insufficient current supply to the lower end diodes. This prevents the lower end diodes from maintaining their nominal zener voltages. Thus most of the 2.5 kV dc supply is dropped across the higher end transistors, and very little across the lower end transistors. This has two effects: a) the lower end transistors cannot avalanche when triggered, because they do not have a high enough dc collector to emitter bias to drive them into $V_{CBO}$ breakdown; b) the higher end transistors are overvolted well beyond their $V_{CBO}$ rating and avalanche unpredictably without any external triggering. The above problems clamp the peak output pulse voltage to ~1.25 kV—which is about half of the design value because only the higher half of the transistor chain is contributing to the output pulse.

Figure 50:
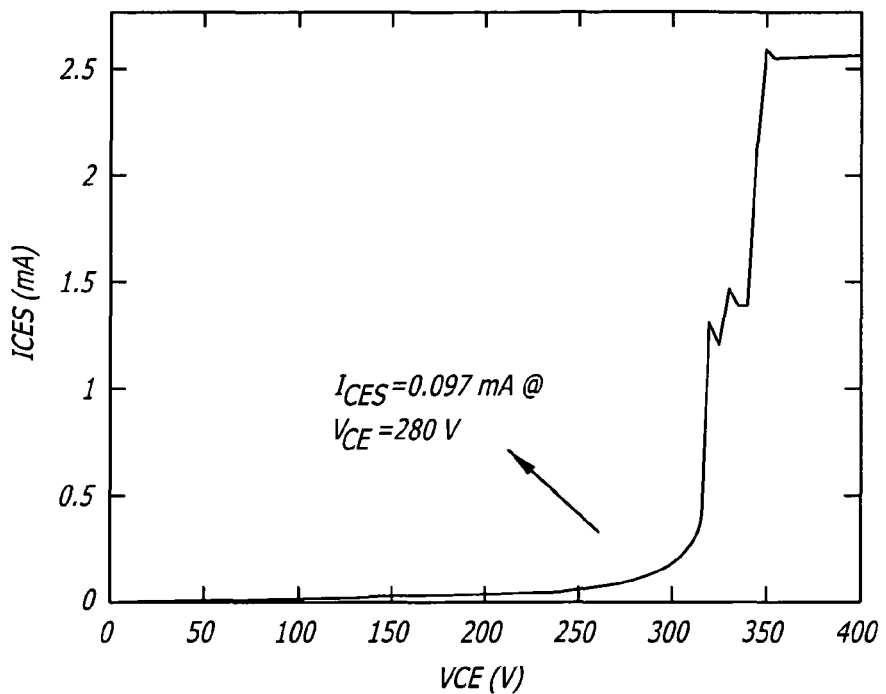
FIG. 50 depicts an empirically obtained leakage curve for the zetex FMMT 417 avalanche transistor −Ices is a collector to emitter current under reverse collector to emitter voltage=Vce when base is shorted to emitter.

In an alternative embodiment we present here using 280-300 V zener diodes instead of the obvious choice of 320 V overcomes this problem. A characterization of leakage current versus voltage showed that the transistors start drawing significant leakage currents (currents greater than ⅒ of the nominal $I_z$ i.e. ~100 μA) from the zener chain if they have a dc VCE greater than 280-300 V (FIG. 50).

Further, since the higher end capacitors charge up before the lower end capacitors, and the higher end zeners turn on before the lower end ones, it is important to make sure that the higher-end transistors have lower dc reverse collector to emitter bias than transistors on the low voltage end of the chain. This ensures that the high-end transistors may only turn on due to a non-destructive avalanche breakdown triggered by the lower end transistors, and not by spurious dc overvolting. Therefore, the zener diodes across the 2 highend transistors have been chosen to be 280 V rated 1N5109 components, as opposed to the other 6—which are 1N5110 components rated at 300 V.

E) Control of Parasitics

Figure 51:
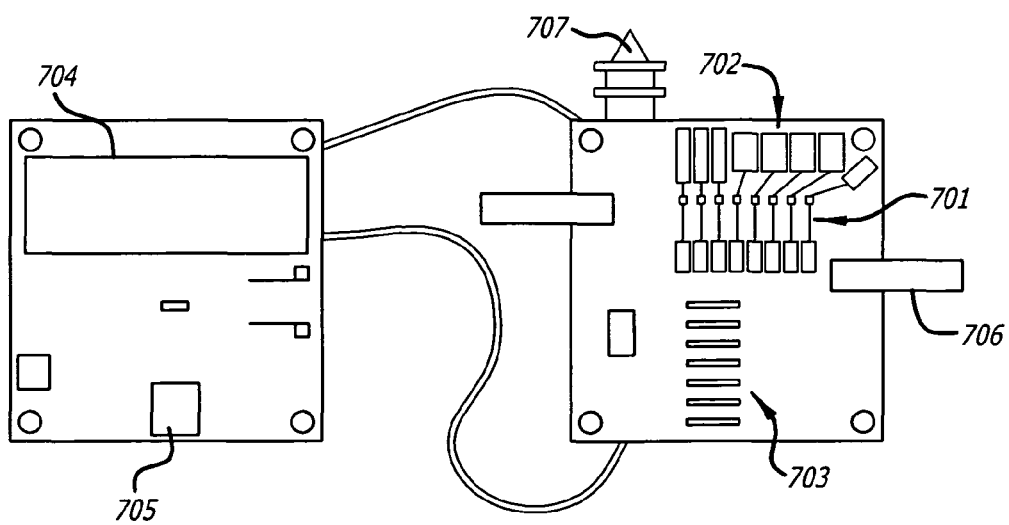
FIG. 51 depicts avalanche pulse generator circuit board assembly.

Component and layout of parasitics may play a role in distorting a subnanosecond rise time in the higher end stages of the tapered line. Especially when generating pulses in the sub-nanosecond regime. In addition to using carefully selected low parasitic surface mount components in the pulse generating section of the circuit, all interconnections have been made short to ensure low parasitic inductances. Further, in the exemplary embodiment we used pads on a doublesided 0.062" FR-4 epoxy glass laminate pc-board for capacitors $C_6$-$C_8$ instead of soldering on 3 ATC capacitors. Since the pc-board dielectric has a low series inductance, this improves the pulse rise time significantly (FIG. 51). The Avalanche transistors are shown at 701, PCBorad capacitors 702, Zener chain 703, 2.5 kv DC-DC 704, 8-14.5 Vdc in 705, Trigger In 706 and 707 the pulse out direction at 50 ohm load.

Voltage Measurement

Direct measurement of kilovolt transitions in hundreds of picoseconds has been challenging. Methods such as voltage division based on inductive coupling capacitive compensation are impractical because of limitations imposed by component self resonant frequencies.

Figure 52A:
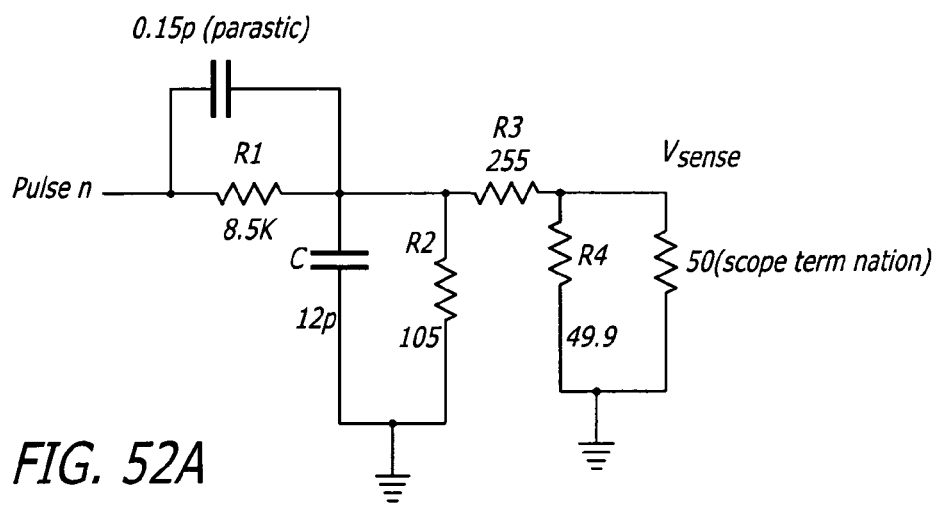
FIG. 52A depicts the exemplary embodiment of the voltage divider schematic.

In the present alternative embodiment our system features a custom-made high bandwidth, capacitively compensated resistive voltage divider (FIG. 52A). The divider is built into the pulse generator and enables direct, measurement of our subnanosecond high voltage pulse. The nominal voltage division ratio is 1400:1 and the divider has a +3 dB point at 910 MHz.

The divider has a resistive backbone, and is built on a standard 2-layer printed circuit board. Resistors are SMT 1206 package metalized film chip resistors. Because of the proximity of contacts on a ceramic substrate, these resistors have a shunt parasitic capacitance of 0.1-0.2 pF. To overcome the bandwidth limitation imposed by this parasitic, capacitive compensation is necessary. The compensation capacitor C is of type ATC100A from American Technical Ceramics Corp. These are high quality microwave capacitors, having low loss and high self-resonant frequency. The divider has been designed as a two stage resistive divider to minimize the number of compensating capacitors needed to maintain a flat attenuation over our desired bandwidth. This minimizes the dependence of the frequency response on the self-resonant frequencies of these components.

Figure 52B:
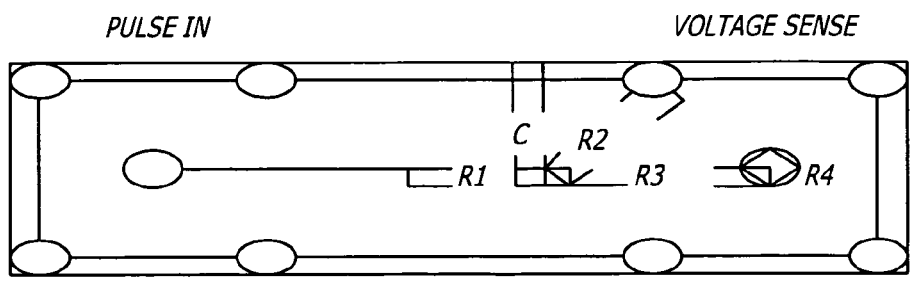
FIG. 52B depicts schematic of the voltage divider layout on a two layer pc-board.

The layout of our divider can minimize parasitic interferences (FIG. 52B). All components can be placed on their sides to ensure small footprints and minimal parasitic capacitance to ground. In particular, resistors on the low side of the divider can be mounted directly onto the SMA connector to eliminate stray interconnect inductances.

Figure 53:
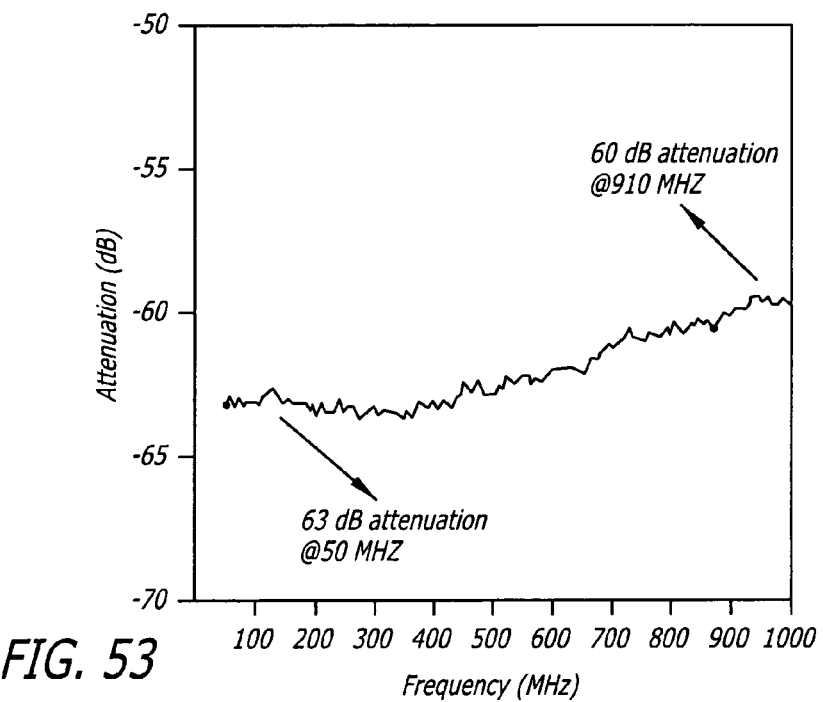
FIG. 53 depicts the frequency response of compensated resistive voltage divider designed to measure subnanosecond rise time pulses. Attenuation is amplitude of S21/(1+S11) in db, as measured on an Agilent 8720ET Network Analyzer. Measurement span is 50 MHz to 1 GHz.

This technique also can minimize any distortion in frequency response that may arise from capacitive coupling to the high voltage end. The frequency response (FIG. 53) of the divider is measured on an Agilent 8720ET network analyzer. The divider's bandwidth is limited by the selfresonance of the compensation capacitor, and other high frequency resonances.

The following sections discuss operation of the pulse generator into a 50Ωresistive load and a micro-machined slide [8] containing biological cells in liquid suspension.

Operation with 50Ω Resistive Load

Figure 54:
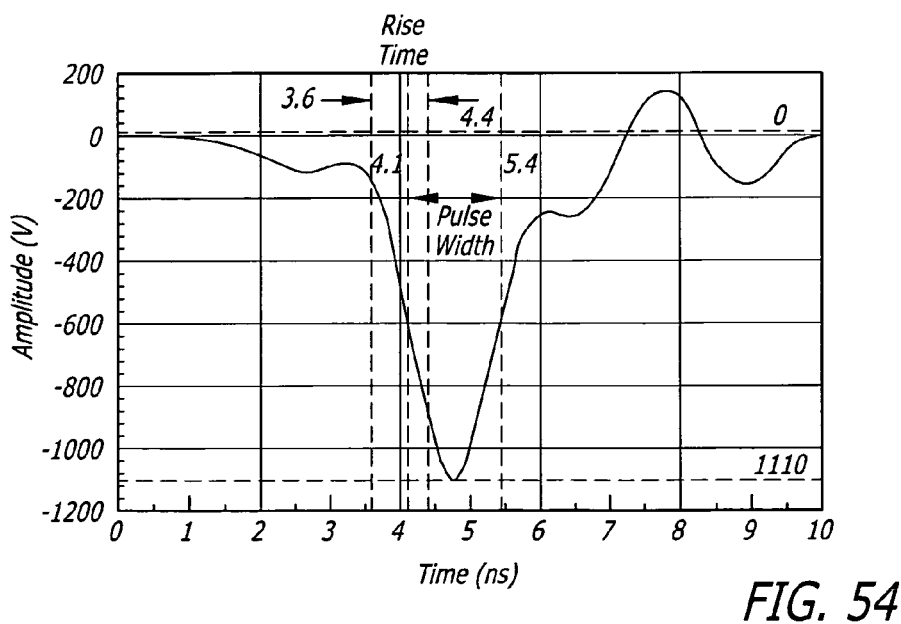
FIG. 54 depicts output pulse into 50 ohm resistive load as measured by the custom voltage divider in FIGS. 52 and 53.

Repetition rate can be 200 kHz by pulse current heating of the transistors. The maximum power dissipation in the zener diodes, and the Rcharge*C1 time constant can be limiting factors. The all solid-state nature of the pulse generator can ensure reproducible pulses and increases reliability. The typical output into a 50Ω resistive load is as shown in FIG. 54. The pulse amplitude in an alternative embodiment being 1110 V; rise time (10% to 90%) is 0.8 ns, and the full width half maximum (FWHM) is 1.3 ns. The energy delivered by the generator to this matched load can be as low as 32 μJ. The pulse amplitude increases from 900 V to 1100 V as the voltage supply can be varied from 8 V to 14.5 V. The pulse width and rise time can be fairly independent of the amplitude.

Biological Load and Integration

The biological load is an instrumented microscope slide, containing gold deposited electrodes or any other suitable metals separated by 100 μm. The cell solution is put into the micro chamber between electrodes, and covered by a glass cover slip. The load impedance of this setup when the cell solution is loaded may be of the order of 100 s of ohms. Different cell solutions could have different impedance values, and the effects of pulsed electric fields could also cause variability in load impedance during experimentation. Therefore, the pulse generator in the exemplary embodiment has been designed to drive an effective load impedance of 50Ω—designed as the parallel combination of a small SMT resistor and the loaded micro chamber. This is advantageous because we can easily interface the pulse generator output to the load using a 50Ω coaxial cable. The paralleling of a small resistor with the higher impedance cell slide also can allow for a good match over variable cell impedances, as changes in biological loads may not significantly affect the effective load seen by the pulse generator.

Figure 55:
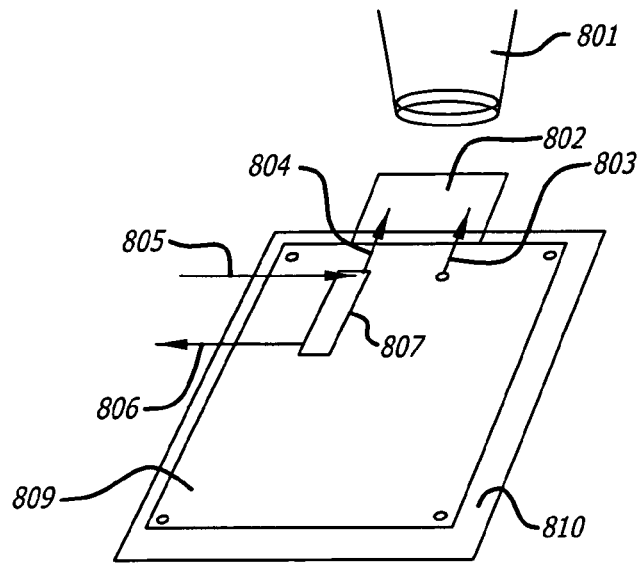
FIG. 55 depicts schematic of the setup that integrates the avalanche pulse generator with the biological load and the microscope.

The exemplary embodiment of the block diagram of the setup used to deliver pulses into the above biological load is shown in FIG. 55. The slide with sample cell 802 is placed in between the two transmission lines T1 and T2, 804 and 803, respectively. The voltage probe as shown in FIG. 52A is installed and shown at 807. The setup enables us to image in real-time the high voltage subnanosecond pulse-induced effects 805 under a Zeiss Axiovert microscope 801. The PC-board 809 is placed on the insert stage 810 of the microscope which serves a dual purpose. First, it acts as an interface component between the pulse generator and the electrodes on the microscope slide containing the cell sample under study. Second, it contains the custom-made voltage divider (FIGS. 52B, 53) to monitor pulse characteristics 806 at the load. This monitoring can be important many reasons such as a) to ensure that all connections are in place and the pulse is delivered to the load and b) monitor pulse shape at the load that could be different from the pulse measured at the point of pulse generation since the biological load is not a perfectly resistive 50Ω load.

Figure 56:
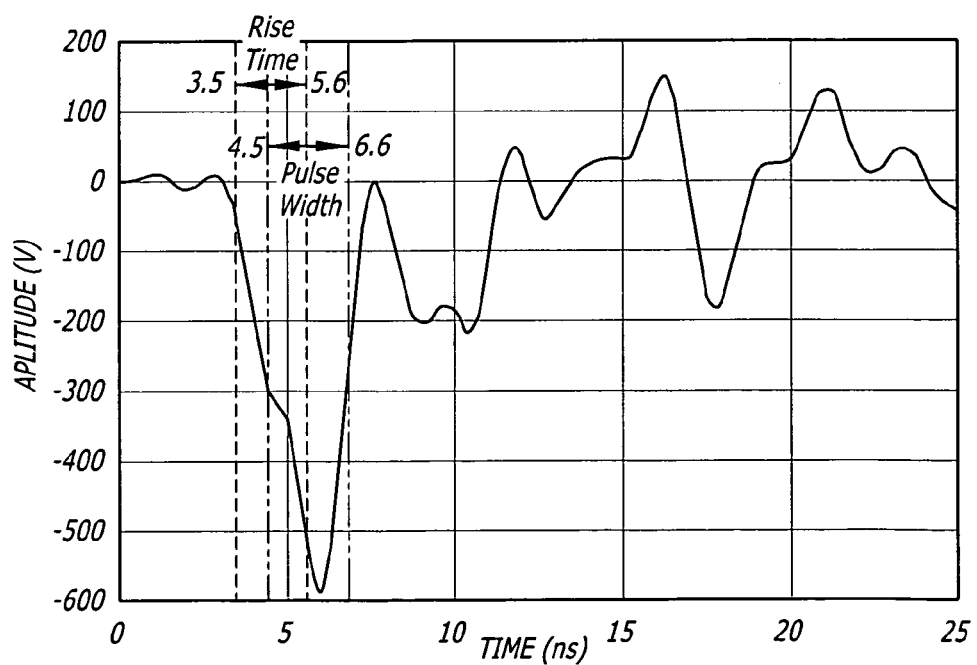
FIG. 56 depicts the output of the avalanche pulse generator into a loaded slide as measured by the custom made voltage monitor on the microscope insert stage. Pulse is rising from 3.5 ns to 5.6 ns, and pulse width is seen as 6.6-4.5 ns=2.1 ns.

FIG. 56 shows the output pulse of the avalanche pulser interfaced to the biological load as measured by the voltage monitor on the insert stage. This output pulse has ~half the pulse amplitude (600 V) and ~1.5 times the pulse width (2.1 ns) of the output pulse delivered into a purely resistive 50Ω load (FIG. 54). There may be several reasons that cause this distortion of pulse parameters. The many reasons of distortion may have to do with the physical configuration of the interfacing setup shown in FIG. 56 particularly the transmission lines T1 and T2 connecting the electrodes on the slide to the 50Ω cable delivering the output pulse to the load.

Transmission lines T1 and T2 introduce load parasitics that could distort pulse shape by causing impedance mismatch between the tapered transmission line in the pulse generator and the load.

Figure 57:
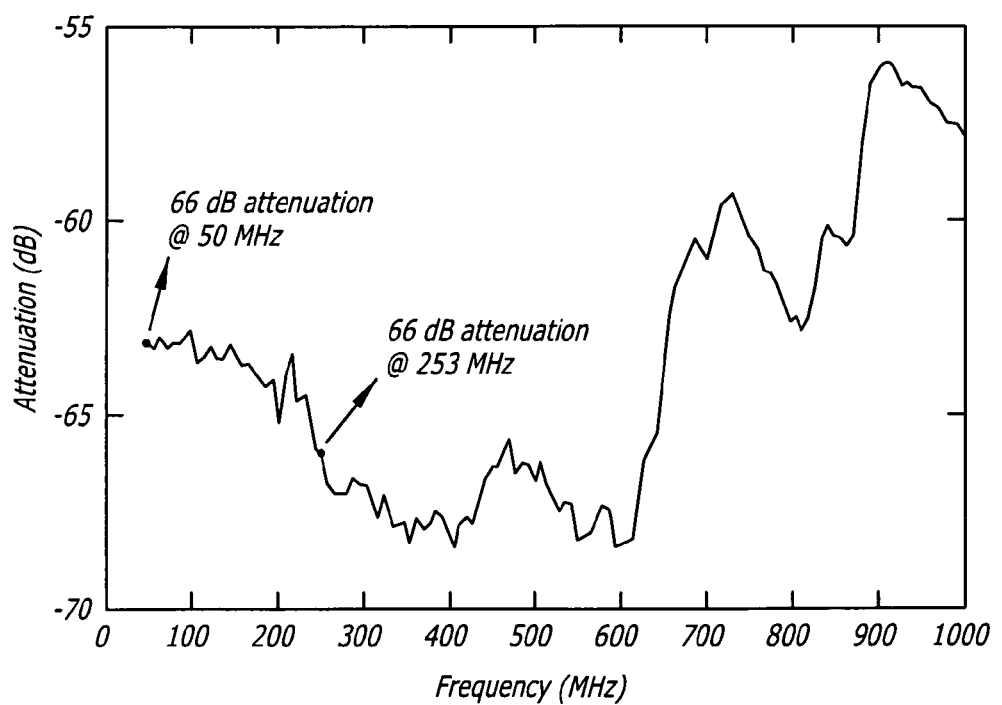
FIG. 57 depicts the exemplary frequency response of the compensated resistive voltage divider (FIG. 52). Interfaced with the micro-chamber containing cells in suspension.

Also, transmission lines T1 and T2 may affect the accuracy of the voltage divider on the insert stage pc-board by capacitively coupling to the high impedance end of the voltage divider. This capacitive coupling limits the bandwidth of the voltage divider to ~250 MHz (FIG. 57) which is in stark contrast with the frequency responses of the same voltage divider measuring the pulse delivered to a 50Ω resistive load (FIG. 52A and FIG. 55). This bandwidth limitation could mean that the measurement in FIG. 56 is a distorted version of the actual pulse delivered.

Therefore, redesigning the microscope/slide interface with a careful consideration of the parasitics, high frequency resonances and coupling issues will among many other advantages a) ensure a good match between the pulse generator and the load, and b) allow for reliable and measurable delivery of our 1.1 kV 1.3 ns pulses to biological loads.

Interfacing Setup Design

In the exemplary embodiment we have designed a biophotonic experimental setup that can ensure a good match between the subnanosecond pulse generator and the low impedance biological load under study. The setup can enable the delivery of an undistorted subnanosecond rise-time high voltage pulse at high repetition rates to the load. In the exemplary embodiment the setup is designed so as to facilitate microscopic observation of cellular responses to the pulses, as and when they are delivered.

Figure 58B:
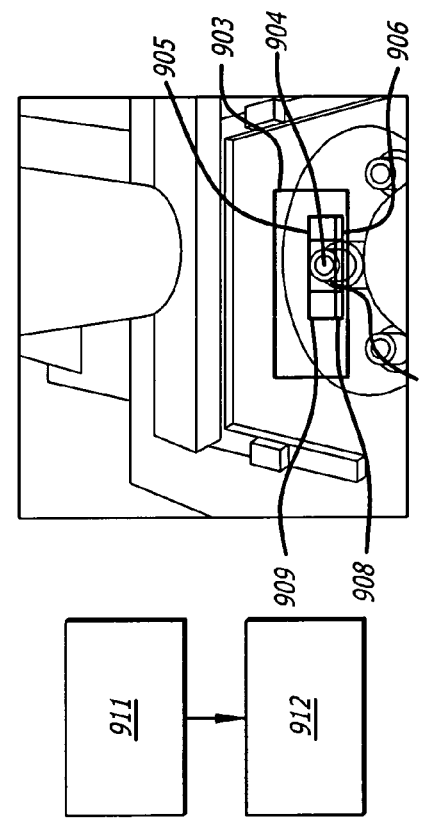
FIG. 58A-C depict the zeiess Axiovert microscope setup that is used to conduct real-time biophotonic studies of mamoelectropulse-induced cellular effects.
Figure 58C:
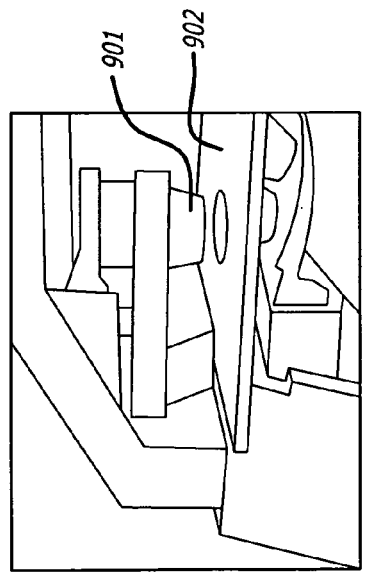
Figure 58A:
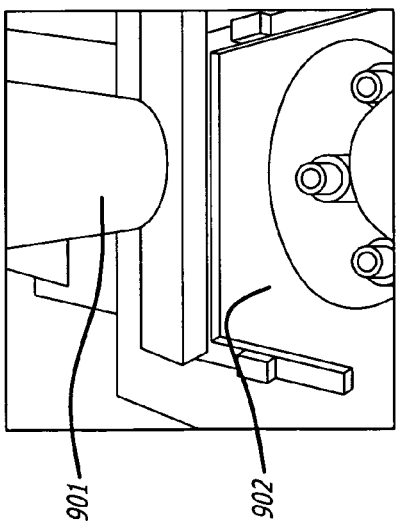

FIG. 58A-C includes a side and top views of the setup. The setup may consist of a) a printed circuit board 912 to interface the pulse generator 911 to the cell solution load on the glass slide 907 under the microscope aperture 901 and b) a micro-machined glass slide to hold the cell solution under study. The printed circuit board 912 can be laid flat on the microscope stage 902, and contains a low-parasitic pulse delivery system designed as an impedance matching network. The micro-machined glass slide 907 contains electrodes 905 and 906 spaced apart as ground and high voltage electrodes, respectively.

The pc-board and the slide combination is designed that can match the load impedance of the pulse generator. This can minimize reflections back into the pulse generator, and minimize distortion of the shape and parameters of the subnanosecond pulse delivered to the load. The voltage divider is built into the interfacing pc-board that can allow for real-time monitoring of the pulses that are delivered to the cell solution, at the load itself. The electrodes on the microchamber may directly contact the HV pulse carrying traces on the insert stage pc-board.

I. Design of the Set Up

The exemplary experimental setup design may consist of a micromachined glass slide to hold the cell solution under study, and a printed circuit board to interface the pulse generator to the cell solution load.

A. The Micro-Machined Slide

Figure 59:
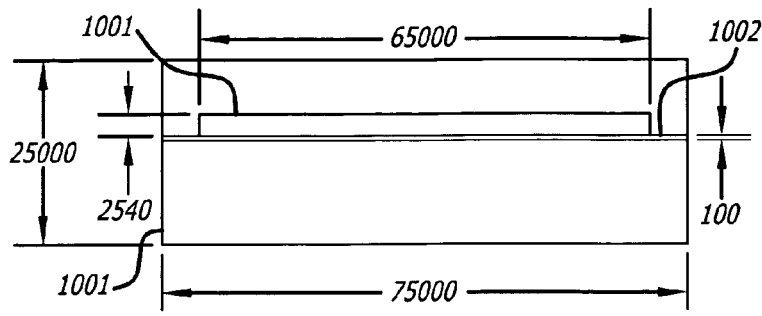
FIG. 59 depicts mask for the microchamber.
Figure 60A:
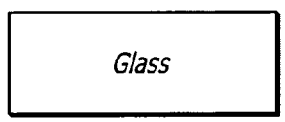
FIG. 60 depicts the micromachining process step.
Figure 60B:
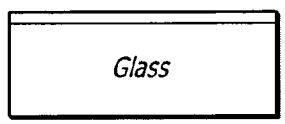
Figure 60C:
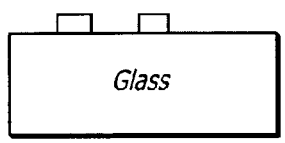
Figure 60D:
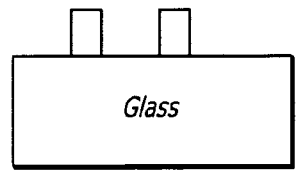
Figure 60E:
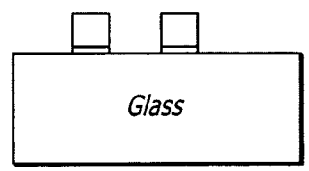
Figure 61:
FIG. 61 depicts the custom fabricated microscope glass slide.

FIG. 60 shows the process steps to fabricate the microchamber illustrated in FIG. 59. A glass slide may be first cleaned with piranha at (a). Then it can be evaporated with a 50 A Ti and 1000 A Au (b) as a seed layer. After patterning the micro chamber (c), an Au electroplating can be performed (d). The thin Ti seed layer may be finally etched away (e). FIG. 61 depicts a custom-fabricated microscope glass slide 1003 with electrodes 1001 having the channel width 1002 to hold the cell solution.

B. The New Microscope Insert Stage and Slide Interface

Figure 62:
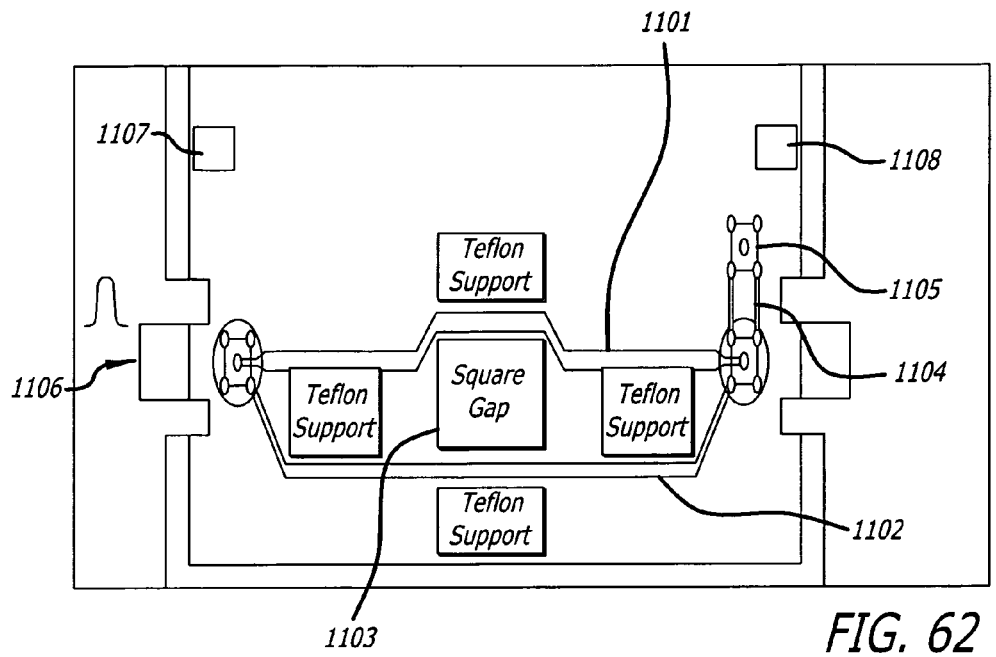
FIG. 62 depicts the cartoon of pc-board designed to interface the pulse generator to the slide and microscope.

To reduce parasitics, the electrical system can be interfaced with the microchamber, the pulse generator and the microscope insert stage. The system has been designed as a printed circuit board that can be laid flat on the microscope stage (FIG. 62).

The HV pulse carrying trace on the pc-board can be designed to have an impedance of 50Ω to match the load impedance of the avalanche pulse generator. This can minimize reflections and prevents distortion of the subnanosecond pulse delivered to the cell load. The voltage divider can be built into the interfacing pc-board, to allow for real-time monitoring of pulses delivered to the cell solution. The square gap in the pc-board may prevent the cell culture under the cover slip from being pushed against the pc-board—thereby it can ensure that the cells under observation (under the cover slip) do not get smashed.

C. Connecting the Slide to the Interface

Figure 63:
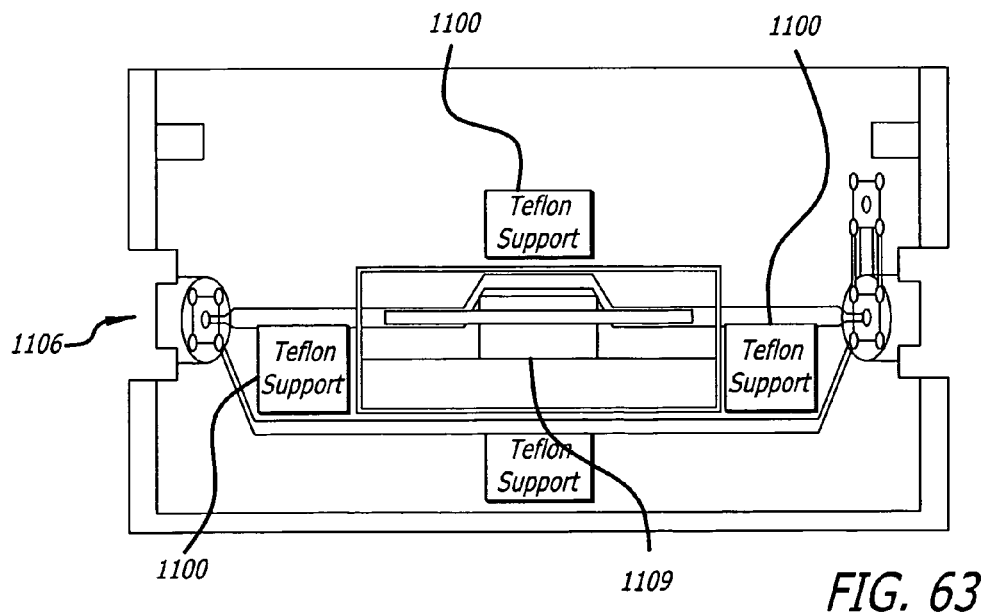
FIG. 63 depicts the pc-board interface connected to the glass slide containing the cell solution under test.

The arrangement in FIG. 63 parallels a cell solution containing microchamber with a 50 • transmission line. The traces on the microchamber may directly contact the traces on the insert stage pc-board. Therefore, the impedance that parallels the 50 • traces may not depend on properties of the micro-machined traces on the glass slide, but merely depends on the solution placed in the channel between the two micro-machined traces. It can be ensured that the connection is low parasitic by inverting the slide so the HV and GND electrodes on the slide contact the HV pulse and GND traces on the pc-board 1109. Teflon clasp 1110 can be used to hold the glass slide in place so that the micromachined electrodes contact the pc-board traces.

Cell solutions are similar to saline solutions known to have high electrical impedance. Therefore, the arrangement may parallel a very high impedance load with a 50Ω transmission line. The net impedance seen by the pulse generator is still close to 50 • thus minimizing the imminent mismatch between the pulse generator and the biology load. The paralleling of a low 50 • impedance with the higher impedance cell slide can allow for a good match over variable cell impedances as changes in biological loads would not significantly affect the effective load seen by the pulse generator.

Figure 64:
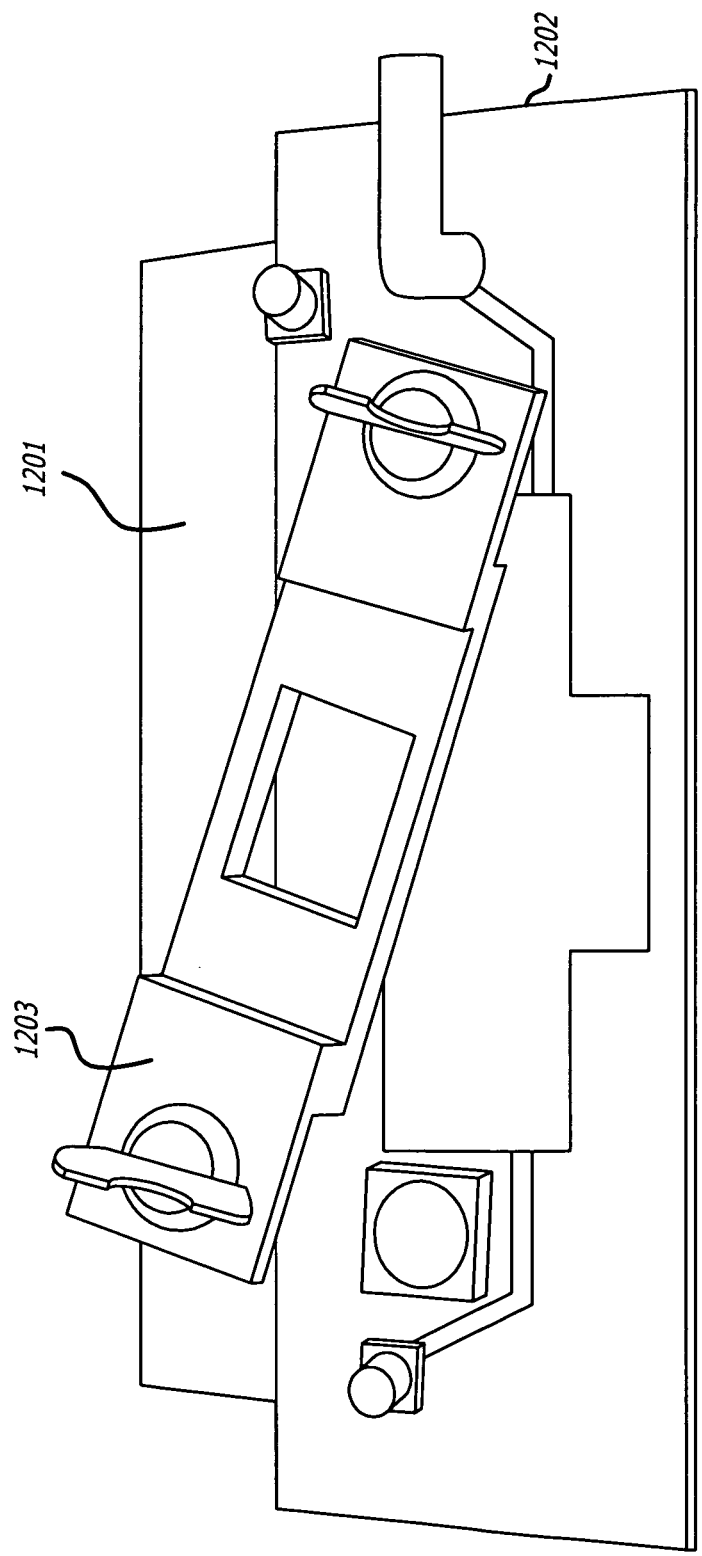
FIG. 64 depicts an image of a microchamber interfaced with the insert stage pc-board.
Figure 65:
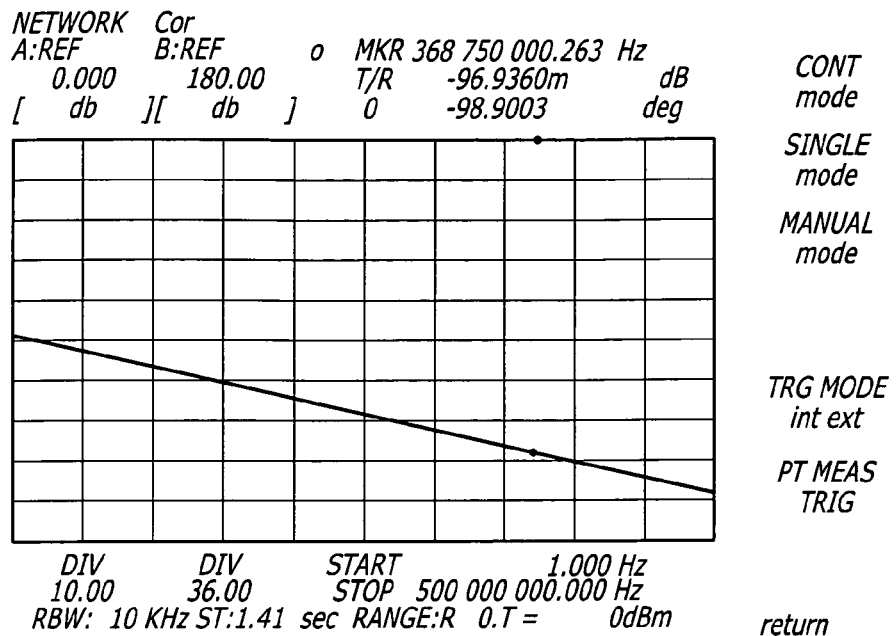
FIG. 65 depicts the network analyzer T/R response of the traces on the interfacing pc-board without the slide in place as illustrated in FIG. 62.

FIG. 64 depicts the image of the microchamber interfaced with the insert stage pc-board 1201. The insert stage pc-board interfaced to pulser with the load and the microscope includes depicts the voltage out 1202 through the voltage divider board and to scope, silver cover Plate fastener 1203 and the 50Ω transmission line on the insert instead of 50Ω resistor.

II. Testing

Figure 66:
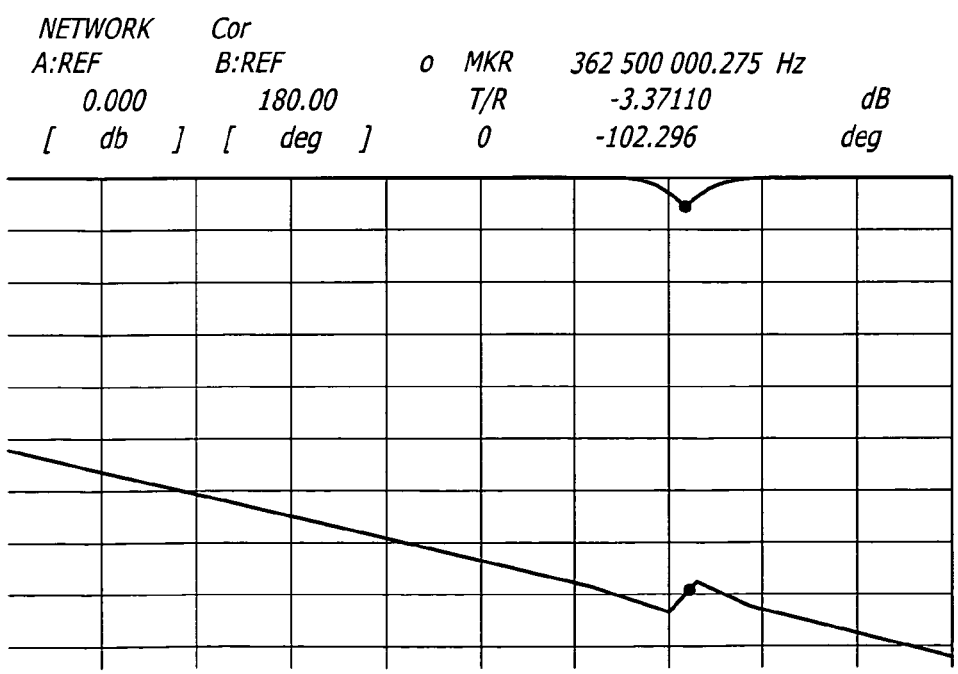
FIG. 66 depicts the network analyzer T/R response of the interfacing pc-board integrated with the custom fabricated slide containing RPMI solution as shown in FIGS. 63 and 64.

Impedance matching tests were conducted to validate that the interface designed above indeed matches the 50Ω load impedance of the subnanosecond pulse generator. 50Ω cables can be used to connect the output of the power splitter and the transmission port of the network analyzer to the pc-board shown above. Measurement span is 10 Hz to 500 MHz. The frequency responses obtained are shown in FIGS. 5 and 66.

There is a nearly 0 dB T/R ratio, and a perfectly linear phase indicating that the pc-board presents a 50Ω impedance load to the pulse generator. This is a well matched transmission line system.

The magnitude of the T/R frequency response can be largely 0 dB and the phase can be mostly linear. There is one −2 dB kink at 350 MHz, and this could be due to a slight mismatch in the transmission line matching due to an air gap because the slide was not contacting the electrode fully. This can be fixed by ensuring that the electrodes on the micromachined slide have a uniform thickness of 15 μm. Even though a more uniform contact can ensure better impedance matching, we posit that this may not be a significant issue as far as delivering the pulse to the load is concerned because even a 50% contact can ensure delivery of an undistorted pulse. This can be seen by comparing the oscilloscope measurements shown in FIGS. 67 and 78.

Figure 67:
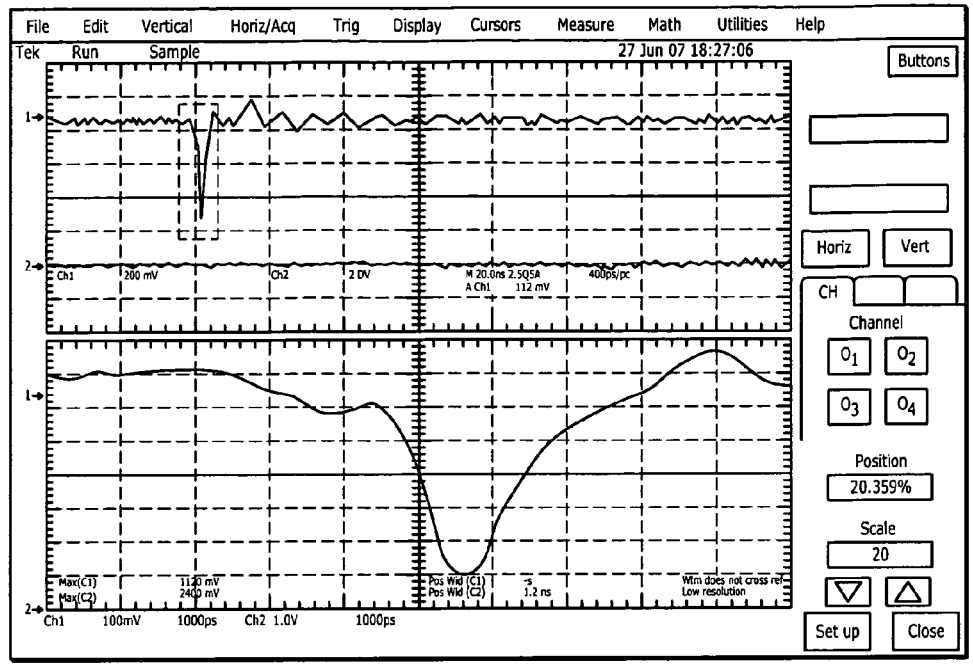
FIG. 67 depicts Ch1=voltage delivered to a 50 ohm resistive termination attached to the output SMA jack=1410 measure voltage on scope.
Figure 68:
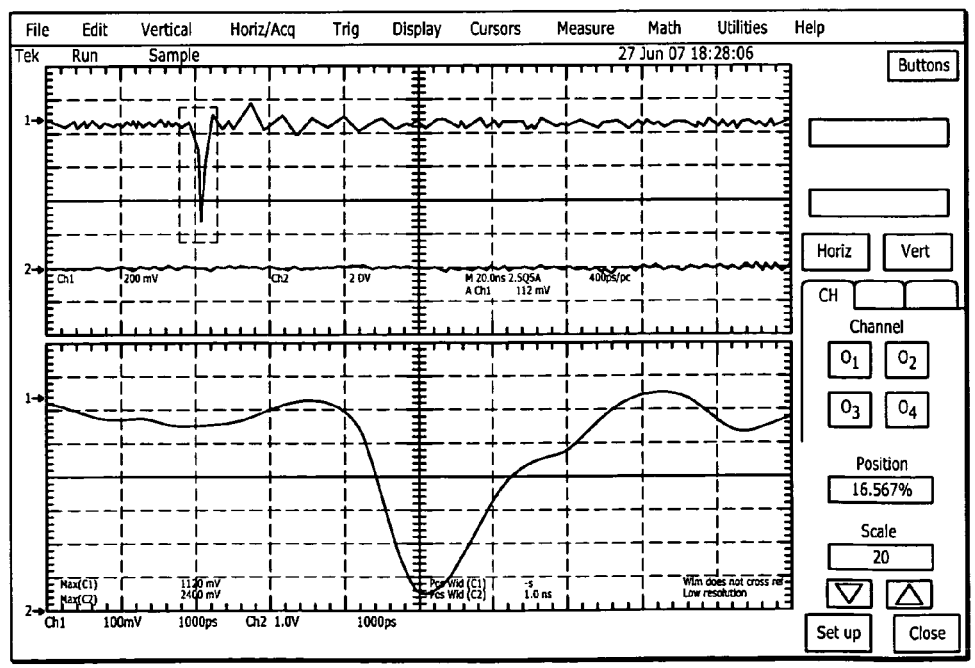
FIG. 68 depicts Ch1=voltage delivered to an RPMI solution connected to the pulse generator in the newly designed interfacing setup=1410 measure voltage on scope.

As seen in the FIGS. 67 and 68, the pulse delivered to a biological solution in the new interfacing setup (FIG. 68) has the same rise time and amplitude as the pulse delivered by the generator to a 50Ω resistive load (FIG. 67). In each case, the pulse delivered at the load is measured using a custom made 910 MHz bandwidth 1410:1 voltage divider on the interfacing pc-board [4].

Therefore, our exemplary matching network interface facilitates the delivery of an undistorted subnanosecond rise time pulse to a biological load being imaged under a microscope.

The following publications are hereby incorporated by reference in their entirety: P. T. Vernier, Y. Sun, J. Wang, M. M. Thu, E. B. Garon., M. Valderrabano, L. Marcu, H. P. Koeffler, and M. A. Gundersen, "Nanoelectropulseintracellular perturbation andelectropermeabilization technology: phospholipid translocation, calcium bursts, chromatin rearrangement, cardiomyocyte activation, and tumor cell sensitivity", 27th Annual Intern. Conf. IEEE Engineering in Medicine and Biology Society, Shanghai, pp. 5850-5853, 2005; K. H. Schoenbach, S. J. Beebe, and E. S. Buescher, "Intracellular Effect of Ultrashort Electrical Pulses", Bioelectromagnetics, Vol. 22, pp. 440-448, 2001. P. T; Vernier, Y. Sun, L. Marcu, S. Salemi, C. M. Craft, and M. A. Gundersen, "Calcium bursts induced by nanosecond electric pulses", Biochemical and Biophyiscal Research Communications, Vol. 310, pp; 286-295, 2003. A. Kuthi, M. Behrend, P. Thomas Vernier, and M. A. Gundersen, "Nanosecond Pulse Generator Using Fast Recovery Diodes for Cell Electromanipulation", IEEE Trans. Plasma Sci., Vol. 33, pp. 1192-1197, 2005; E. S. Fulkerson and R. Booth, "Design of Reliable High Voltage Avalanche Transistor Pulsers", IEEE 21st Intern. Power Modulator Symposium, p. 101-103, 1994; S. Vainshtein, J. Kostamovaara, A. Kilpela and K. Maatta, "A novel compact 35 A/150 ps current pulse generator for a new generation of the laser radars", 40th Midwest Symposium on Circuits and Systems, Vol. 1, No. 3-6, pp. 148-151, 1997; M. R. Behrend, A. Kuthi and M. A. Gundersen, "DC to 1 Gigahertz multikilovolt voltage probe", 26th Intern. Power Modulator Symposium and High Voltage Workshop, pp. 341-343, 2004; Y. Sun, P. T. Vernier, M. Behrend, L. Marcu, and M. A. Gundersen, "Electrode microchamber for noninvasive perturbation of mammalian cells with nanosecond pulsed electric fields", IEEE Trans. Nanobiosci., Vol. 4, pp. 277-283, 2005; M. Behrend, A. Kuthi, X. Gu, P. T. Vernier, L. Marcu, C. M. Craft and M. A. Gundersen, "Pulse Generators for pulsed electric field exposure of biological cells and tissues", IEEE Trans. Dielectr. Electr. Insul., Vol. 10, pp. 820-825, 2003.

While a number of preferred embodiments of the invention and variations thereof have been described in detail, other modifications and methods of use will be readily apparent to those of skill in the art. Accordingly, it should be understood that various applications, modifications and substitutions may be made of equivalents without departing from the spirit of the invention or the scope of the claims.

We claim:

1. A solid-state sub-nanosecond rise time pulse generator for driving variable impedance biological loads, the pulse generator comprising:
   a) a transmission line comprising a series chain of N (N is integer number >=2) avalanche transistors configured to switch a high voltage DC supply to substantially ground within hundreds of picoseconds and to generate high voltage electric pulses having a sub-nanosecond (<1 ns) rise time;
   b) a trigger circuit to initiate the switching via an avalanche breakdown mechanism in the transistors of the transmission line from a lower end voltage side to a higher end voltage side;
   c) N capacitors electrically connected to collectors of each avalanche transistor, configured so that the capacitor's impedance decreases from the lower end voltage side to the higher end voltage side;
   d) a chain of N zener diodes, each placed across a corresponding avalanche transistor, the chain configured to divide a high voltage DC supply across the transistors, wherein the diodes are so configured as to enable a non-destructive avalanche breakdown of the transistor or transistors of the higher end voltage side upon triggering from the transistor or transistors of the lower end voltage side, wherein the zener diode or zener diodes at the higher end voltage side are configured to have a lower nominal voltage rating than the zener diode or zener diodes at the lower end voltage side.

2. The pulse generator of claim 1, further comprising a pc-board, and wherein the capacitors are formed as metallic pads on the pc-board.

3. The pulse generator of claim 2, wherein the formed capacitors are configured to reduce electrical parasitic effects in the circuit.

4. The pulse generator of claim 2, wherein the pads are formed on the pc-board as traces configured to connect the capacitors to the transistors.

5. The pulse generator of claim 1, wherein the pc-board is made by double sided epoxy glass laminate dielectric.

6. The pulse generator of claim 1, wherein the zener diodes are selected based on an asymmetry characterization of their nominal voltage ratings.

7. The pulse generator of claim 1, wherein the avalanche transistors generate high voltage electric pulses having a width $<=1.5$ ns.

8. The pulse generator of claim 1, wherein the electric pulses are generated at a repetition rate $<=200$ kHz.

9. The pulse generator of claim 1, wherein the pulse generator is configured to generate high voltage electric pulses having the voltage amplitude of about 2 kV.

10. The pulse generator of claim 1, wherein the zener diodes have nominal voltage ratings of 280V-300V.

11. The pulse generator of claim 1, further comprising a voltage divider for measuring a sub-nanosecond rise time (<1 ns) high voltage electric pulse, the voltage divider comprising:
   a. a plurality of resistors having a metalized film of surface mount 1206package;
   b. a distributed parasitic compensation network comprising at least one capacitor configured to compensate for inherent electrical parasitic effects in the resistors and to extend divider bandwidth;
   c. a receiving port configured to receive a high voltage nanosecond electric pulse; and
   d. a voltage sensing port configured to put out a voltage measurement of a received electrical pulse in real-time.

12. The pulse generator of claim 11, wherein the resistors and the capacitors of the voltage divider rest on non-metallic edges, configured to limit electrical parasitic effects on division bandwidth.

* * * * *